United States Patent
Ayers et al.

(10) Patent No.: US 11,377,693 B2
(45) Date of Patent: Jul. 5, 2022

(54) SYSTEM AND METHODS FOR DERIVING GENE SIGNATURE BIOMARKERS OF RESPONSE TO PD-1 ANTAGONISTS

(71) Applicants: Mark D. Ayers, Pennington, NJ (US); Andrey Loboda, Canton, MA (US); Jared K. Lunceford, Washington, UT (US); Terrill K. McClanahan, Sunnyvale, CA (US); Erin E. Murphy, Redwood City, CA (US); Michael Nebozhyn, Colmar, PA (US); Merck Sharp & Dohme Corp., Rahway, NJ (US)

(72) Inventors: Mark D. Ayers, Pennington, NJ (US); Andrey Loboda, Canton, MA (US); Jared K. Lunceford, Washington, UT (US); Terrill K. McClanahan, Sunnyvale, CA (US); Erin E. Murphy, Redwood City, CA (US); Michael Nebozhyn, Colmar, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 1167 days.

(21) Appl. No.: 15/533,769

(22) PCT Filed: Dec. 8, 2015

(86) PCT No.: PCT/US2015/064445
§ 371 (c)(1),
(2) Date: Jun. 7, 2017

(87) PCT Pub. No.: WO2016/094377
PCT Pub. Date: Jun. 16, 2016

(65) Prior Publication Data
US 2018/0327848 A1 Nov. 15, 2018

Related U.S. Application Data

(60) Provisional application No. 62/089,538, filed on Dec. 9, 2014, provisional application No. 62/160,284, filed on May 12, 2015.

(51) Int. Cl.
| | | |
|---|---|---|
| *C12Q 1/6886* | (2018.01) |
| *G16B 20/00* | (2019.01) |
| *G16B 30/00* | (2019.01) |
| *G16B 40/00* | (2019.01) |
| *C07K 16/28* | (2006.01) |
| *C12Q 1/68* | (2018.01) |
| *G16B 40/30* | (2019.01) |
| *G16B 20/20* | (2019.01) |
| *G16H 50/30* | (2018.01) |
| *A61K 39/00* | (2006.01) |

(52) U.S. Cl.
CPC ........ *C12Q 1/6886* (2013.01); *C07K 16/2818* (2013.01); *C12Q 1/68* (2013.01); *G16B 20/00* (2019.02); *G16B 20/20* (2019.02); *G16B 30/00* (2019.02); *G16B 40/00* (2019.02); *G16B 40/30* (2019.02); *G16H 50/30* (2018.01); *A61K 2039/505* (2013.01); *C07K 2317/24* (2013.01); *C07K 2317/76* (2013.01); *C12Q 2600/106* (2013.01); *C12Q 2600/158* (2013.01)

(58) Field of Classification Search
CPC ........ C12Q 1/6886; C12Q 1/68; G16H 50/30; G16B 40/00; G16B 20/00; G16B 30/00; C07K 16/2828
See application file for complete search history.

(56) References Cited

U.S. PATENT DOCUMENTS

| | | | |
|---|---|---|---|
| 2012/0094374 A1 | 4/2012 | Bentwich et al. | |
| 2013/0034540 A1* | 2/2013 | Mule | C12Q 1/6886 424/130.1 |
| 2013/0142809 A1* | 6/2013 | Welcher | G01N 33/68 424/145.1 |
| 2018/0148790 A1 | 5/2018 | Ayers | |

FOREIGN PATENT DOCUMENTS

| | | |
|---|---|---|
| WO | 2011094483 A2 | 12/2011 |
| WO | 2014009535 A2 | 1/2014 |
| WO | 2014022826 A2 | 2/2014 |
| WO | 2014151006 A2 | 9/2014 |
| WO | 2014194293 A1 | 12/2014 |
| WO | 2015094992 A1 | 6/2015 |
| WO | 2015094995 A2 | 6/2015 |

(Continued)

OTHER PUBLICATIONS

Dolan et al., PD-1 Pathway Inhibitors: Changing the Landscape of Cancer Immunotherapy, Jul. 2014, 21(3), p. 231-237 (Year: 2014).*

(Continued)

*Primary Examiner* — Olivia M. Wise
*Assistant Examiner* — Kaitlyn L Minchella
(74) *Attorney, Agent, or Firm* — Sarah L. Hooson; Alysia A. Finnegan

(57) ABSTRACT

A gene expression platform, which is a combination of a set of genes that are correlated with response to a PD-1 antagonist in multiple tumor types and a normalization gene set, is disclosed. A method and system of using the gene expression platform to derive gene signature biomarkers of anti-tumor response to a PD-1 antagonist and to test patient samples for predictive gene signature biomarkers are also disclosed.

7 Claims, 22 Drawing Sheets

(56) References Cited

FOREIGN PATENT DOCUMENTS

WO     2015094996 A2    6/2015

OTHER PUBLICATIONS

Chen et al., Interferon-γ-induced PD-L1 surface expression on human oral squamous carcinoma via PKD2 signal pathway, 2012, Immunobiology, 217, p. 385-393 (Year: 2012).*

NanoString Technologies, Inc. (Multiplexed Cancer Immune Response Analysis), Sep. 2014, pp. 1-8.

Ascierto et al., Biomarkers for Immunostimulatory Monoclonal Antibodies in Combination Strategies for Melanoma and Other Tumor Types, Clinical Cancer Research, 2013, pp. 1009-1020, vol. 19, No. 5.

Ahmadzadeh et al., Tumor antigen-specific CD8 T cells infiltrating the tumor express high levels of PD-1 and are functionally impaired, Blood, 2009, 1537-1544, 114.

Dong et al., Tumor-associated B7-H1 promotes T-cell apoptosis: A potential mechanism of immune evasion, Nature Medicine, 2002, 793-800, 8(8), Apr. 22, 2020.

Eisenhauer et al., New response evaluation criteria in solid tumours: Revised RECIST guideline (version 1.1), Eur. J. Cancer, 2009, 228-247, 45.

Gao et al., Overexpression of PD-L1 Significantly Associates with Tumor Aggressiveness and Postoperative Recurrence in Human Hepatocellular Carcinoma, Clinical Cancer Research, 2009, 971-979, 15.

Geiss et al., Direct multiplexed measurement of gene expression with color-coded probe pairs, Nature Biotechnology, 2008, 317-325, 26(3).

Ghebeh et al., FOXP3+ Tregs and B7-H1+/PD-1+T lymphocytes co-infiltrate the tumor tissues of high-risk breast cancer patients: Implication for immunotherapy, BMC Cancer, 2008, 57-68, 8.

Ghebeh et al., The B7-H1 (PD-L1) T Lymphocyte-Inhibitory Molecule Is Expressed in Breast Cancer Patients with Infiltrating Ductal Carcinoma: Correlation with Important High-Risk Prognostic Factors, Neoplasia, 2006, 190-198, 8.

Hamanishi et al., Programmed cell death 1 ligand 1 and tumor-infiltrating CD8+ T lymphocytes are prognostic factors of human ovarian cancer, Proceedings of the National Academy of Sciences USA, 2007, 3360-3365, 104.

Hino et al., Tumor cell expression of programmed cell death-1 ligand 1 is a prognostic factor for malignant melanoma, Cancer, 2010, 1757-1766, 116(7).

Inman et al., PD-L1 (B7-H1) expression by urothelial carcinoma of the bladder and BCG-induced granulomata: associations with localized stage progression, Cancer, 2007, 1499-1505, 109.

International Search Report of PCT/US15/64445 dated May 17, 2016.

J. Compton, Nucleic acid-sequence based amplification, Nature, 1991, pp. 91-92, 350(6313).

Nakanishi et al., Overexpression of B7-H1 (PD-L1) significantly associates with tumor grade and postoperative prognosis in human urothelial cancers, Cancer Immunol. Immunother., 2007, 1173-1182, 56.

Nishino et al., Developing a Common Language for Tumor Response to Immunotherapy: Immune-related Response Criteria using Unidimensional Measurements, Clinical Cancer Research, 2013, 3936-3943, 19(14).

Nomi et al., Clinical Significance and Therapeutic Potential of the Programmed Death-1 Ligand/Programmed Death-1 Pathway in Human Pancreatic Cancer, Clinical Cancer Research, 2007, 2151-2157, 13.

Ohigashi et al., Clinical Significance of Programmed Death-1 Ligand-1 and Programmed Death-1 Ligand-2 Expression in Human Esophageal Cancer, Clinical Cancer Research, 2005, 2947-2953, 11.

Sharpe et al., The function of programmed cell death 1 and its ligands in regulating autoimmunity and infection, Nature Immunology, 2007, 239-245, 8.

Shimauchi et al., Augmented expression of programmed death-1 in both neoplastic and non-neoplastic CD4+ T-cells in adult T-cell leukemia/lymphoma, Int. J. Cancer, 2007, 2585-2590, 121.

Thompson et al., PD-1 Is Expressed by Tumor-Infiltrating Immune Cells and Is Associated with Poor Outcome for Patients with Renal Cell Carcinoma, Clinical Cancer Research, 2007, 1757-1761, 15.

Thompson et al., Significance of B7-H1 Overexpression in Kidney Cancer, Cancer, 2006, 206-211, 5.

Written Opinion of PCT/US15/64445 dated May 17, 2016.

Yang et al., PD-L1: PD-1 Interaction Contributes to the Functional Suppression of T-Cell Responses to Human Uveal Melanoma Cells In Vitro, Invest Ophthalmol Vis Sci, 2008, 2518-2525, 49(6).

Zou et al., Regularization and variable selection via the elastic net, J. R. Statist. Soc. B, 2005, 301-320, 67(2).

N. Lal, An immunogenomic stratification of colorectal cancer: Implications for development of targeted immunotherapy, Oncolmmunology, Apr. 2, 2015, pp. 1-9, vol. 4, No. 3.

* cited by examiner

SYSTEM AND METHODS FOR DERIVING GENE SIGNATURE BIOMARKERS OF RESPONSE TO PD-1 ANTAGONISTS

CROSS-REFERENCE TO RELATED APPLICATIONS

This application is a § 371 National Stage Application of PCT/US2015/064445, international filing date of Dec. 8, 2015, which claims the benefit of U.S. Provisional Application Ser. No. 62/089,538, filed Dec. 9, 2014, and claims the benefit of U.S. Provisional Application Ser. No. 62/160,284, filed May 12, 2015.

FIELD OF THE INVENTION

The present invention relates generally to the treatment of cancer with antagonists of Programmed Death 1 (PD-1). In particular, the invention relates to defining pre-treatment gene signatures that are predictive of response to PD-1 antagonists and to the use of such gene signatures as biomarkers to identify patients who are most likely to respond to therapy with a PD-1 antagonist.

BACKGROUND OF THE INVENTION

PD-1 is recognized as an important molecule in immune regulation and the maintenance of peripheral tolerance. PD-1 is moderately expressed on naive T, B and NKT cells and up-regulated by T/B cell receptor signaling on lymphocytes, monocytes and myeloid cells (1).

Two known ligands for PD-1 are PD-L1 (B7-H1) and PD-L2 (B7-DC), which are expressed in human cancers arising in various tissues. In large sample sets of e.g. ovarian, renal, colorectal, pancreatic, liver cancers and melanoma, it was shown that PD-L1 expression correlated with poor prognosis and reduced overall survival irrespective of subsequent treatment (2-13). Similarly, PD-1 expression on tumor infiltrating lymphocytes was found to mark dysfunctional T cells in breast cancer and melanoma (14-15) and to correlate with poor prognosis in renal cancer (16). Thus, it has been proposed that PD-L1 expressing tumor cells interact with PD-1 expressing T cells to attenuate T cell activation and evasion of immune surveillance, thereby contributing to an impaired immune response against the tumor.

Several monoclonal antibodies (mAbs) that antagonize PD-1 activity by inhibiting the interaction between PD-1 and one or both of PD-L1 and PD-L2 are in clinical development for treating cancer. These include nivolumab and pembrolizumab, which bind to PD-1, and MPDL3280A, which binds to PD-L1. While clinical studies with these mAbs have produced durable anti-tumor responses in some cancer types, a significant number of patients failed to exhibit an anti-tumor response. Thus, a need exists for diagnostic tools to identify which cancer patients are most likely to achieve a clinical benefit to treatment with a PD-1 antagonist.

An active area in cancer research is the identification of intratumoral expression patterns for sets of genes, commonly referred to as gene signatures or molecular signatures, which are characteristic of particular types or subtypes of cancer, and which may be associated with clinical outcomes.

SUMMARY OF THE INVENTION

The system and methods of the present invention are based on a combination of a clinical response gene set and a normalization gene set, referred to herein as a "gene expression platform", which the inventors designed as a tool for deriving different sets of genes having pre-treatment intratumoral RNA expression levels ("gene signatures") that are correlated with an anti-tumor response to a PD-1 antagonist for multiple tumor types. The inventors also contemplate that this gene expression platform will be useful to derive a scoring algorithm that weights the relative contribution of individual genes in a signature to a correlation to generate an arithmetic composite of normalized RNA levels of all of the genes in the gene signature, referred to herein as a "gene signature score". By comparing gene signature scores and anti-tumor responses obtained for a cohort of patients with the same tumor type of interest and treated with a PD-1 antagonist, the inventors contemplate that a cut-off score may be selected that divides patients according to having a higher or lower probability of achieving an anti-tumor response to the PD-1 antagonist. A predictive signature score for a particular tumor type is referred to herein as a gene signature biomarker. Patients whose tumor tests positive for a gene signature biomarker derived according to the present invention are more likely to benefit from therapy with a PD-1 antagonist than patients whose tumors test negative for the gene signature biomarker.

Thus, in a first aspect, the invention provides a method of deriving a gene signature biomarker that is predictive of an anti-tumor response to a PD-1 antagonist for at least one tumor type of interest. The method comprises: (a) obtaining a pre-treatment tumor sample from each patient in a patient cohort diagnosed with the tumor type; (b) obtaining, for each patient in the cohort, an anti-tumor response value following treatment with the PD-1 antagonist; (c) measuring the raw RNA levels in each tumor sample for each gene in a gene expression platform, wherein the gene expression platform comprises a set of clinical response genes and a set of normalization genes; (d) normalizing, for each tumor sample, each of the measured raw RNA levels for the clinical response genes using the measured RNA levels of the normalization genes; (e) weighting, for each tumor sample and each gene in a gene signature of interest, the normalized RNA expression levels using a pre-defined multiplication coefficient for that gene; (f) adding, for each tumor sample, the weighted RNA expression levels to generate a gene signature score; and (g) comparing the gene signature scores for all of the tumor samples and anti-tumor response values for all of the patients in the cohort to select a cut-off for the gene signature score that divides the patient cohort to meet a target biomarker clinical utility criterion. In an embodiment, the method further comprises designating any tumor sample of the tumor type that has a gene signature score that is equal to or greater than the selected cut-off as biomarker positive and designating any tumor sample of the tumor type that has a gene signature score that is below the selected cut-off as biomarker negative.

The inventors contemplate that gene signature biomarkers derived using the above method of the invention would be useful in a variety of clinical research and patient treatment settings, such as, for example, to selectively enroll only biomarker positive patients into a clinical trial of the PD-1 antagonist, to stratify the analysis of a clinical trial of the PD-1 antagonist based on biomarker positive or negative status, or to determine eligibility of a patient for treatment with the PD-1 antagonist.

Thus, in a second aspect, the invention provides a method for testing a tumor sample removed from a patient diagnosed with a particular tumor type for the presence or absence of a gene signature biomarker of anti-tumor response of the tumor type to a PD-1 antagonist. The method comprises: (a)

measuring the raw RNA level in the tumor sample for each gene in a gene expression platform, wherein the gene expression platform comprises a set of clinical response genes and a set of normalization genes; (b) normalizing the measured raw RNA level for each clinical response gene in a pre-defined gene signature for the tumor type using the measured RNA levels of the normalization genes; (c) weighting each normalized RNA value using a pre-defined multiplication co-efficient; (d) adding the weighted RNA expression levels to generate a gene signature score; (e) comparing the generated score to a reference score for the gene signature and tumor type; and (f) classifying the tumor sample as biomarker positive or biomarker negative; wherein if the generated score is equal to or greater than the reference score, then the tumor sample is classified as biomarker positive, and if the generated score is less than the reference score, then the tumor sample is classified as biomarker negative.

In a third aspect, the invention provides a system for testing a tumor sample removed from a patient diagnosed with a particular tumor type for the presence or absence of a gene signature biomarker of anti-tumor response of the tumor type to a PD-1 antagonist. The system comprises (i) a sample analyzer for measuring raw RNA expression levels of each gene in a gene expression platform, wherein the gene expression platform consists of a set of clinical response genes and a set of normalization genes, and (ii) a computer program for receiving and analyzing the measured RNA expression levels to (a) normalize the measured raw RNA level for each clinical response gene in a pre-defined gene signature for the tumor type using the measured RNA levels of the normalization genes; (b) weight each normalized RNA value using a pre-defined multiplication co-efficient; (c) add the weighted RNA expression levels to generate a gene signature score; (d) compare the generated score to a reference score for the gene signature and tumor type; and (e) classify the tumor sample as biomarker positive or biomarker negative, wherein if the generated score is equal to or greater than the reference score, then the tumor sample is classified as biomarker positive, and if the generated score is less than the reference score, then the tumor sample is classified as biomarker negative.

In each of the above aspects of the invention, the clinical response genes in the gene expression platform are (a) individually correlated with an anti-tumor response to a PD-1 antagonist in more than one tumor type and (b) collectively generate a covariance pattern that is substantially similar in each of the tumor types. A first subset of genes in the clinical response gene set exhibit intratumoral RNA levels that are positively correlated with the anti-tumor response while intratumoral RNA levels for a second subset of genes in the clinical response gene set are negatively correlated with the anti-tumor response. In an embodiment, the clinical response gene set comprises about 57 genes, the first subset comprises about 51 genes and the second subset comprises about 6 genes. In some embodiments of any of the above aspects of the invention, the gene expression platform comprises the 57 genes listed in Tables 1A and 1B.

In some embodiments of any of the above aspects of the invention, the set of normalization genes in the gene expression platform comprises genes which individually exhibit intratumoral RNA levels of low variance across multiple samples of the different tumor types and collectively exhibit a range of intratumoral RNA levels that spans the range of intratumoral expression levels of the clinical response genes in the different tumor types. In some embodiments, the normalization gene set comprises 10 to 12 genes. In an embodiment of any of the above aspects of the invention, the gene expression platform comprises the 11 normalization genes listed in Table 1C below.

TABLE 1

Exemplary Gene Expression Platform

| Gene Symbol | Accession No. | Exemplary Target Region |
|---|---|---|
| Table 1A. Clinical Response Gene Set - Positively Correlated Genes | | |
| B2M | NM_004048.2 | 235-335 |
| CASP8 | NM_001228.4 | 301-401 |
| CCL5 | NM_002985.2 | 280-380 |
| CCR5 | NM_000579.1 | 2730-2830 |
| CD1D | NM_001766.3 | 1428-1528 |
| CD2 | NM_001767.3 | 687-787 |
| CD27 | NM_001242.4 | 330-430 |
| CD274 | NM_014143.3 | 1245-1345 |
| CD3D | NM_000732.4 | 110-210 |
| CD3E | NM_000733.2 | 75-175 |
| CD3G | NM_000073.2 | 515-615 |
| CD4 | NM_000616.4 | 975-1075 |
| CD74 | NM_001025159.1 | 964-1064 |
| CD8A | NM_001768.5 | 1320-1420 |
| CIITA | NM_000246.3 | 470-570 |
| CMKLR1 | NM_004072.1 | 770-870 |
| CXCL10 | NM_001565.1 | 40-140 |
| CXCL13 | NM_006419.2 | 210-310 |
| CXCL9 | NM_002416.1 | 1975-2075 |
| CXCR6 | NM_006564.1 | 95-195 |
| GRAP2 | NM_004810.2 | 232-332 |
| GZMB | NM_004131.3 | 540-640 |
| GZMK | NM_002104.2 | 700-800 |
| HLA-DPB1 | NM_002121.4 | 931-1031 |
| HLA-DQA1 | NM_002122.3 | 261-361 |
| HLA-DRA | NM_019111.3 | 335-435 |
| HLA-DRB1 | NM_002124.1 | 985-1085 |
| HLA-E | NM_005516.4 | 1204-1304 |
| IDO1 | NM_002164.3 | 50-150 |
| IFNG | NM_000619.2 | 970-1070 |
| IKZF3 | NM_183232.2 | 1176-1276 |
| IL10RA | NM_001558.2 | 150-250 |
| IL2RB | NM_000878.2 | 1980-2080 |
| IL2RG | NM_000206.1 | 595-695 |
| IRF8 | NM_002163.2 | 253-353 |
| LAG3 | NM_002286.5 | 1735-1835 |
| LCK | NM_005356.2 | 1260-1360 |
| LILRB1 | NM_001081637.1 | 2332-2432 |
| NKG7 | NM_005601.3 | 632-732 |
| P2RY8 | NM_178129.3 | 425-525 |
| PDCD1LG2 | NM_025239.3 | 235-335 |
| PSMB10 | NM_002801.2 | 221-321 |
| PTPRCAP | NM_005608.2 | 668-768 |
| SAMHD1 | NM_015474.2 | 640-740 |
| SLAMF7 | NM_021181.3 | 215-315 |
| STAT1 | NM_007315.2 | 205-305 |
| TAGAP | NM_054114.3 | 169-269 |
| TIGIT | NM_173799.2 | 1968-2068 |
| TNFRSF14 | NM_003820.2 | 916-1016 |
| TNFSF13B | NM_006573.4 | 1430-1530 |
| ZAP70 | NM_001079.3 | 1175-1275 |
| Table 1B. Clinical Response Gene Set - Negatively Correlated Genes | | |
| CD276 | NM_001024736.1 | 2120-2220 |
| CTAG1B | NM_001327.2 | 285-385 |
| DSG2 | NM_001943.3 | 235-335 |
| EGFR | NM_201282.1 | 360-460 |
| SLC2A1 | NM_006516.2 | 2500-2600 |
| TSLP | NM_033035.4 | 899-999 |
| Table 1C. Normalization Gene Set | | |
| ABCF1 | NM_001090.2 | 850-950 |
| C14ORF102 | NM_017970.3 | 3236-3336 |
| G6PD | NM_000402.2 | 1155-1255 |
| OAZ1 | NM_004152.2 | 313-413 |
| POLR2A | NM_000937.2 | 3775-3875 |
| SDHA | NM_004168.1 | 230-330 |
| STK11IP | NM_052902.2 | 565-665 |
| TBC1D10B | NM_015527.3 | 2915-3015 |

TABLE 1-continued

Exemplary Gene Expression Platform

| Gene Symbol | Accession No. | Exemplary Target Region |
|---|---|---|
| TBP | NM_001172085.1 | 587-687 |
| UBB | NM_018955.2 | 795-895 |
| ZBTB34 | NM_001099270.1 | 406-506 |

The inventors have identified the specific gene signatures shown in Table 2 below, which are represented in the clinical response gene and are correlated with response to pembrolizumab across multiple tumor types. Since there are several genes in common to each of these gene signatures, the inventors propose that gene signature biomarkers that are predictive of response to a PD-1 antagonist may be derived for any of these signatures, as well as for other gene signatures comprising any combination of 2 to 57 of the clinical response genes in Table 1.

TABLE 2

| | 6-Gene IFNg Signature | 5-Gene IFNg-induced Signature | 5-Gene PD-L1 Signature | 3-Gene MHCII Signature | 18-Gene Expanded Immune Signature | 13-Gene TCR Signaling Signature | 7-Gene MIPFS Signature | 14 Gene Up-Down Signature | 18 Gene Up-Down Signature |
|---|---|---|---|---|---|---|---|---|---|
| 1 | IDO1 | IDO1 | CD274 | HLA-DRA | CD3D | CD27 | CD27 | CCL5 | CCL5 |
| 2 | CXCL10 | CXCL10 | PDCD1LG2 | HLA-DPB1 | IDO1 | TIGIT | CD3D | CD27 | CD27 |
| 3 | CXCL9 | CXCL9 | STAT1 | STAT1 | CIITA | CD8a | CD74 | CD274 | CD274 |
| 4 | HLA-DRA | HLA-DRA | LAG3 | | CD3E | CD3G | CXCL9 | CD276 | CD276 |
| 5 | STAT1 | STAT1 | CXCL10 | | CCL5 | CD3D | HLA-DRB1 | CXCL9 | CD8A |
| 6 | IFNG | | | | GZMK | GRAP2 | IDO1 | DSG2 | CMKLR1 |
| 7 | | | | | CD2 | LCK | SAMHD1 | HLA.DRB1 | CXCL9 |
| 8 | | | | | HLA-DRA | PTPRCAP | | IDO1 | CXCR6 |
| 9 | | | | | CXCL13 | CD4 | | LAG3 | HLA.DQA1 |
| 10 | | | | | IL2RG | CCL5 | | NKG7 | HLA.DRB1 |
| 11 | | | | | NKG7 | IL2RB | | SLAMF7 | HLA.E |
| 12 | | | | | HLA-E | IKZF3 | | STAT1 | IDO1 |
| 13 | | | | | CXCR6 | CD74 | | TIGIT | LAG3 |
| 14 | | | | | LAG3 | | | TSLP | NKG7 |
| 15 | | | | | TAGAP | | | | PDCD1LG2 |
| 16 | | | | | CXCL10 | | | | PSMB10 |
| 17 | | | | | STAT1 | | | | STAT1 |
| 18 | | | | | GZMB | | | | TIGIT |

Thus, in some embodiments, the gene signature being evaluated in a method or system of the invention may comprise any combination of at least two of the clinical response genes in Table 1, and may comprise 3, 4, 5, 6, 7, 13 or 18, or any number between 2 and 57 of the clinical response genes in Table 1. In some embodiments, the gene signature is selected from the group consisting of the 57 clinical response genes in Tables 1A and 1B, the 51 clinical response genes in Table 1A and the gene signatures listed in Table 2. In some embodiments, the gene signature is the 18 Gene Up-Down Signature shown in Table 2.

Anti-tumor response values used in any of the above aspects and embodiments of the invention may be for any quantitative or qualitative measurement of an anti-tumor response in an individual patient, or may be the rate of the anti-tumor response that has been observed in a patient cohort. The anti-tumor response value may be obtained during or following any period of treatment of the cohort with the PD-1 antagonist. In another embodiment, the anti-tumor response value is an objective value, such as partial response, complete response, or best overall response as measured by RECIST 1.1 or irRC. In an embodiment, the anti-tumor response value is the duration of an anti-tumor response, e.g., the number of days, months or years that a patient has progression free survival, disease free survival or some other ongoing anti-tumor response. In another embodiment, the anti-tumor response value is a response rate for a patient cohort treated with the PD-1 antagonist, such as objective response rate (ORR) or median overall survival. In some embodiments, anti-tumor response values (individual values or cohort response rates) are obtained after at least 2, 3, 4, 5, 6, 7, 8, 9 or more doses of the PD-1 antagonist. In other embodiments, the anti-tumor response value is for a sustained anti-tumor response, which is assessed at any time following the last dose of the PD-1 antagonist on a patient by patient basis, e.g., at 3, 6, 9, 12, 15, 18, 21 or 24 months after administration of the last dose.

The inventors contemplate that the above methods and system may be used to derive gene signature biomarkers for a variety of PD-1 antagonists and tumor types. In some embodiments, the PD-1 antagonist is nivolumab or pembrolizumab. The patient cohort may be treated with the PD-1 antagonist as monotherapy or as part of a combination therapy that includes one or more other cancer treatments. In some embodiments, the tumor type is bladder cancer, colorectal cancer, gastric cancer, head and neck cancer, melanoma, non-small cell lung cancer, ovarian cancer, prostate cancer or renal cancer. In an embodiment, the PD-1 antagonist is pembrolizumab and the tumor type is anal cancer, biliary cancer, bladder cancer, colorectal cancer, esophageal cancer, gastric cancer, head and neck cancer, melanoma or ovarian cancer.

In some embodiments of method and system of the invention, normalized RNA expression levels of the clinical response genes for each sample are obtained by performing a log(10) transformation of the measured raw RNA levels for each clinical response gene in Table 1 and each normalization gene in Table 1, calculating an arithmetic mean of the log 10 transformed RNA levels of the normalization genes, and subtracting the calculated mean from the log 10 transformed RNA levels for each clinical response gene in Table 1.

In some embodiments that employ any of the specific gene signatures in Table 2, the measured RNA values are obtained by performing a log(10) transformation of the measured raw RNA levels for each clinical response gene in the signature and for a set of normalization genes, calculating an arithmetic mean of the log 10 transformed RNA levels of the normalization genes, and subtracting the calculated mean from the log 10 transformed RNA levels for each clinical response gene. In some embodiments, the set of normalization genes comprises the normalization genes listed in Table 1C. In an embodiment, the gene signature is the 5-Gene IFNg-induced Signature or the 7-Gene MIPFS Signature set forth in Table 2. In an embodiment, the gene signature is the 18-Gene Up-Down Signature set forth in Table 2 and the set of normalization genes consists of the 10 genes listed in Table 1C.

In an embodiment, each gene in a gene signature of interest (i.e., a pre-defined gene signature for a particular tumor type) is assumed to contribute equally to the tumor response correlation, and thus each gene is weighted equally. Thus, the pre-defined multiplication coefficient for each gene in that gene signature is 1, and the normalized RNA expression scores for the genes in the gene signature may be combined by straight addition or by calculating the arithmetic mean.

In another embodiment, the degree to which different genes in a particular gene signature contribute to the anti-tumor response correlation varies and the coefficients to weight these contribution differences have been pre-defined by applying a multivariate statistical model to the anti-tumor response values and normalized gene expression levels determined for the patient cohort. Table 3 below sets forth exemplary sets of weighting coefficients for use in calculating signature scores for several gene signatures of the invention. The gene signature identified in Table 3A consists of the 57 Clinical Response Genes in Table 1 and the gene signatures in Table 3B are the 14-Gene Up-Down and 18-Gene Up-Down Signatures set forth in Table 2.

TABLE 3A

Exemplary Scoring Weight Sets for a 57-Gene Up-Down Signature

| | Scoring Weights | | | | | |
|---|---|---|---|---|---|---|
| Gene | Set 1.1 | Set 1.2 | Set 2.1 | Set 2.2 | Set 2.3 | Set 2.4 |
| B2M | 0.011382 | 0.024936 | 0.018302 | 0.036653 | 0 | 0 |
| CASP8 | 0.265228 | 0.117023 | −0.00793 | 0.013772 | 0 | 0 |
| CCL5 | 0.062629 | 0.033611 | 0.047293 | 0.047908 | 0.01828 | 0.008346 |
| CCR5 | 0.128025 | 0.016349 | 0.015352 | 0.023896 | 0 | 0 |
| CD1D | 0.167559 | 0.083125 | −0.00614 | 0.056356 | 0 | 0 |
| CD2 | 0.045129 | 0.061991 | 0.008459 | 0.040452 | 0 | 0 |
| CD27 | 0.165679 | 0.077354 | 0.060905 | 0.074524 | 0.026115 | 0.072293 |
| CD274 | −0.02972 | −0.00707 | 0.06064 | 0.068105 | 0.003785 | 0.042853 |
| CD276 | −0.76078 | −0.09354 | −0.31072 | −0.13562 | −0.30985 | −0.0239 |
| CD3D | 0.018391 | 0.012381 | 0.03676 | 0.03169 | 0 | 0 |
| CD3E | −0.10144 | −0.01782 | −0.03552 | −0.01259 | 0 | 0 |
| CD3G | −0.01041 | −0.00352 | −0.00427 | 0.015561 | 0 | 0 |
| CD4 | 0.022836 | −0.00129 | −0.03541 | −0.02984 | 0 | 0 |
| CD74 | 0.178222 | 0.080644 | 0.043171 | −0.00578 | 0 | 0 |
| CD8A | 0.03988 | 0.007395 | 0.018698 | 0.058196 | 0 | 0.031021 |
| CIITA | 0.082422 | 0.025467 | 0.007537 | −0.05867 | 0 | 0 |
| CMKLR1 | 0.133949 | 0.143101 | 0.015161 | 0.145646 | 0 | 0.151253 |
| CTAG1B | −0.06995 | −0.01318 | −0.03191 | −0.00857 | 0 | 0 |
| CXCL10 | 0.034214 | 0.02539 | 0.016961 | 0.022264 | 0 | 0 |
| CXCL13 | −0.03437 | −0.00266 | 0.000212 | 0.000177 | 0 | 0 |
| CXCL9 | 0.044157 | 0.02995 | 0.070541 | 0.066721 | 0.082479 | 0.074135 |
| CXCR6 | −0.02213 | 0.011161 | 0.042193 | 0.047959 | 0 | 0.004313 |
| DSG2 | −0.13793 | −0.01587 | −0.09201 | −0.05557 | −0.00274 | 0 |
| EGFR | −0.09487 | 0.019951 | −0.02788 | 0.03066 | 0 | 0 |
| GRAP2 | −0.04299 | 0.016299 | −0.02691 | 0.016182 | 0 | 0 |
| GZMB | −0.14999 | −0.03366 | −0.00108 | 0.003182 | 0 | 0 |
| GZMK | 0.029626 | −0.01755 | 0.030039 | 0.017541 | 0 | 0 |
| HLA.DPB1 | 0.064174 | 0.022285 | 0.036324 | 0.025171 | 0 | 0 |
| HLA.DQA1 | 0.130082 | 0.037396 | 0.028595 | 0.033192 | 0 | 0.020091 |
| HLA.DRA | 0.145429 | 0.070683 | 0.03516 | 0.014876 | 0 | 0 |
| HLA.DRB1 | 0.250074 | 0.115735 | 0.059579 | 0.072856 | 0.034058 | 0.058806 |
| HLA.E | 0.163272 | 0.126027 | −0.00391 | 0.102635 | 0 | 0.07175 |
| IDO1 | 0.045061 | 0.065179 | 0.058149 | 0.064514 | 0.060534 | 0.060679 |
| IFNG | −0.1053 | 0.012953 | −0.02794 | 0.028571 | 0 | 0 |
| IKZF3 | −0.09116 | −0.03226 | −0.02025 | −0.03985 | 0 | 0 |
| IL10RA | 0.064457 | 0.050129 | 0.01675 | 0.005515 | 0 | 0 |
| IL2RB | −0.1838 | −0.05146 | −0.01606 | −0.02598 | 0 | 0 |
| IL2RG | −0.03321 | 0.036433 | 0.002905 | 0.027405 | 0 | 0 |
| IRF8 | 0.007075 | 0.019088 | −0.0404 | −0.02196 | 0 | 0 |
| LAG3 | 0.065194 | 0.072767 | 0.09483 | 0.120548 | 0.07897 | 0.123895 |
| LCK | −0.10023 | −0.00053 | −0.04718 | −0.02763 | 0 | 0 |
| LILRB1 | 0.000354 | 0.0449 | −0.04635 | −0.02986 | 0 | 0 |
| NKG7 | 0.03507 | 0.024692 | 0.061331 | 0.078649 | 0.02502 | 0.075524 |
| P2RY8 | 0.059388 | 0.042677 | −0.00014 | 0.009614 | 0 | 0 |
| PDCD1LG2 | 0.124489 | 0.025347 | 0.050804 | 0.057426 | 0 | 0.003734 |
| PSMB10 | 0.037785 | 0.117496 | 0.042826 | 0.074887 | 0 | 0.032999 |
| PTPRCAP | −0.06155 | −0.01755 | −0.01397 | −0.0278 | 0 | 0 |
| SAMHD1 | −0.15245 | 0.022386 | −0.10801 | −0.09063 | 0 | 0 |
| SLAMF7 | 0.118585 | 0.030654 | 0.044198 | 0.03849 | 0.00028 | 0 |
| SLC2A1 | −0.07881 | −0.06001 | −0.02308 | −0.04061 | 0 | 0 |
| STAT1 | 0.18251 | 0.166322 | 0.106029 | 0.201166 | 0.067425 | 0.250229 |
| TAGAP | −0.04634 | 0.000536 | −0.0462 | −0.02365 | 0 | 0 |
| TIGIT | 0.0486 | 0.058542 | 0.084837 | 0.089709 | 0.058121 | 0.084767 |

TABLE 3A-continued

Exemplary Scoring Weight Sets for a 57-Gene Up-Down Signature

| | Scoring Weights | | | | | |
|---|---|---|---|---|---|---|
| Gene | Set 1.1 | Set 1.2 | Set 2.1 | Set 2.2 | Set 2.3 | Set 2.4 |
| TNFRSF14 | 0.111087 | 0.004593 | 0.05374 | −0.02338 | 0 | 0 |
| TNFSF13B | 0.263637 | 0.106224 | −0.00983 | 0.010906 | 0 | 0 |
| TSLP | −0.11095 | −0.04091 | −0.07776 | −0.04751 | −0.00057 | 0 |
| ZAP70 | 0.036773 | 0.043754 | −0.02693 | −0.04663 | 0 | 0 |

TABLE 3B

Exemplary Scoring Weight Sets for Up-Down Signatures Derived from Table 1

| Gene | 14-Gene Up-Down Signature[a] | 18-Gene Up-Down Signature[a] |
|---|---|---|
| CCL5 | 0.01828 | 0.008346 |
| CD27 | 0.026115 | 0.072293 |
| CD274 | 0.003785 | 0.042853 |
| CD276 | −0.30985 | −0.0239 |
| CD8A | N/A | 0.031021 |
| CMKLR1 | N/A | 0.151253 |
| CXCL9 | 0.082479 | 0.074135 |
| CXCR6 | N/A | 0.004313 |
| DSG2 | −0.00274 | N/A |
| HLA.DQA1 | N/A | 0.020091 |
| HLA.DRB1 | 0.034058 | 0.058806 |
| HLA.E | N/A | 0.07175 |
| IDO1 | 0.060534 | 0.060679 |
| LAG3 | 0.07897 | 0.123895 |
| NKG7 | 0.02502 | 0.075524 |
| PDCD1LG2 | N/A | 0.003734 |
| PSMB10 | N/A | 0.032999 |
| SLAMF7 | 0.00028 | N/A |
| STAT1 | 0.067425 | 0.250229 |
| TIGIT | 0.058121 | 0.084767 |
| TSLP | −0.00057 | N/A |

[a]N/A means the indicated gene is not considered to be part of the signature.

Thus, in an embodiment, generating a signature score for a tumor sample removed from a patient comprises (i) multiplying the normalized RNA value obtained for each gene in a gene signature by the coefficient for that gene from a set of scoring weights to generate a weighted RNA value for each of the genes in the signature and (ii) adding the weighted RNA values to produce the signature score for the tumor sample, wherein when the gene signature consists of the 57 Up-Down Signature in Table 3A, then the scoring weight set is selected from the group consisting of Set 1.1, Set 1.2, Set 2.1, Set 2.2, Set 2.3 and Set 2.4 and when the gene signature consists of the 14-Gene Up-Down Signature in Table 3B, then the scoring weight set consists of the weights in the second column of Table 3B and when the gene signature consists of the 18-Gene Up-Down Signature in Table 3B, the scoring weight set consists of the weights in the third column of Table 3B.

In some embodiments that employ one of the scoring weight sets in Table 3A or 3B to generate signature scores, the normalized RNA values are obtained by performing a log(10) transformation of the measured raw RNA levels for each clinical response gene in the signature and for each normalization gene in Table 1C, calculating an arithmetic mean of the log 10 transformed RNA levels of the normalization genes, and subtracting the calculated mean from the log 10 transformed RNA levels for each clinical response gene. In an embodiment, the target biomarker utility criterion that is met by the selected cut-off score is that the majority of responder patients in the cohort have a gene signature score equal to or above the cut-off while the majority of non-responder patients had a gene signature below the cut-off. In another embodiment, the target biomarker utility criterion is that at least 20%, 40%, 60% or 80% of the responder patients in the patient cohort have a gene signature score that is equal to or greater than the selected cut-off score. In another embodiment, the cut-off score is selected to satisfy a target biomarker utility criterion of at least 80%, 85%, 90% or 95%, or near 100% of the non-responder patients in the cohort having gene signature scores below the cut-off score. In another embodiment, the target biomarker utility criterion is a positive predictive value (PPV) for the selected cut-off of at least 25%, 30%, 35% or higher and a negative predictive value (NPV) of at least 90%, 93%, 96% or higher when applied to separate patients in the patient cohort.

In an embodiment, the PD-1 antagonist is pembrolizumab or nivolumab, the gene signature consists of at least five of the clinical response genes listed in Table 1.

In some embodiments, the gene signature is selected from the gene signatures listed in Table 2, and the patient has been diagnosed with bladder cancer, gastric cancer, head and neck cancer or melanoma.

In some embodiments, the PD-1 antagonist is pembrolizumab, the gene signature is the IFNg, PD-L1, Expanded Immune or TCR Signaling Signatures shown in Table 2, and the patient has been diagnosed with bladder cancer, gastric cancer, head and neck cancer or melanoma.

In some embodiments, the reference score for the gene signature has been determined to divide at least the majority of a group of responders to the PD-1 antagonist from at least the majority of non-responders to the PD-1 antagonist. Thus, a patient whose tumor sample is classified as biomarker positive is more likely to respond, or to achieve a better response, to the PD-1 antagonist than a patient whose tumor sample is classified as biomarker negative.

In yet another aspect, the invention provides a kit useful for assaying a tumor sample to obtain normalized RNA expression scores for any of the gene signatures described herein.

In one embodiment, the kit comprises a set of hybridization probes capable of specifically binding to a transcript expressed by each of the genes in Table 1 and a set of reagents designed to quantify the number of specific hybridization complexes formed with each hybridization probe. In an embodiment, each hybridization probe in the set has a unique detectable label and is designed to specifically hybridize to a target sequence that is unique to one of the clinical response genes and normalization genes, thereby enabling detection of transcripts for all of the Table 1 genes in a tumor sample in a single hybridization reaction. In an embodiment, a kit of the invention may also comprise at least one control tumor sample which may be assayed for expression of the clinical response and normalization genes in the same manner as test tumor samples.

In another embodiment, the kit comprises (1) a set of hybridization probes capable of specifically binding to a transcript expressed by each of the genes in a gene signature selected from the groups of gene signatures shown in Table 2 and by each of the normalization genes listed in Table 1 and (2) a set of reagents designed to quantify the number of specific hybridization complexes formed with each hybridization probe.

In a still further aspect, the invention provides a method for treating a patient having a tumor which comprises determining if the tumor is positive or negative for a gene signature biomarker and administering to the subject a PD-1 antagonist if the tumor is positive for the biomarker and administering to the subject a cancer treatment that does not include a PD-1 antagonist if the tumor is negative for the biomarker, wherein the gene signature biomarker is for a gene signature that comprises at least two of the clinical response genes in Table 1. In an embodiment the gene signature is selected from the gene signatures listed in Table 2.

In a still further aspect, the invention provides a pharmaceutical composition comprising a PD-1 antagonist for use in a subject who has a tumor that tests positive for a gene signature biomarker, wherein the gene signature biomarker is for a gene signature selected from the gene signatures listed in Table 2.

Yet another aspect of the invention is a drug product which comprises a pharmaceutical composition and prescribing information. The pharmaceutical composition comprises a PD-1 antagonist and at least one pharmaceutically acceptable excipient. The prescribing information states that the pharmaceutical composition is indicated for use in a subject who has a tumor that tests positive for a gene signature biomarker, wherein the gene signature biomarker is for a gene signature selected from the gene signatures listed in Table 2.

DETAILED DESCRIPTION

I. Abbreviations

Figure 1:
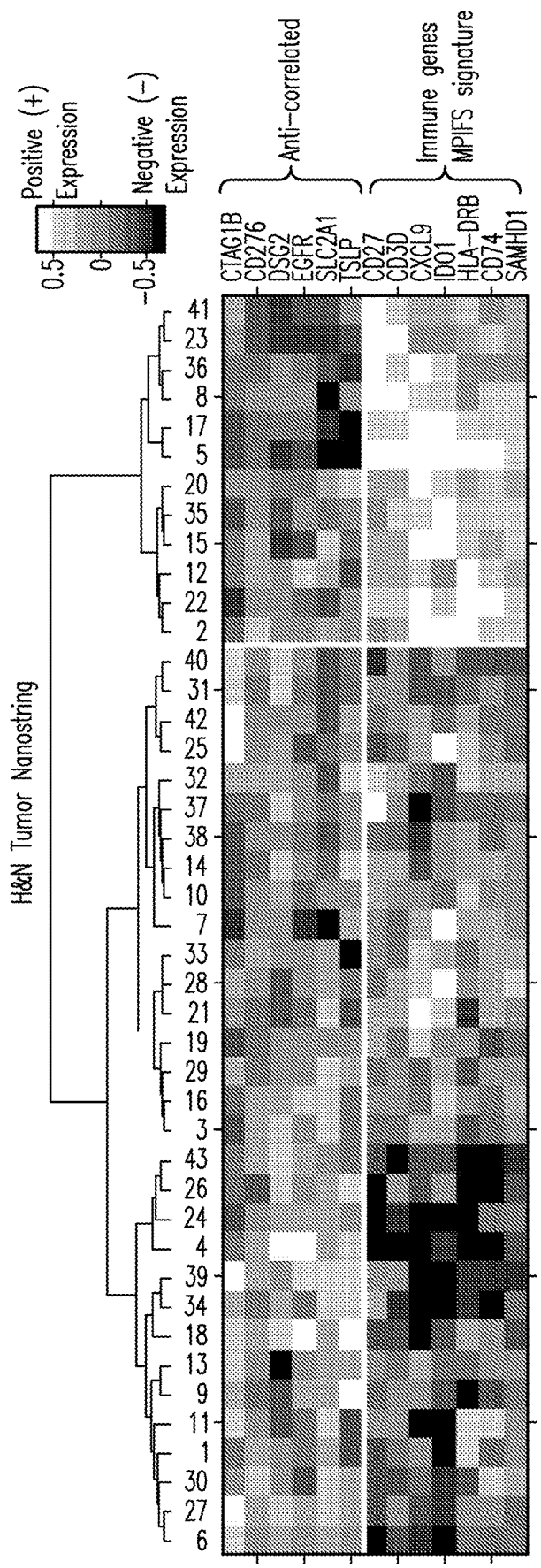
FIG. 1 shows the results of an unsupervised clustering analysis across multiple head & neck tumor samples of the MIPFS gene signature listed in Table 2 with the 6-gene anti-correlated gene subset listed in Table 1B.
Figure 2A:
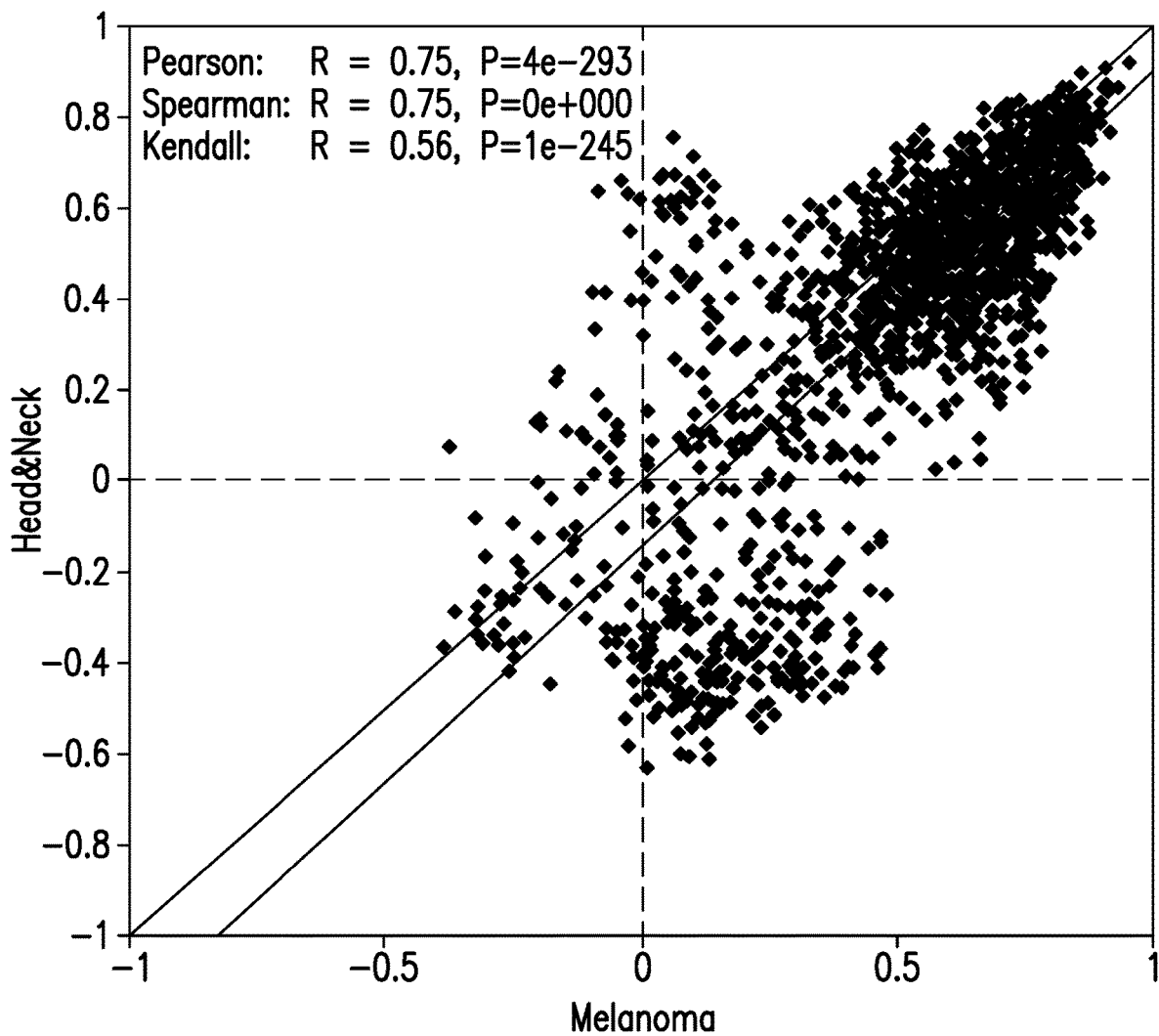
FIGS. 2A, 2B, 2C, 2D, 2E, 2F, 2G, 2H and 2I show scatter plots of pairwise correlations of normalized RNA expression levels for some or all of the 57 clinical response genes in Table 1 in multiple melanoma tumor samples versus multiple tumor samples of the following tumor types: head & neck cancer (FIG. 2A), bladder cancer (FIG. 2B), gastric cancer (FIG. 2C), NSCLC (FIG. 2D), colorectal cancer (FIG. 2E), renal cancer (FIG. 2F), prostate cancer (FIG. 2G), ovarian cancer (FIG. 2H), and triple negative breast cancer (FIG. 2I).
Figure 2B:
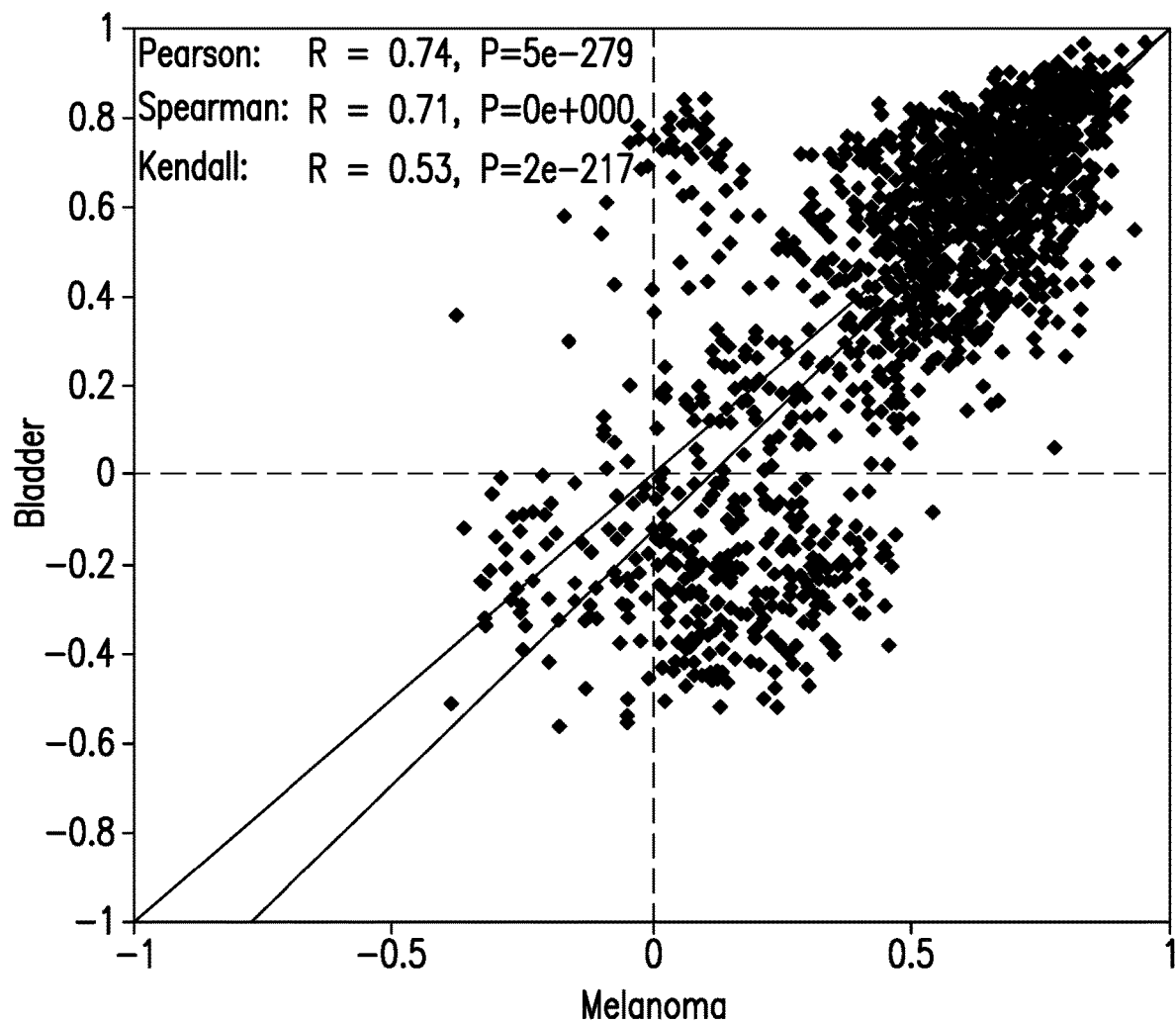
Figure 2C:
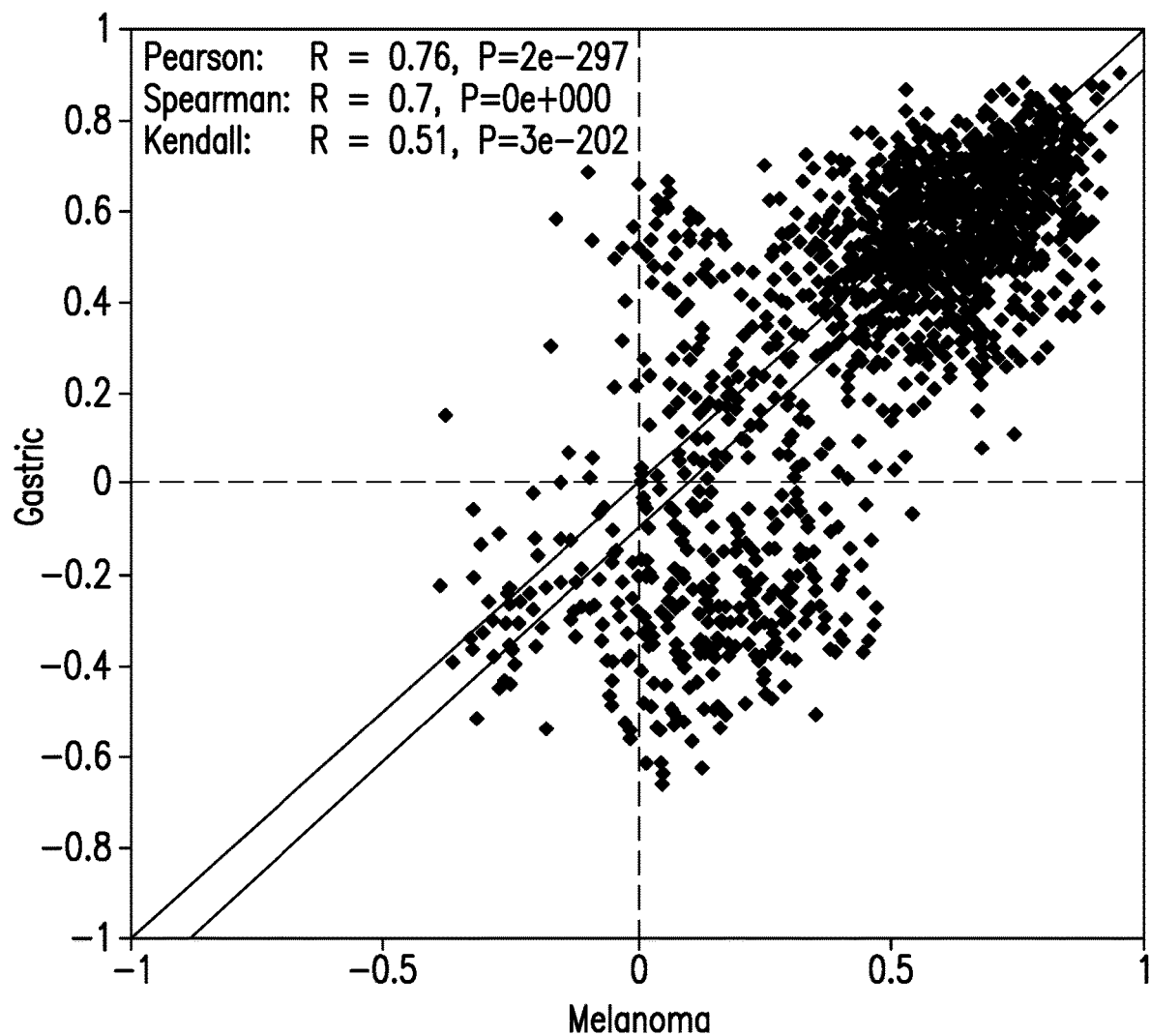
Figure 2D:
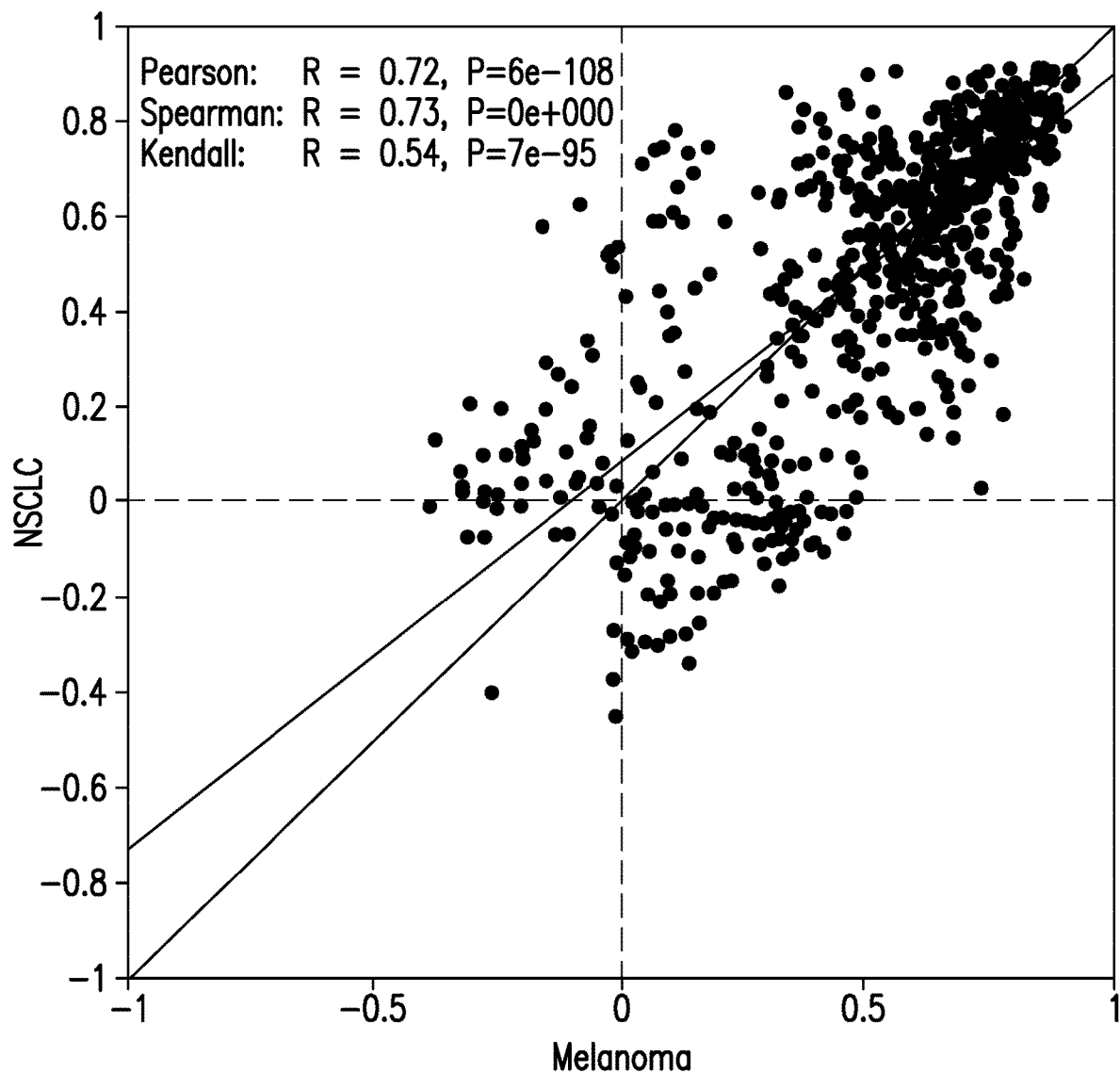
Figure 2E:
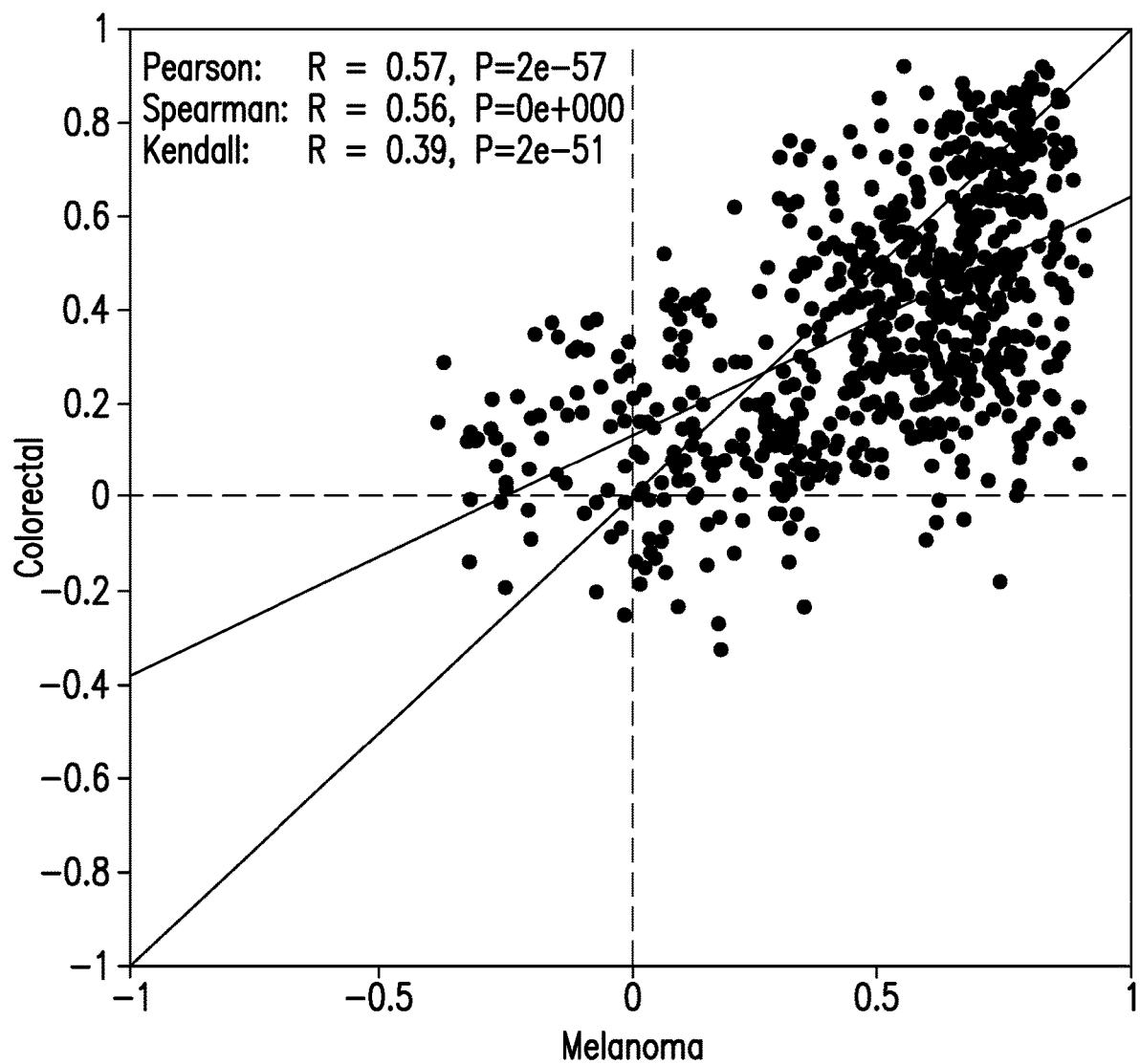
Figure 2F:
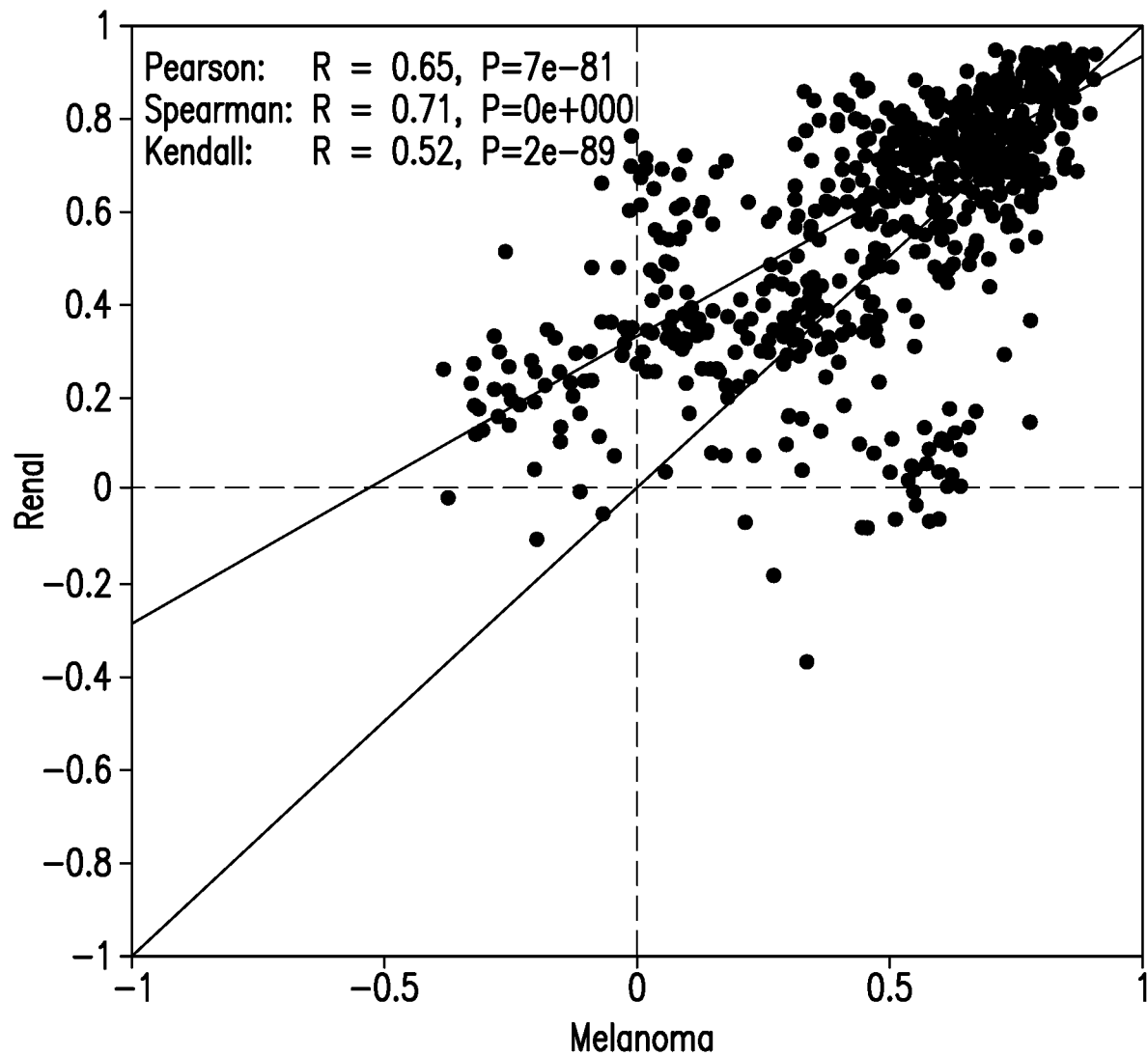
Figure 2G:
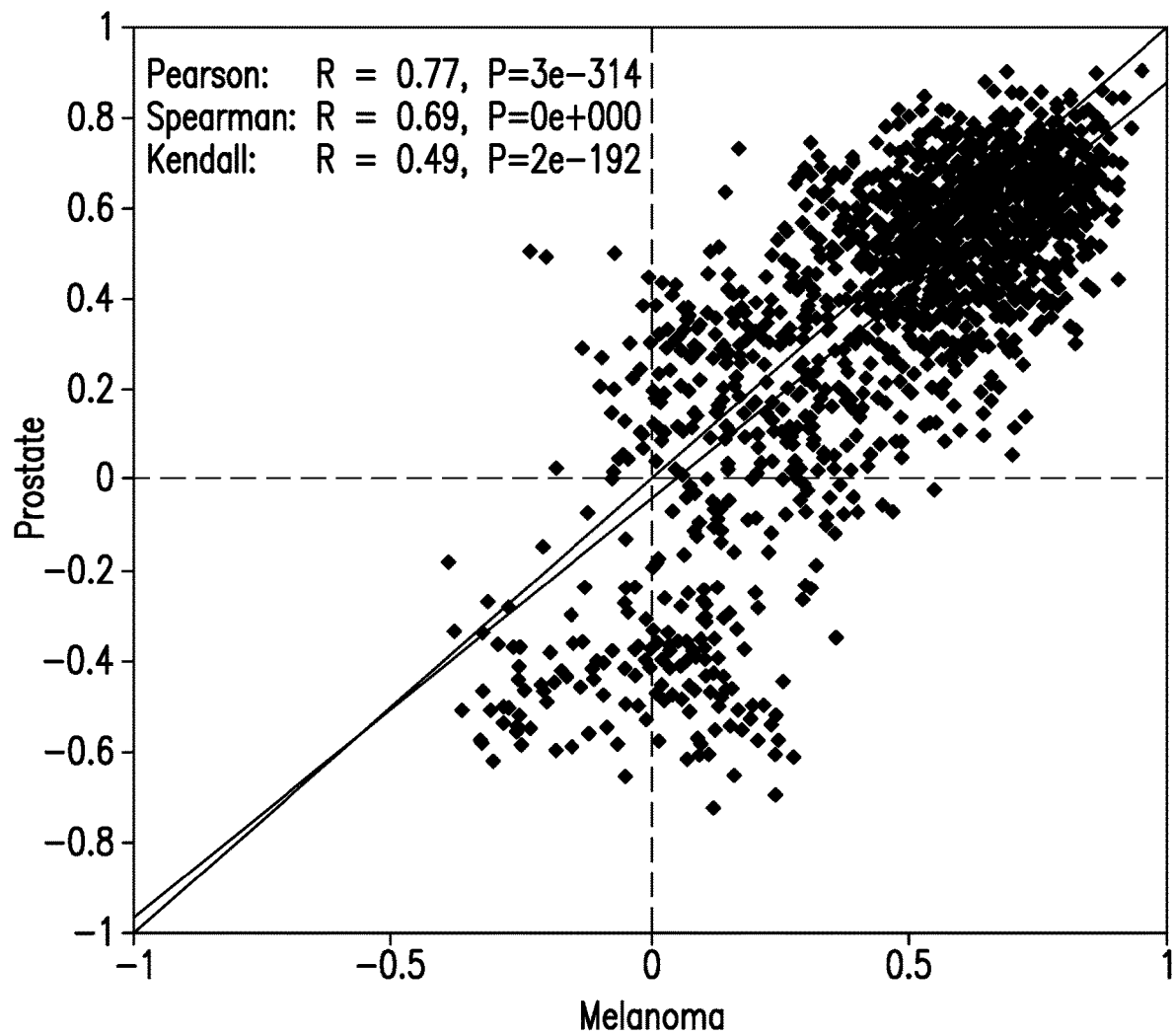
Figure 2H:
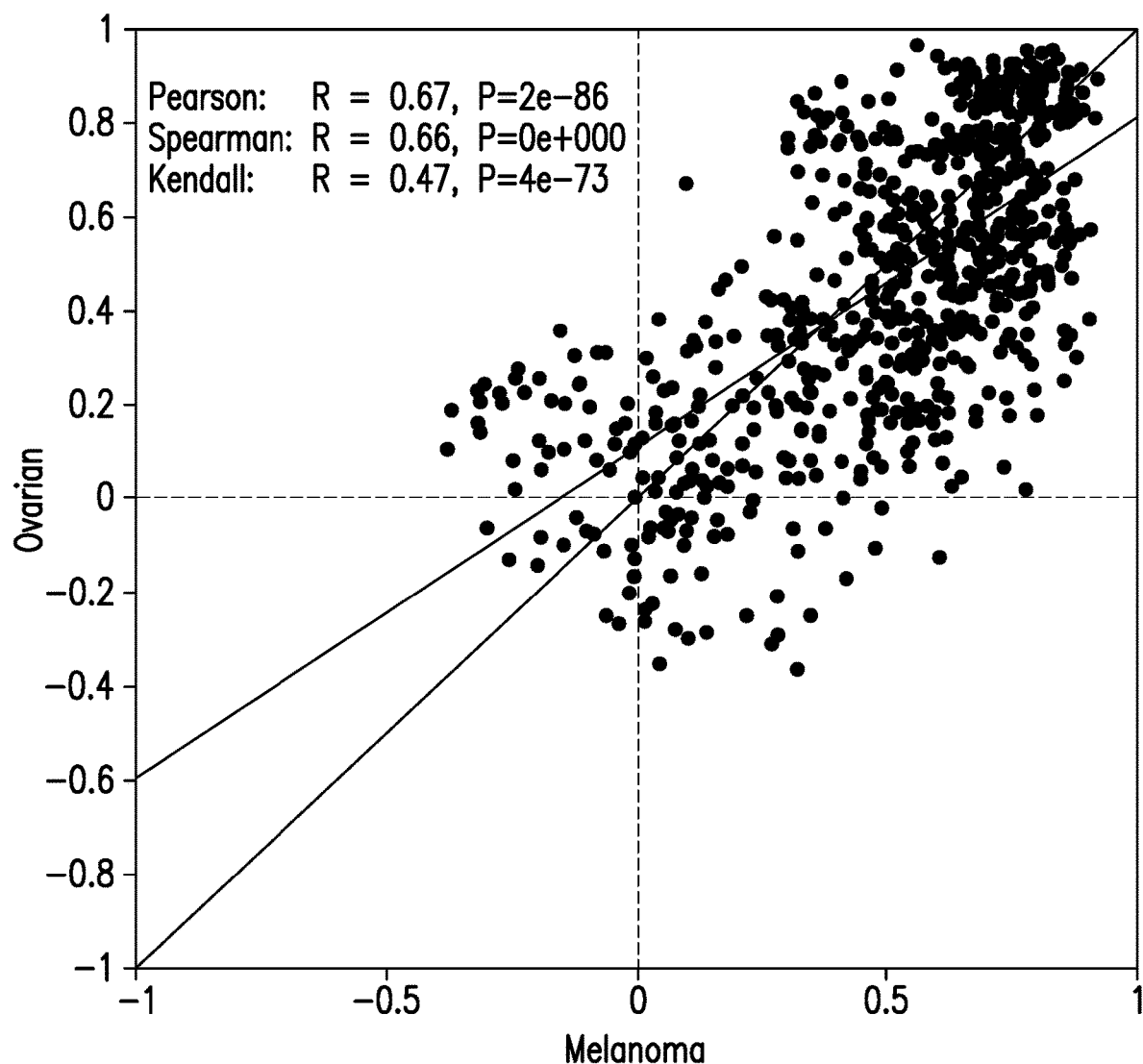
Figure 2I:
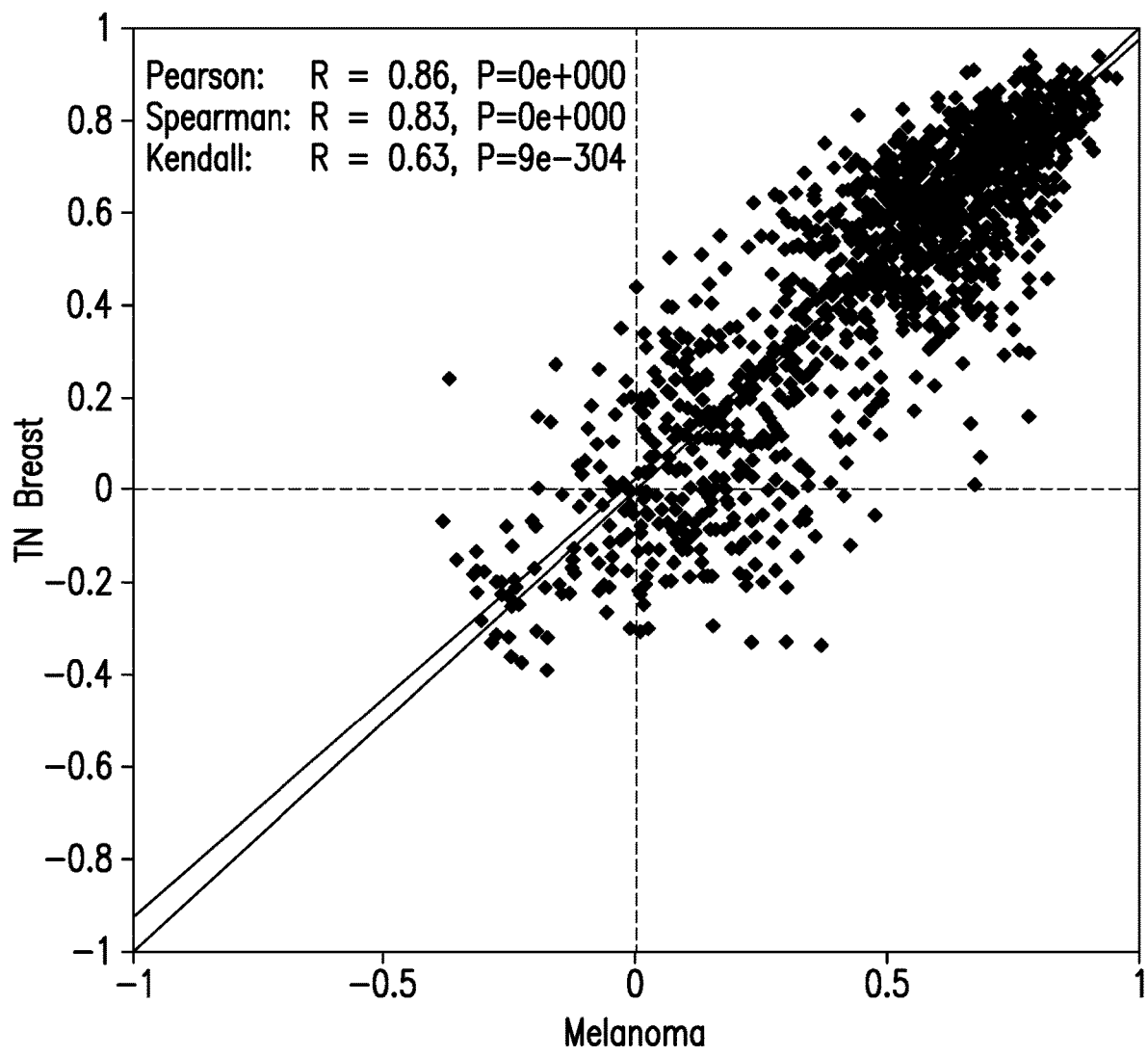

Throughout the detailed description and examples of the invention the following abbreviations will be used:
BOR Best overall response
CDR Complementarity determining region
CHO Chinese hamster ovary
CR Complete Response
DFS Disease free survival
FFPE Formalin-fixed, paraffin-embedded
FR Framework region
IHC Immunohistochemistry or immunohistochemical
irRC Immune related response criteria
NCBI National Center for Biotechnology Information
NPV Net predictive value
OR Overall response
OS Overall survival
PD Progressive Disease
PD-1 Programmed Death 1
PD-L1 Programmed Cell Death 1 Ligand 1
PD-L2 Programmed Cell Death 1 Ligand 2
PFS Progression free survival (PFS)
PPV Positive predictive value
PR Partial Response Q2W One dose every two weeks
Q3W One dose every three weeks
RECIST Response Evaluation Criteria in Solid Tumors
ROC Receiver operating characteristic
SD Stable Disease
VH Immunoglobulin heavy chain variable region
VK Immunoglobulin kappa light chain variable region II. Definitions So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"About" when used to modify a numerically defined parameter (e.g., the gene signature score for a gene signature discussed herein, or the dosage of a PD-1 antagonist, or the length of treatment time with a PD-1 antagonist) means that the parameter may vary by as much as 10% above or below the stated numerical value for that parameter. For example, a gene signature consisting of about 10 genes may have between 9 and 11 genes. Similarly, a reference gene signature score of about 2.462 includes scores of and any score between 2.2158 and 2.708.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, dog, cat, rabbit) and most preferably a human.

As used herein, the term "antibody" refers to any form of antibody that exhibits the desired biological or binding activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, chimeric antibodies and camelized single domain antibodies. "Parental antibodies" are antibodies obtained by exposure of an immune system to an antigen prior to modification of the antibodies for an intended use, such as humanization of a parental antibody generated in a mouse for use as a human therapeutic.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), which are located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; $5^{th}$ ed.; NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) Nature 342:878-883.

As used herein, the term "hypervariable region" refers to the amino acid residues of an antibody that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). See Kabat et al. (1991) Sequences of Proteins of Immunological Interest, 5th Ed. Public Health Service, National Institutes of Health, Bethesda, Md. (defining the CDR regions of an antibody by sequence); see also Chothia and Lesk (1987) *J. Mol. Biol.* 196: 901-917 (defining the CDR regions of an antibody by structure). As used herein, the term "framework" or "FR" residues refers to those variable domain residues other than the hypervariable region residues defined herein as CDR residues.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', $F(ab')_2$, and Fv fragments; diabodies; linear antibodies; single-chain antibody molecules, e.g., sc-Fv; nanobodies and multispecific antibodies formed from antibody fragments.

An antibody that "specifically binds to" a specified target protein is an antibody that exhibits preferential binding to that target as compared to other proteins, but this specificity does not require absolute binding specificity. An antibody is considered "specific" for its intended target if its binding is determinative of the presence of the target protein in a sample, e.g. without producing undesired results such as false positives. Antibodies, or binding fragments thereof, useful in the present invention will bind to the target protein with an affinity that is at least two fold greater, preferably at least ten times greater, more preferably at least 20-times greater, and most preferably at least 100-times greater than the affinity with non-target proteins. As used herein, an antibody is said to bind specifically to a polypeptide comprising a given amino acid sequence, e.g. the amino acid sequence of a mature human PD-1 or human PD-L1 molecule, if it binds to polypeptides comprising that sequence but does not bind to proteins lacking that sequence.

"Chimeric antibody" refers to an antibody in which a portion of the heavy and/or light chain is identical with or homologous to corresponding sequences in an antibody derived from a particular species (e.g., human) or belonging to a particular antibody class or subclass, while the remainder of the chain(s) is identical with or homologous to corresponding sequences in an antibody derived from another species (e.g., mouse) or belonging to another antibody class or subclass, as well as fragments of such antibodies, so long as they exhibit the desired biological activity.

"Human antibody" refers to an antibody that comprises human immunoglobulin protein sequences only. A human antibody may contain murine carbohydrate chains if produced in a mouse, in a mouse cell, or in a hybridoma derived from a mouse cell. Similarly, "mouse antibody" or "rat antibody" refer to an antibody that comprises only mouse or rat immunoglobulin sequences, respectively.

"Humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The humanized forms of rodent antibodies will generally comprise the same CDR sequences of the parental rodent antibodies, although certain amino acid substitutions may be included to increase affinity, increase stability of the humanized antibody, or for other reasons.

"Anti-tumor response" when referring to a cancer patient treated with a therapeutic agent, such as a PD-1 antagonist, means at least one positive therapeutic effect, such as for example, reduced number of cancer cells, reduced tumor size, reduced rate of cancer cell infiltration into peripheral organs, reduced rate of tumor metastasis or tumor growth, or progression free survival. Positive therapeutic effects in cancer can be measured in a number of ways (See, W. A. Weber, J. Null. Med. 50:1S-10S (2009); Eisenhauer et al., supra). In some embodiments, an anti-tumor response to a PD-1 antagonist is assessed using RECIST 1.1 criteria, bidimensional irRC or unidimensional irRC. In some embodiments, an anti-tumor response is any of SD, PR, CR, PFS, DFS. In some embodiments, a gene signature biomarker of the invention predicts whether a subject with a solid tumor is likely to achieve a PR or a CR.

"Bidimensional irRC" refers to the set of criteria described in Wolchok J D, et al. Guidelines for the evaluation of immune therapy activity in solid tumors: immune-related response criteria. *Clin Cancer Res.* 2009; 15(23): 7412-7420. These criteria utilize bidimensional tumor measurements of target lesions, which are obtained by multiplying the longest diameter and the longest perpendicular diameter ($cm^2$) of each lesion.

"Biotherapeutic agent" means a biological molecule, such as an antibody or fusion protein, that blocks ligand/receptor signaling in any biological pathway that supports tumor maintenance and/or growth or suppresses the anti-tumor immune response.

The terms "cancer", "cancerous", or "malignant" refer to or describe the physiological condition in mammals that is typically characterized by unregulated cell growth. Examples of cancer include but are not limited to, carcinoma, lymphoma, leukemia, blastoma, and sarcoma. More particular examples of such cancers include squamous cell carcinoma, myeloma, small-cell lung cancer, non-small cell lung cancer, glioma, hodgkin's lymphoma, non-hodgkin's lymphoma, acute myeloid leukemia (AML), multiple myeloma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, and head and neck cancer. Particularly preferred cancers that may be treated in accordance with the present invention include those characterized by elevated expression of one or both of PD-L1 and PD-L2 in tested tissue samples.

"CDR" or "CDRs" as used herein means complementarity determining region(s) in an immunoglobulin variable region, defined using the Kabat numbering system, unless otherwise indicated.

"Chemotherapeutic agent" is a chemical compound useful in the treatment of cancer. Classes of chemotherapeutic agents include, but are not limited to: alkylating agents, antimetabolites, kinase inhibitors, spindle poison plant alkaloids, cytoxic/antitumor antibiotics, topoisomerase inhibitors, photosensitizers, anti-estrogens and selective estrogen receptor modulators (SERMs), anti-progesterones, estrogen receptor down-regulators (ERDs), estrogen receptor antagonists, leutinizing hormone-releasing hormone agonists, anti-androgens, aromatase inhibitors, EGFR inhibitors, VEGF inhibitors, anti-sense oligonucleotides that that inhibit expression of genes implicated in abnormal cell proliferation or tumor growth. Chemotherapeutic agents useful in the treatment methods of the present invention include cytostatic and/or cytotoxic agents.

"Clothia" as used herein means an antibody numbering system described in Al-Lazikani et al., *JMB* 273:927-948 (1997).

"Comprising" or variations such as "comprise", "comprises" or "comprised of" are used throughout the specification and claims in an inclusive sense, i.e., to specify the presence of the stated features but not to preclude the presence or addition of further features that may materially enhance the operation or utility of any of the embodiments of the invention, unless the context requires otherwise due to express language or necessary implication.

"Consists essentially of," and variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, if a gene signature score is defined as the composite RNA expression score for a set of genes that consists of a specified list of genes, the skilled artisan will understand that this gene signature score could include the RNA level determined for one or more additional genes, preferably no more than three additional genes, if such inclusion does not materially affect the predictive power.

"Framework region" or "FR" as used herein means the immunoglobulin variable regions excluding the CDR regions.

"Homology" refers to sequence similarity between two polypeptide sequences when they are optimally aligned. When a position in both of the two compared sequences is occupied by the same amino acid monomer subunit, e.g., if a position in a light chain CDR of two different Abs is occupied by alanine, then the two Abs are homologous at that position. The percent of homology is the number of homologous positions shared by the two sequences divided by the total number of positions compared ×100. For example, if 8 of 10 of the positions in two sequences are matched or homologous when the sequences are optimally aligned then the two sequences are 80% homologous. Generally, the comparison is made when two sequences are aligned to give maximum percent homology. For example, the comparison can be performed by a BLAST algorithm wherein the parameters of the algorithm are selected to give the largest match between the respective sequences over the entire length of the respective reference sequences.

The following references relate to BLAST algorithms often used for sequence analysis: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, N.Y. "Isolated antibody" and "isolated antibody fragment" refers to the purification status and in such context means the named molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

"Kabat" as used herein means an immunoglobulin alignment and numbering system pioneered by Elvin A. Kabat ((1991) Sequences of Proteins of Immunological Interest, 5th Ed. Public Health Service, National Institutes of Health, Bethesda, Md.).

"Monoclonal antibody" or "mAb" or "Mab", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352: 624-628 and Marks et al. (1991) J. Mol. Biol. 222: 581-597, for example. See also Presta (2005) J. Allergy Clin. Immunol. 116:731.

"Non-responder patient" when referring to a specific anti-tumor response to treatment with a PD-1 antagonist, means the patient did not exhibit the anti-tumor response.

"Oligonucleotide" refers to a nucleic acid that is usually between 5 and 100 contiguous bases in length, and most frequently between 10-50, 10-40, 10-30, 10-25, 10-20, 15-50, 15-40, 15-30, 15-25, 15-20, 20-50, 20-40, 20-30 or 20-25 contiguous bases in length.

"Patient" refers to any single human subject for which therapy is desired or that is participating in a clinical trial, epidemiological study or used as a control.

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the various aspects and embodiments of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in the any of the various aspects and embodiments of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments, the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments.

Examples of mAbs that bind to human PD-1, and useful in the various aspects and embodiments of the present invention, are described in U.S. Pat. Nos. 7,521,051, 8,008,449, and 8,354,509. Specific anti-human PD-1 mAbs useful as the PD-1 antagonist various aspects and embodiments of the present invention include: pembrolizumab, a humanized IgG4 mAb with the structure described in *WHO Drug Information*, Vol. 27, No. 2, pages 161-162 (2013), nivolumab (BMS-936558), a human IgG4 mAb with the structure described in *WHO Drug Information*, Vol. 27, No. 1, pages 68-69 (2013); pidilizumab (CT-011, also known as hBAT or hBAT-1); and the humanized antibodies h409A11; h409A16 and h409A17, which are described in WO2008/156712.

Additional PD-1 antagonists useful in any of the various aspects and embodiments of the present invention include a pembrolizumab biosimilar or a pembrolizumab variant.

As used herein "pembrolizumab biosimilar" means a biological product that (a) is marketed by an entity other than Merck and Co., Inc. or a subsidiary thereof and (b) is approved by a regulatory agency in any country for marketing as a pembrolizumab biosimilar. In an embodiment, a pembrolizumab biosimilar comprises a pembrolizumab variant as the drug substance. In an embodiment, a pembrolizumab biosimilar has the same amino acid sequence as pembrolizumab.

As used herein, a "pembrolizumab variant" means a monoclonal antibody which comprises heavy chain and light chain sequences that are identical to those in pembrolizumab, except for having three, two or one conservative amino acid substitutions at positions that are located outside of the light chain CDRs and six, five, four, three, two or one conservative amino acid substitutions that are located outside of the heavy chain CDRs, e.g, the variant positions are located in the FR regions or the constant region. In other words, pembrolizumab and a pembrolizumab variant comprise identical CDR sequences, but differ from each other due to having a conservative amino acid substitution at no more than three or six other positions in their full length light and heavy chain sequences, respectively. A pembrolizumab variant is substantially the same as pembrolizumab with respect to the following properties: binding affinity to PD-1 and ability to block the binding of each of PD-L1 and PD-L2 to PD-1.

Examples of mAbs that bind to human PD-L1, and useful in any of the various aspects and embodiments of the present invention, are described in WO2013/019906, WO2010/077634 A1 and U.S. Pat. No. 8,383,796. Specific anti-human PD-L1 mAbs useful as the PD-1 antagonist in the various aspects and embodiments of the present invention include MPDL3280A (atezolizumab), BMS-936559, MEDI4736, MSB0010718C (avelumab) and an antibody which comprises the heavy chain and light chain variable regions of SEQ ID NO:24 and SEQ ID NO:21, respectively, of WO2013/019906.

Other PD-1 antagonists useful in any of the various aspects and embodiments of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesin on molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

"Probe" as used herein means an oligonucleotide that is capable of specifically hybridizing under stringent hybridization conditions to a transcript expressed by a gene of interest listed in Table 1, and in some preferred embodiments, specifically hybridizes under stringent hybridization conditions to the particular transcript listed in Table 1 for the gene of interest.

"RECIST 1.1 Response Criteria" as used herein means the definitions set forth in Eisenhauer et al., E. A. et al., Eur. J Cancer 45:228-247 (2009) for target lesions or nontarget lesions, as appropriate based on the context in which response is being measured.

"Reference IFN-γ gene signature score" as used herein means the score for an IFN-γ gene signature that has been determined to divide at least the majority of responders from at least the majority of non-responders in a reference population of subjects who have the same tumor type as a test subject and who have been treated with a PD-1 antagonist. Preferably, at least any of 60%, 70%, 80%, or 90% of responders in the reference population will have an IFN-γ gene signature score that is above the selected reference score, while the IFN-γ gene signature score for at least any of 60%, 70% 80%, 90% or 95% of the non-responders in the reference population will be lower than the selected reference score. In some embodiments, the negative predictive value of the reference score is greater than the positive predictive value. In some preferred embodiments, responders in the reference population are defined as subjects who achieved a partial response (PR) or complete response (CR) as measured by RECIST 1.1 criteria and non-responders are defined as not achieving any RECIST 1.1 clinical response. In particularly preferred embodiments, subjects in the reference population were treated with substantially the same anti-PD-1 therapy as that being considered for the test subject, i.e., administration of the same PD-1 antagonist using the same or a substantially similar dosage regimen.

"Sample" when referring to a tumor or any other biological material referenced herein, means a sample that has been removed from the subject; thus, none of the testing methods described herein are performed in or on the subject.

"Responder patient" when referring to a specific anti-tumor response to treatment with a PD-1 antagonist, means the patient exhibited the anti-tumor response.

"Sustained response" means a sustained therapeutic effect after cessation of treatment with a therapeutic agent, or a combination therapy described herein. In some embodiments, the sustained response has a duration that is at least the same as the treatment duration, or at least 1.5, 2.0, 2.5 or 3 times longer than the treatment duration.

"Tissue Section" refers to a single part or piece of a tissue sample, e.g., a thin slice of tissue cut from a sample of a normal tissue or of a tumor.

"Treat" or "treating" a cancer as used herein means to administer a PD-1 antagonist other therapeutic agent to a subject having a cancer, or diagnosed with a cancer, to achieve at least one positive therapeutic effect, such as for example, reduced number of cancer cells, reduced tumor size or tumor burden, reduced rate of cancer cell infiltration into peripheral organs, or reduced rate of tumor metastasis or tumor growth. Positive therapeutic effects in cancer can be measured in a number of ways (See, W. A. Weber, J. Null. Med. 50:1S-10S (2009); Eisenhauer et al., supra). In some preferred embodiments, response to a PD-1 antagonist is assessed using RECIST 1.1 criteria or irRC. In some embodiments, the treatment achieved by a therapeutically effective amount is any of PR, CR, PFS, DFS, OR or OS. In some preferred embodiments, a gene signature biomarker of the invention predicts whether a subject with a solid tumor is likely to achieve a PR or a CR. The dosage regimen of a therapy described herein that is effective to treat a cancer patient may vary according to factors such as the disease state, age, and weight of the patient, and the ability of the therapy to elicit an anti-cancer response in the subject. While an embodiment of the treatment method, medicaments and uses of the present invention may not be effective in achieving a positive therapeutic effect in every subject, it should do so in a statistically significant number of subjects as determined by any statistical test known in the art such as the Student's t-test, the $chi^2$-test, the U-test according to Mann and Whitney, the Kruskal-Wallis test (H-test), Jonckheere-Terpstra-test and the Wilcoxon-test.

"Tumor" as it applies to a subject diagnosed with, or suspected of having, a cancer refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms).

"Tumor burden" also referred to as "tumor load", refers to the total amount of tumor material distributed throughout the body. Tumor burden refers to the total number of cancer cells or the total size of tumor(s), throughout the body, including lymph nodes and bone narrow. Tumor burden can be determined by a variety of methods known in the art, such as, e.g. by measuring the dimensions of tumor(s) upon removal from the subject, e.g., using calipers, or while in the body using imaging techniques, e.g., ultrasound, bone scan, computed tomography (CT) or magnetic resonance imaging (MRI) scans.

The term "tumor size" refers to the total size of the tumor which can be measured as the length and width of a tumor. Tumor size may be determined by a variety of methods known in the art, such as, e.g. by measuring the dimensions of tumor(s) upon removal from the subject, e.g., using calipers, or while in the body using imaging techniques, e.g., bone scan, ultrasound, CT or MRI scans.

"Unidimensional irRC refers to the set of criteria described in Nishino M, Giobbie-Hurder A, Gargano M, Suda M, Ramaiya N H, Hodi F S. Developing a Common Language for Tumor Response to Immunotherapy: Immune-related Response Criteria using Unidimensional measurements. *Clin Cancer Res.* 2013; 19(14):3936-3943). These criteria utilize the longest diameter (cm) of each lesion.

"Variable regions" or "V region" as used herein means the segment of IgG chains which is variable in sequence between different antibodies. It extends to Kabat residue 109 in the light chain and 113 in the heavy chain.

III. Composition of the Gene Expression Platform

The inventors have constructed a gene expression platform of the 57 clinical response genes and the 11 normalization genes listed in Table 1 above, and have further identified the gene signatures shown in Table 2 above, which are represented in the clinical response gene set and are correlated with response to pembrolizumab across multiple tumor types. Since there are several genes in common to each of these gene signatures, the inventors propose that gene signature biomarkers that are predictive of response to a PD-1 antagonist may be derived for any of these signatures, as well as for other gene signatures comprising any combination of 2 to 57 of the clinical response genes in Table 1. By measuring RNA levels for each gene in Table 1 and then computing signature scores from the normalized RNA levels for only the genes in each gene signature of interest, a single gene expression analysis system may be used to generate and evaluate gene signature scores for different gene signatures and different tumor types to derive candidate biomarkers of anti-tumor response to a PD-1 antagonist.

However, the inventors contemplate that other gene expression platforms comprising a clinical response gene set and a normalization gene set may be constructed that provide very similar functionality as the platform shown in Table 1, provided that the gene sets in the platform meet all of the following criteria: (1) the genes in the clinical response gene set are (a) individually correlated with an anti-tumor response to a PD-1 antagonist in more than one tumor type and (b) collectively generate a covariance pattern that is substantially similar in each of the tumor types; (2) the clinical response gene set consists of between about 50 and about 60 genes, and about 90% of the clinical response genes exhibit intratumoral RNA levels that are positively correlated with the anti-tumor response and about 10% of the clinical response genes exhibit intratumoral RNA levels that are negatively correlated with the anti-tumor response; (3) the genes in the normalization gene set individually exhibit intratumoral RNA levels of low variance across multiple samples of the different tumor types and collectively exhibit a range of intratumoral RNA levels that spans the range of intratumoral expression levels of the clinical response genes in the different tumor types; and (4) the normalization gene set consists of between about 10 to about 12 housekeeping genes.

Such alternative gene expression platforms can be constructed following the approach described in Example 2 below. An alternative gene expression platform useful in the methods and system of the invention comprises at least 40, 45, 50 or 55 of the clinical response genes in Table 1 and one or more additional clinical response genes that are not in Table 1. In one embodiment, the clinical response gene set comprises any number between 55 and 57 of the clinical response genes in Table 1 and the normalization gene set comprises at least 9 of the normalization genes in Table 1 and at least one housekeeping gene that is not in Table 1.

IV. Model-Based Derivation of Gene Signature Scores

Gene signature scores may be derived by using the entire clinical response gene set, or any subset thereof, as a set of input covariates to multivariate statistical models that will determine signature scores using the fitted model coefficients, for example the linear predictor in a logistic or Cox regression. One specific example of a multivariate strategy is the use of elastic net modeling (Zou & Hastie, 2005, *J. R. Statist Soc. B* 67(2): 301-320; Simon et al., 2011, *J. Statistical Software* 39(5): 1-13), which is a penalized regression approach that uses a hybrid between the penalties of the lasso and ridge regression, with cross-validation to select the penalty parameters. Because the RNA expression levels for most, if not all, of the clinical response genes are expected to be predictive, in one embodiment the L1 penalty parameter may be set very low, effectively running a ridge regression.

A multivariate approach may use a meta-analysis that combines data across cancer indications or may be applied within a single cancer indication. In either case, analyses would use the normalized intra-tumoral RNA expression levels of the signature gene as the input predictors, with anti-tumor response as the dependent variable. The result of such an analysis algorithmically defines the signature score for tumor samples from the patients used in the model fit, as well as for tumor samples from future patients, as a numeric combination of the multiplication co-efficients for the normalized RNA expression levels of the signature genes that is expected to be predictive of anti-tumor response. The gene signature score is determined by the linear combination of the signature genes, as dictated by the final estimated values of the elastic net model coefficients at the selected values of the tuning parameters. Specifically, for a given tumor sample, the estimated coefficient for each gene is multiplied by the normalized RNA expression level of that gene in the tumor sample and then the resulting products are summed to yield the signature score for that tumor sample. Multivariate model-based strategies other than elastic net could also be used to determine a gene signature score.

An alternative to such model-based signature scores would be to use a simple averaging approach, e.g., the signature score for each tumor sample would be defined as the average of that sample's normalized RNA expression levels for those signature genes deemed to be positively associated with the anti-tumor response minus the average of that sample's normalized RNA expression levels for those signature genes deemed to be negatively associated with the anti-tumor response.

V. Utility of Gene Signatures and Biomarkers of the Invention

Gene signatures and gene signature biomarkers derived using the system and methods described herein may be useful to identify cancer patients who are most likely to achieve a clinical benefit from treatment with a PD-1 antagonist. This utility supports the use of such biomarkers in a variety of research and commercial applications, including but not limited to, clinical trials of PD-1 antagonists in which patients are selected on the basis of whether they test positive or negative for a gene signature biomarker, diagnostic methods and products for determining a patient's gene signature score or for classifying a patient as positive or negative for a gene signature biomarker, personalized treatment methods which involve tailoring a patient's drug therapy based on the patient's gene signature score or biomarker status, as well as pharmaceutical compositions and drug products comprising a PD-1 antagonist for use in treating patients who test positive for a gene signature biomarker.

The utility of any of the research and commercial applications claimed herein does not require that 100% of the patients who test positive for a gene signature biomarker achieve an anti-tumor response to a PD-1 antagonist; nor does it require a diagnostic method or kit to have a specific degree of specificity or sensitivity in determining the presence or absence of a biomarker in every subject, nor does it require that a diagnostic method claimed herein be 100% accurate in predicting for every subject whether the subject is likely to have a beneficial response to a PD-1 antagonist. Thus, the inventors herein intend that the terms "determine", "determining" and "predicting" should not be interpreted as requiring a definite or certain result; instead these terms should be construed as meaning either that a claimed method provides an accurate result for at least the majority of subjects or that the result or prediction for any given subject is more likely to be correct than incorrect.

Preferably, the accuracy of the result provided by a diagnostic method of the invention is one that a skilled artisan or regulatory authority would consider suitable for the particular application in which the method is used.

Similarly, the utility of the claimed drug products and treatment methods does not require that the claimed or desired effect is produced in every cancer patient; all that is required is that a clinical practitioner, when applying his or her professional judgment consistent with all applicable norms, decides that the chance of achieving the claimed effect of treating a given patient according to the claimed method or with the claimed composition or drug product.

A. Assaying Tumor Samples for Gene Signatures and Biomarkers

A gene signature score is determined in a sample of tumor tissue removed from a subject. The tumor may be primary or recurrent, and may be of any type (as described above), any stage (e.g., Stage I, II, III, or IV or an equivalent of other staging system), and/or histology. The subject may be of any age, gender, treatment history and/or extent and duration of remission.

The tumor sample can be obtained by a variety of procedures including, but not limited to, surgical excision, aspiration or biopsy. The tissue sample may be sectioned and assayed as a fresh specimen; alternatively, the tissue sample may be frozen for further sectioning. In some preferred embodiments, the tissue sample is preserved by fixing and embedding in paraffin or the like.

The tumor tissue sample may be fixed by conventional methodology, with the length of fixation depending on the size of the tissue sample and the fixative used. Neutral buffered formalin, glutaraldehyde, Bouin's and paraformaldehyde are nonlimiting examples of fixatives. In preferred embodiments, the tissue sample is fixed with formalin. In some embodiments, the fixed tissue sample is also embedded in paraffin to prepare an FFPE tissue sample.

Typically, the tissue sample is fixed and dehydrated through an ascending series of alcohols, infiltrated and embedded with paraffin or other sectioning media so that the tissue sample may be sectioned. Alternatively, the tumor tissue sample is first sectioned and then the individual sections are fixed.

In some preferred embodiments, the gene signature score for a tumor is determined using FFPE tissue sections of about 3-4 millimeters, and preferably 4 micrometers, which are mounted and dried on a microscope slide.

Once a suitable sample of tumor tissue has been obtained, it is analyzed to quantitate the RNA expression level for each of the genes in Table 1, or for a gene signature derived therefrom. The phrase "determine the RNA expression level of a gene" as used herein refers to detecting and quantifying RNA transcribed from that gene. The term "RNA transcript" includes mRNA transcribed from the gene, and/or specific spliced variants thereof and/or fragments of such mRNA and spliced variants. In some embodiments, the RNA transcript for a Table 1 gene comprises the target region listed in Table 1.

A person skilled in the art will appreciate that a number of methods can be used to isolate RNA from the tissue sample for analysis. For example, RNA may be isolated from frozen tissue samples by homogenization in guanidinium isothiocyanate and acid phenol-chloroform extraction. Commercial kits are available for isolating RNA from FFPE samples.

If the tumor sample is an FFPE tissue section on a glass slide, it is possible to perform gene expression analysis on whole cell lysates rather than on isolated total RNA. These lysates may be prepared as described in Example 1 below.

Persons skilled in the art are also aware of several methods useful for detecting and quantifying the level of RNA transcripts within the isolated RNA or whole cell lysates. Quantitative detection methods include, but are not limited to, arrays (i.e., microarrays), quantitative real time PCR (RT-PCR), multiplex assays, nuclease protection assays, and Northern blot analyses. Generally, such methods employ labeled probes that are complimentary to a portion of each transcript to be detected. Probes for use in these methods can be readily designed based on the known sequences of the genes and the transcripts expressed thereby. In some embodiments, a probe for detecting a transcript of a gene in Table 1 is designed to specifically hybridize to the target region for that gene that is identified in Table 1. Suitable labels for the probes are well-known and include, e.g., fluorescent, chemilumnescent and radioactive labels.

In some embodiments, assaying a tumor sample for expression of the genes in Table 1, or gene signatures derived therefrom, employs detection and quantification of RNA levels in real-time using nucleic acid sequence based amplification (NASBA) combined with molecular beacon detection molecules. NASBA is described, e.g., in Compton J., *Nature* 350 (6313):91-92 (1991). NASBA is a single-step isothermal RNA-specific amplification method. Generally, the method involves the following steps: RNA template is provided to a reaction mixture, where the first primer attaches to its complementary site at the 3' end of the template; reverse transcriptase synthesizes the opposite, complementary DNA strand; RNAse H destroys the RNA template (RNAse H only destroys RNA in RNA-DNA hybrids, but not single-stranded RNA); the second primer attaches to the 3' end of the DNA strand, and reverse transcriptase synthesizes the second strand of DNA; and T7 RNA polymerase binds double-stranded DNA and produces a complementary RNA strand which can be used again in step 1, such that the reaction is cyclic.

In other embodiments, the assay format is a flap endonuclease-based format, such as the Invader™ assay (Third Wave Technologies). In the case of using the invader method, an invader probe containing a sequence specific to the region 3' to a target site, and a primary probe containing a sequence specific to the region 5' to the target site of a template and an unrelated flap sequence, are prepared. Cleavase is then allowed to act in the presence of these probes, the target molecule, as well as a FRET probe containing a sequence complementary to the flap sequence and an auto-complementary sequence that is labeled with both a fluorescent dye and a quencher. When the primary probe hybridizes with the template, the 3' end of the invader probe penetrates the target site, and this structure is cleaved by the Cleavase resulting in dissociation of the flap. The flap binds to the FRET probe and the fluorescent dye portion is cleaved by the Cleavase resulting in emission of fluorescence.

In yet other embodiments, the assay format employs direct mRNA capture with branched DNA (QuantiGene™, Panomics) or Hybrid Capture™ (Digene).

One example of an array technology suitable for use in measuring expression of the genes in gene expression platform of the invention is the ArrayPlate™ assay technology sold by HTG Molecular, Tucson Ariz., and described in Martel, R. R., et al., Assay and Drug Development Technologies 1(1):61-71, 2002. In brief, this technology combines a nuclease protection assay with array detection. Cells in microplate wells are subjected to a nuclease protection assay. Cells are lysed in the presence of probes that bind targeted mRNA species. Upon addition of SI nuclease, excess probes and unhybridized mRNA are degraded, so that only mRNA:probe duplexes remain. Alkaline hydrolysis destroys the mRNA component of the duplexes, leaving probes intact. After the addition of a neutralization solution, the contents of the processed cell culture plate are transferred to another ArrayPlate™ called a programmed ArrayPlate™. ArrayPlates™ contain a 16-element array at the bottom of each well. Each array element comprises a position-specific anchor oligonucleotide that remains the same from one assay to the next. The binding specificity of each of the 16 anchors is modified with an oligonucleotide, called a programming linker oligonucleotide, which is complementary at one end to an anchor and at the other end to a nuclease protection probe. During a hybridization reaction, probes transferred from the culture plate are captured by immobilized programming linker. Captured probes are labeled by hybridization with a detection linker oligonucleotide, which is in turn labeled with a detection conjugate that incorporates peroxidase. The enzyme is supplied with a chemiluminescent substrate, and the enzyme-produced light is captured in a digital image. Light intensity at an array element is a measure of the amount of corresponding target mRNA present in the original cells.

By way of further example, DNA microarrays can be used to measure gene expression. In brief, a DNA microarray, also referred to as a DNA chip, is a microscopic array of DNA fragments, such as synthetic oligonucleotides, disposed in a defined pattern on a solid support, wherein they are amenable to analysis by standard hybridization methods (see Schena, *BioEssays* 18:427 (1996)). Exemplary microarrays and methods for their manufacture and use are set forth in T. R. Hughes et al., *Nature Biotechnology* 9:342-347 (2001). A number of different microarray configurations and methods for their production are known to those of skill in the art and are disclosed in U.S. Pat. Nos. 5,242,974; 5,384,261; 5,405,783; 5,412,087; 5,424,186; 5,429,807; 5,436,327; 5,445,934; 5,556,752; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,624,711; 5,700,637; 5,744,305; 5,770,456; 5,770,722; 5,837,832; 5,856,101; 5,874,219; 5,885,837; 5,919,523; 6,022,963; 6,077,674; and 6,156,501; Shena, et al., *Tibtech* 6:301-306, 1998; Duggan, et al., *Nat. Genet.* 2:10-14, 1999; Bowtell, et al., *Nat. Genet.* 21:25-32, 1999; Lipshutz, et al., *Nat. Genet.* 21:20-24, 1999; Blanchard, et al., *Biosensors and Bioelectronics* 77:687-90, 1996; Maskos, et al., *Nucleic Acids Res.* 2:4663-69, 1993; and Hughes, et al., *Nat. Biotechnol.* 79:342-347, 2001. Patents describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,848,659; and 5,874,219; the disclosures of which are herein incorporated by reference.

In one embodiment, an array of oligonucleotides may be synthesized on a solid support. Exemplary solid supports include glass, plastics, polymers, metals, metalloids, ceramics, organics, etc. Using chip masking technologies and photoprotective chemistry, it is possible to generate ordered arrays of nucleic acid probes. These arrays, which are known, for example, as "DNA chips" or very large scale immobilized polymer arrays ("VLSIPS®" arrays), may include millions of defined probe regions on a substrate having an area of about 1 cm² to several cm², thereby incorporating from a few to millions of probes (see, e.g., U.S. Pat. No. 5,631,734).

To compare expression levels, labeled nucleic acids may be contacted with the array under conditions sufficient for binding between the target nucleic acid and the probe on the array. In one embodiment, the hybridization conditions may be selected to provide for the desired level of hybridization specificity; that is, conditions sufficient for hybridization to occur between the labeled nucleic acids and probes on the microarray.

Hybridization may be carried out in conditions permitting essentially specific hybridization. The length and GC content of the nucleic acid will determine the thermal melting point and thus, the hybridization conditions necessary for obtaining specific hybridization of the probe to the target nucleic acid. These factors are well known to a person of skill in the art, and may also be tested in assays. An extensive guide to nucleic acid hybridization may be found in Tijssen, et al. (Laboratory Techniques in Biochemistry and Molecular Biology, Vol. 24: Hybridization With Nucleic Acid Probes, P. Tijssen, ed.; Elsevier, N.Y. (1993)). The methods described above will result in the production of hybridization patterns of labeled target nucleic acids on the array surface. The resultant hybridization patterns of labeled nucleic acids may be visualized or detected in a variety of ways, with the particular manner of detection selected based on the particular label of the target nucleic acid. Representative detection means include scintillation counting, autoradiography, fluorescence measurement, calorimetric measurement, light emission measurement, light scattering, and the like.

One such method of detection utilizes an array scanner that is commercially available (Affymetrix, Santa Clara, Calif.), for example, the 417® Arrayer, the 418® Array Scanner, or the Agilent Gene Array® Scanner. This scanner is controlled from a system computer with an interface and easy-to-use software tools. The output may be directly imported into or directly read by a variety of software applications. Exemplary scanning devices are described in, for example, U.S. Pat. Nos. 5,143,854 and 5,424,186.

A preferred assay method to measure transcript abundance for the genes listed in Table 1 utilizes the nCounter® Analysis System marketed by NanoString® Technologies (Seattle, Wash. USA). This system, which is described by Geiss et al., Nature Biotechnol. 2(3):317-325 (2008), utilizes a pair of probes, namely, a capture probe and a reporter probe, each comprising a 35- to 50-base sequence complementary to the transcript to be detected. The capture probe additionally includes a short common sequence coupled to an immobilization tag, e.g. an affinity tag that allows the complex to be immobilized for data collection. The reporter probe additionally includes a detectable signal or label, e.g. is coupled to a color-coded tag. Following hybridization, excess probes are removed from the sample, and hybridized probe/target complexes are aligned and immobilized via the affinity or other tag in a cartridge. The samples are then analyzed, for example using a digital analyzer or other processor adapted for this purpose. Generally, the color-coded tag on each transcript is counted and tabulated for each target transcript to yield the expression level of each transcript in the sample. This system allows measuring the expression of hundreds of unique gene transcripts in a single multiplex assay using capture and reporter probes designed by NanoString.

In measuring expression of the clinical response genes in Table 1 described herein, the absolute expression of each of the genes in a tumor sample is compared to a control; for example, the control can be the average level of expression of each of the genes, respectively, in a pool of subjects. To increase the sensitivity of the comparison, however, the expression level values are preferably transformed in a number of ways.

Raw expression values of the clinical response genes in a gene expression platform described herein may be normalized by any of the following: quantile normalization to a common reference distribution, by the mean RNA levels of a set of housekeeping genes, by global normalization relying on percentile, e.g., $75^{th}$ percentile, or other biologically relevant normalization approaches known to those skilled in the art.

For example, the expression level of each clinical response gene can be normalized by the average RNA expression level of all of the genes in the gene expression platform, or by the average expression level of a set of normalization genes, e.g., housekeeping genes. Thus, in one embodiment, the genes in a gene expression platform are represented by a set of probes, and the RNA expression level of each of the genes is normalized by the mean or median expression level across all of the represented genes, i.e., across all clinical response and normalization genes in a gene expression platform described herein In a specific embodiment, the normalization is carried out by dividing the median or mean level of RNA expression of all of the genes in the gene expression platform. In another embodiment, the RNA expression levels of the clinical response genes are normalized by the mean or median level of expression of a set of normalization genes. In a specific embodiment, the normalization genes comprise housekeeping genes. In another specific embodiment, the normalization of a measured RNA expression level for a clinical response gene is accomplished by dividing the measured level by the median or mean expression level of the normalization genes.

The sensitivity of a gene signature score may be increased if the expression levels of individual genes in the gene signature are compared to the expression of the same genes in a pool of tumor samples. Preferably, the comparison is to the mean or median expression level of each signature gene in the pool of samples. This has the effect of accentuating the relative differences in expression between genes in the sample and genes in the pool as a whole, making comparisons more sensitive and more likely to produce meaningful results than the use of absolute expression levels alone. The expression level data may be transformed in any convenient way; preferably, the expression level data for all genes is log transformed before means or medians are taken.

In performing comparisons to a pool, two approaches may be used. First, the expression levels of the signature genes in the sample may be compared to the expression level of those genes in the pool, where nucleic acid derived from the sample and nucleic acid derived from the pool are hybridized during the course of a single experiment. Such an approach requires that a new pool of nucleic acid be generated for each comparison or limited numbers of comparisons, and is therefore limited by the amount of nucleic acid available. Alternatively, and preferably, the expression levels in a pool, whether normalized and/or transformed or not, are stored on a computer, or on computer-readable media, to be used in comparisons to the individual expression level data from the sample (i.e., single-channel data).

When comparing a subject's tumor sample with a standard or control, the expression value of a particular gene in the sample is compared to the expression value of that gene in the standard or control. For each gene in a gene signature of the invention, the log(10) ratio is created for the expression value in the individual sample relative to the standard or control. A score for a gene signature is calculated by determining the mean log(10) ratio of the genes in the signature. If the gene signature score for the test sample is equal to or greater than a pre-determined threshold for that gene signature, then the sample is considered to be positive for the gene signature biomarker. The pre-determined threshold may also be the mean, median, or a percentile of scores for that gene signature in a collection of samples or a pooled sample used as a standard or control.

It will be recognized by those skilled in the art that other differential expression values, besides log(10) ratio, may be used for calculating a signature score, as long as the value represents an objective measurement of transcript abundance of the genes. Examples include, but are not limited to: xdev, error-weighted log (ratio), and mean subtracted log (intensity).

Each of the steps of obtaining a tissue sample, preparing one or more tissue sections therefrom for assaying gene expression, performing the assay, and scoring the results may be performed by separate individuals at separate locations. For example, a surgeon may obtain by biopsy a tissue sample from a cancer patient's tumor and then send the tissue sample to a pathology lab, and a technician in the lab may fix the tissue sample and then prepare one or more slides, each with a single tissue section, for the assay. The slide(s) may be assayed soon after preparation, or stored for future assay. The lab that prepared a tissue section may conduct the assay or send the slide(s) to a different lab to conduct the assay. A technician who scores the slide(s) for a gene signature may work for the diagnostic lab, or may be an independent contractor. Alternatively, a single diagnostic lab obtains the tissue sample from the subject's physician or surgeon and then performs all of the steps involved in preparing tissue sections, assaying the slide(s) and calculating the gene signature score for the tissue section(s).

In some embodiments, the individuals involved with preparing and assaying the tissue section for a gene signature or gene signature biomarker do not know the identity of the subject whose sample is being tested; i.e., the sample received by the laboratory is made anonymous in some manner before being sent to the laboratory. For example, the sample may be merely identified by a number or some other code (a "sample ID") and the results of the assay are reported to the party ordering the test using the sample ID. In preferred embodiments, the link between the identity of a subject and the subject's tissue sample is known only to the individual or to the individual's physician.

In some embodiments, after the test results have been obtained, the diagnostic laboratory generates a test report, which may comprise any one or both of the following results: the tissue sample was biomarker positive or negative, the gene signature score for the tumor sample and the reference score for that gene signature. The test report may also include a list of genes whose expression was analyzed in the assay.

In other embodiments, the test report may also include guidance on how to interpret the results for predicting if a subject is likely to respond to a PD-1 antagonist. For example, in one embodiment, it the tested tumor sample is from a melanoma and has a gene signature score that is at or above a prespecified threshold, the test report may indicate that the subject has a score that is associated with response or better response to treatment with the PD-1 antagonist, while if the gene signature score is below the threshold, then the test report indicates that the patient has a score that is associated with no response or poor response to treatment with the PD-1 antagonist.

In some embodiments, the test report is a written document prepared by the diagnostic laboratory and sent to the patient or the patient's physician as a hard copy or via electronic mail. In other embodiments, the test report is generated by a computer program and displayed on a video monitor in the physician's office. The test report may also comprise an oral transmission of the test results directly to the patient or the patient's physician or an authorized employee in the physician's office. Similarly, the test report may comprise a record of the test results that the physician makes in the patient's file.

Assaying tumor samples for expression of the genes in a gene expression platform or gene signature described herein may be performed using a kit that has been specially designed for this purpose. In one embodiment, the kit comprises a set of oligonucleotide probes capable of hybridizing to the set of target transcripts listed in Table 1. In another embodiment, the kit comprises a set of oligonucleotide probes capable of hybridizing to the set of target transcripts listed in Table 1 for the genes in the 18 Gene Up-Down Signature and for the normalization genes in Table 1C. The set of oligonucleotide probes may comprise an ordered array of oligonucleotides on a solid surface, such as a microchip, silica beads (such as BeadArray technology from Illumina, San Diego, Calif.), or a glass slide (see, e.g., WO 98/20020 and WO 98/20019). In some embodiments, the oligonucleotide probes are provided in one or more compositions in liquid or dried form.

Oligonucleotides in kits of the invention are capable of specifically hybridizing to a target region of a polynucleotide, such as for example, an RNA transcript or cDNA generated therefrom. As used herein, specific hybridization means the oligonucleotide forms an anti-parallel double-stranded structure with the target region under certain hybridizing conditions, while failing to form such a structure with non-target regions when incubated with the polynucleotide under the same hybridizing conditions. The composition and length of each oligonucleotide in the kit will depend on the nature of the transcript containing the target region as well as the type of assay to be performed with the oligonucleotide and is readily determined by the skilled artisan.

In some embodiments, each oligonucleotide in the kit is a perfect complement of its target region. An oligonucleotide is said to be a "perfect" or "complete" complement of another nucleic acid molecule if every nucleotide of one of the molecules is complementary to the nucleotide at the corresponding position of the other molecule. While perfectly complementary oligonucleotides are preferred for detecting transcripts of the Table 1 genes, departures from complete complementarity are contemplated where such departures do not prevent the molecule from specifically hybridizing to the target region as defined above. For example, an oligonucleotide probe may have one or more non-complementary nucleotides at its 5' end or 3' end, with the remainder of the probe being completely complementary to the target region. Alternatively, non-complementary nucleotides may be interspersed into the probe as long as the resulting probe is still capable of specifically hybridizing to the target region.

In some preferred embodiments, each oligonucleotide in the kit specifically hybridizes to its target region under stringent hybridization conditions. Stringent hybridization conditions are sequence-dependent and vary depending on the circumstances. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. As the target sequences are generally present in excess, at Tm, 50% of the probes are occupied at equilibrium.

Typically, stringent conditions include a salt concentration of at least about 0.01 to 1.0 M sodium ion concentration (or other salts) at pH 7.0 to 8.3 and the temperature is at least about 25° C. for short oligonucleotide probes (e.g., 10 to 50 nucleotides). Stringent conditions can also be achieved with the addition of destabilizing agents such as formamide. For example, conditions of 5×SSPE (750 mM NaCl, 50 mM NaPhosphate, 5 mM EDTA, pH 7.4) and a temperature of 25-30° C. are suitable for allele-specific probe hybridizations. Additional stringent conditions can be found in Molecular Cloning: A Laboratory Manual, Sambrook et al., Cold Spring Harbor Press, Cold Spring Harbor, N.Y. (1989), chapters 7, 9, and 11, and in NUCLEIC ACID HYBRIDIZATION, A PRACTICAL APPROACH, Haymes et al., IRL Press, Washington, D.C., 1985.

One non-limiting example of stringent hybridization conditions includes hybridization in 4× sodium chloride/sodium citrate (SSC), at about 65-70° C. (or alternatively hybridization in 4×SSC plus 50% formamide at about 42-50° C.) followed by one or more washes in 1×SSC, at about 65-70° C. A non-limiting example of highly stringent hybridization conditions includes hybridization in 1×SSC, at about 65-70° C. (or alternatively hybridization in 1×SSC plus 50% formamide at about 42-50° C.) followed by one or more washes in 0.3×SSC, at about 65-70° C. A non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Stringency conditions with ranges intermediate to the above-recited values, e.g., at 65-70° C. or at 42-50° C. are also intended to be encompassed by the present invention. SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete.

The hybridization temperature for hybrids anticipated to be less than 50 base pairs in length should be 5-10° C. less than the melting temperature (T$_m$) of the hybrid, where Tm is determined according to the following equations. For hybrids less than 18 base pairs in length, T$_m$ (° C.)=2(# of A+T bases)+4(# of G+C bases). For hybrids between 18 and 49 base pairs in length, T$_m$ (° C.)=81.5+16.6(log$_{10}$[Na+])+ 0.41(% G+C)−(600/N), where N is the number of bases in the hybrid, and [Na+] is the concentration of sodium ions in the hybridization buffer ([Na+] for 1×SSC=0.165 M).

The oligonucleotides in kits of the invention may be comprised of any phosphorylation state of ribonucleotides, deoxyribonucleotides, and acyclic nucleotide derivatives, and other functionally equivalent derivatives. Alternatively, the oligonucleotides may have a phosphate-free backbone, which may be comprised of linkages such as carboxymethyl, acetamidate, carbamate, polyamide (peptide nucleic acid (PNA)) and the like (Varma, in MOLECULAR BIOLOGY AND BIOTECHNOLOGY, A COMPREHENSIVE DESK REFERENCE, Meyers, ed., pp. 6 17-20, VCH Publishers, Inc., 1995). The oligonucleotides may be prepared by chemical synthesis using any suitable methodology known in the art, or may be derived from a biological sample, for example, by restriction digestion. The oligonucleotides may contain a detectable label, according to any technique known in the art, including use of radiolabels, fluorescent labels, enzymatic labels, proteins, haptens, antibodies, sequence tags and the like. The oligonucleotides in the kit may be manufactured and marketed as analyte specific reagents (ASRs) or may be constitute components of an approved diagnostic device.

Kits of the invention may also contain other reagents such as hybridization buffer and reagents to detect when hybridization with a specific target molecule has occurred. Detection reagents may include biotin- or fluorescent-tagged oligonucleotides and/or an enzyme-labeled antibody and one or more substrates that generate a detectable signal when acted on by the enzyme. It will be understood by the skilled artisan that the set of oligonucleotides and reagents for performing the assay will be provided in separate receptacles placed in the kit container if appropriate to preserve biological or chemical activity and enable proper use in the assay.

In other embodiments, each of the oligonucleotide probes and all other reagents in the kit have been quality tested for optimal performance in an assay designed to quantify tumor RNA expression levels, in an FFPE tumor section, of the genes in Table 1, or of the genes in a gene signature in Table 2 and the normalization genes in Table 1C. In some embodiments, the kit includes an instruction manual that describes how to calculate a gene signature score from the quantified RNA expression levels.

B. Pharmaceutical Compositions, Drug Products and Treatment Regimens

An individual to be treated by any of the methods and products described herein is a human subject diagnosed with a tumor, and a sample of the subject's tumor is available or obtainable to use in testing for the presence or absence of a gene signature biomarker derived using gene expression platform described herein.

The tumor tissue sample can be collected from a subject before and/or after exposure of the subject to one or more therapeutic treatment regimens, such as for example, a PD-1 antagonist, a chemotherapeutic agent, radiation therapy. Accordingly, tumor samples may be collected from a subject over a period of time. The tumor sample can be obtained by a variety of procedures including, but not limited to, surgical excision, aspiration or biopsy.

A physician may use a gene signature score as a guide in deciding how to treat a patient who has been diagnosed with a type of cancer that is susceptible to treatment with a PD-1 antagonist or other chemotherapeutic agent(s). Prior to initiation of treatment with the PD-1 antagonist or the other chemotherapeutic agent(s), the physician would typically order a diagnostic test to determine if a tumor tissue sample removed from the patient is positive or negative for a gene signature biomarker. However, it is envisioned that the physician could order a first or subsequent diagnostic tests at any time after the individual is administered the first dose of the PD-1 antagonist or other chemotherapeutic agent(s). In some embodiments, a physician may be considering whether to treat the patient with a pharmaceutical product that is indicated for patients whose tumor tests positive for the gene signature biomarker. For example, if the reported score is at or above a pre-specified threshold score that is associated with response or better response to treatment with a PD-1 antagonist, the patient is treated with a therapeutic regimen that includes at least the PD-1 antagonist (optionally in combination with one or more chemotherapeutic agents), and if the reported gene signature score is below a pre-specified threshold score that is associated with no response or poor response to treatment with a PD-1 antagonist, the patient is treated with a therapeutic regimen that does not include any PD-1 antagonist.

In deciding how to use the gene signature test results in treating any individual patient, the physician may also take into account other relevant circumstances, such as the stage of the cancer, weight, gender, and general condition of the patient, including inputting a combination of these factors and the gene signature biomarker test results into a model that helps guide the physician in choosing a therapy and/or treatment regimen with that therapy.

The physician may choose to treat the patient who tests biomarker positive with a combination therapy regimen that includes a PD-1 antagonist and one or more additional therapeutic agents. The additional therapeutic agent may be, e.g., a chemotherapeutic, a biotherapeutic agent (including but not limited to antibodies to VEGF, EGFR, Her2/neu, VEGF receptors, other growth factor receptors, CD20, CD40, CD-40L, GITR, CTLA-4, OX-40, 4-1BB, and ICOS), an immunogenic agent (for example, attenuated cancerous cells, tumor antigens, antigen presenting cells such as dendritic cells pulsed with tumor derived antigen or nucleic acids, immune stimulating cytokines (for example, IL-2, IFNα2, GM-CSF), and cells transfected with genes encoding immune stimulating cytokines such as but not limited to GM-CSF).

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin gamma1I and calicheamicin phiI1, see, e.g., Agnew, Chem. Intl. Ed. Engl., 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2, 2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel and doxetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; CPT-11; topoisomerase inhibitor RFS 2000; difluoromethylomithine (DMFO); retinoids such as retinoic acid; capecitabine; and pharmaceutically acceptable salts, acids or derivatives of any of the above. Also included are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene (Fareston); aromatase inhibitors that inhibit the enzyme aromatase, which regulates estrogen production in the adrenal glands, such as, for example, 4(5)-imidazoles, aminoglutethimide, megestrol acetate, exemestane, formestane, fadrozole, vorozole, letrozole, and anastrozole; and anti-androgens such as flutamide, nilutamide, bicalutamide, leuprolide, and goserelin; and pharmaceutically acceptable salts, acids or derivatives of any of the above.

Each therapeutic agent in a combination therapy used to treat a biomarker positive patient may be administered either alone or in a medicament (also referred to herein as a pharmaceutical composition) which comprises the therapeutic agent and one or more pharmaceutically acceptable carriers, excipients and diluents, according to standard pharmaceutical practice.

Each therapeutic agent in a combination therapy used to treat a biomarker positive patient may be administered simultaneously (i.e., in the same medicament), concurrently (i.e., in separate medicaments administered one right after the other in any order) or sequentially in any order. Sequential administration is particularly useful when the therapeutic agents in the combination therapy are in different dosage forms (one agent is a tablet or capsule and another agent is a sterile liquid) and/or are administered on different dosing schedules, e.g., a chemotherapeutic that is administered at least daily and a biotherapeutic that is administered less frequently, such as once weekly, once every two weeks, or once every three weeks.

In some embodiments, at least one of the therapeutic agents in the combination therapy is administered using the same dosage regimen (dose, frequency and duration of treatment) that is typically employed when the agent is used as monotherapy for treating the same cancer. In other embodiments, the patient receives a lower total amount of at least one of the therapeutic agents in the combination therapy than when the agent is used as monotherapy, e.g., smaller doses, less frequent doses, and/or shorter treatment duration.

Each therapeutic agent in a combination therapy used to treat a biomarker positive patient can be administered orally or parenterally, including the intravenous, intramuscular, intraperitoneal, subcutaneous, rectal, topical, and transdermal routes of administration.

A patient may be administered a PD-1 antagonist prior to or following surgery to remove a tumor and may be used prior to, during or after radiation therapy.

In some embodiments, a PD-1 antagonist is administered to a patient who has not been previously treated with a biotherapeutic or chemotherapeutic agent, i.e., is treatment-naïve. In other embodiments, the PD-1 antagonist is administered to a patient who failed to achieve a sustained response after prior therapy with a biotherapeutic or chemotherapeutic agent, i.e., is treatment-experienced.

A therapy comprising a PD-1 antagonist is typically used to treat a tumor that is large enough to be found by palpation or by imaging techniques well known in the art, such as MRI, ultrasound, or CAT scan. In some preferred embodiments, the therapy is used to treat an advanced stage tumor having dimensions of at least about 200 mm$^3$, 300 mm$^3$, 400 mm$^3$, 500 mm$^3$, 750 mm$^3$, or up to 1000 mm$^3$.

Selecting a dosage regimen (also referred to herein as an administration regimen) for a therapy comprising a PD-1 antagonist depends on several factors, including the serum or tissue turnover rate of the entity, the level of symptoms, the immunogenicity of the entity, and the accessibility of the target cells, tissue or organ in the individual being treated. Preferably, a dosage regimen maximizes the amount of the PD-1 antagonist that is delivered to the patient consistent with an acceptable level of side effects. Accordingly, the dose amount and dosing frequency depends in part on the particular PD-1 antagonist, any other therapeutic agents to be used, and the severity of the cancer being treated, and patient characteristics. Guidance in selecting appropriate doses of antibodies, cytokines, and small molecules are available. See, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602; Physicians' Desk Reference 2003 (Physicians' Desk Reference, 57th Ed); Medical Economics Company; ISBN: 1563634457; 57th edition (November 2002). Determination of the appropriate dosage regimen may be made by the clinician, e.g., using parameters or factors known or suspected in the art to affect treatment or predicted to affect treatment, and will depend, for example, the patient's clinical history (e.g., previous therapy), the type and stage of the cancer to be treated and biomarkers of response to one or more of the therapeutic agents in the combination therapy.

Biotherapeutic agents used in combination with a PD-1 antagonist may be administered by continuous infusion, or by doses at intervals of, e.g., daily, every other day, three times per week, or one time each week, two weeks, three weeks, monthly, bimonthly, etc. A total weekly dose is generally at least 0.05 μg/kg, 0.2 μg/kg, 0.5 μg/kg, 1 μg/kg, 10 μg/kg, 100 μg/kg, 0.2 mg/kg, 1.0 mg/kg, 2.0 mg/kg, 10 mg/kg, 25 mg/kg, 50 mg/kg body weight or more. See, e.g., Yang et al. (2003) *New Engl. J. Med.* 349:427-434; Herold et al. (2002) *New Engl. J. Med.* 346:1692-1698; Liu et al. (1999) *J. Neurol. Neurosurg. Psych.* 67:451-456; Portielji et al. (20003) *Cancer Immunol. Immunother.* 52:133-144.

In some embodiments that employ an anti-human PD-1 mAb as the PD-1 antagonist, the dosing regimen will comprise administering the anti-human PD-1 mAb at a dose of 1, 2, 3, 5 or 10 mg/kg at intervals of about 14 days (±2 days) or about 21 days (±2 days) or about 30 days (±2 days) throughout the course of treatment.

In other embodiments that employ an anti-human PD-1 mAb as the PD-1 antagonist, the dosing regimen will comprise administering the anti-human PD-1 mAb at a dose of from about 0.005 mg/kg to about 10 mg/kg, with intra-patient dose escalation. In other escalating dose embodiments, the interval between doses will be progressively shortened, e.g., about 30 days (±2 days) between the first and second dose, about 14 days (±2 days) between the second and third doses. In certain embodiments, the dosing interval will be about 14 days (±2 days), for doses subsequent to the second dose.

In certain embodiments, a subject will be administered an intravenous (IV) infusion of a medicament comprising any of the PD-1 antagonists described herein, and such administration may be part of a treatment regimen employing the PD-1 antagonist as a monotherapy regimen or as part of a combination therapy.

In one preferred embodiment of the invention, the PD-1 antagonist is nivolumab, which is administered intravenously at a dose selected from the group consisting of: 1 mg/kg Q2W, 2 mg/kg Q2W, 3 mg/kg Q2W, 5 mg/kg Q2W, 10 mg Q2W, 1 mg/kg Q3W, 2 mg/kg Q3W, 3 mg/kg Q3W, 5 mg/kg Q3W, and 10 mg Q3W.

In another preferred embodiment of the invention, the PD-1 antagonist is pembrolizumab, which is administered in a liquid medicament at a dose selected from the group consisting of 200 mg Q3W, 1 mg/kg Q2W, 2 mg/kg Q2W, 3 mg/kg Q2W, 5 mg/kg Q2W, 10 mg Q2W, 1 mg/kg Q3W, 2 mg/kg Q3W, 3 mg/kg Q3W, 5 mg/kg Q3W, and 10 mg Q3W or equivalents of any of these doses (e.g., a PK model of pembrolizumab estimates that the fixed dose of 200 mg Q3W provides exposures that are consistent with those obtained with 2 mg/kg Q3W). In some particularly preferred embodiments, pembrolizumab is administered as a liquid medicament which comprises 25 mg/ml pembrolizumab, 7% (w/v) sucrose, 0.02% (w/v) polysorbate 80 in 10 mM histidine buffer pH 5.5, and the selected dose of the medicament is administered by IV infusion over a time period of 30 minutes. The optimal dose for pembrolizumab in combination with any other therapeutic agent may be identified by dose escalation.

The present invention also provides a medicament which comprises a PD-1 antagonist as described above and a pharmaceutically acceptable excipient. When the PD-1 antagonist is a biotherapeutic agent, e.g., a mAb, the antagonist may be produced in CHO cells using conventional cell culture and recovery/purification technologies.

In some embodiments, a medicament comprising an anti-PD-1 antibody as the PD-1 antagonist may be provided as a liquid formulation or prepared by reconstituting a lyophilized powder with sterile water for injection prior to use. WO 2012/135408 describes the preparation of liquid and lyophilized medicaments comprising pembrolizumab, which are suitable for use in the present invention. In some preferred embodiments, a medicament comprising pembrolizumab is provided in a glass vial which contains about 50 mg of pembrolizumab.

These and other aspects of the invention, including the exemplary specific embodiments listed below, will be apparent from the teachings contained herein.

VI. Exemplary Specific Embodiments of the Invention

1. A method of deriving a gene signature biomarker that is predictive of an anti-tumor response to a PD-1 antagonist for at least one tumor type of interest, which comprises:
    (a) obtaining a pre-treatment tumor sample from each patient in a patient cohort diagnosed with the tumor type;
    (b) obtaining, for each patient in the cohort, an anti-tumor response value following treatment with the PD-1 antagonist;
    (c) measuring the raw RNA levels in each tumor sample for each gene in a gene expression platform,
    wherein the gene expression platform comprises a clinical response gene set of between about 50 and about 60 genes and a normalization gene set of about 10 to about 12 housekeeping genes, and wherein about 90% of the clinical response genes exhibit intratumoral RNA levels that are positively correlated with the anti-tumor response and about 10% of the clinical response genes exhibit intratumoral RNA levels that are negatively correlated with the anti-tumor response;
    (d) normalizing, for each tumor sample, each of the measured raw RNA levels for the clinical response genes using the measured RNA levels of the normalization genes;
    (e) weighting, for each tumor sample and each gene in a gene signature of interest, the normalized RNA expression levels using a pre-defined multiplication coefficient for that gene;
    (f) adding, for each patient, the weighted RNA expression levels to generate a gene signature score for each patient in the cohort; and
    (g) comparing the gene signature scores for all of the tumor samples and the anti-tumor response values for all of the patients in the cohort to select a cut-off for the gene signature score that divides the patient cohort to meet a target biomarker clinical utility criterion.

2. The method of embodiment 1, which further comprises designating any tumor sample of the tumor type that has a gene signature score that is equal to or greater than the selected cut-off as biomarker positive and designating any tumor sample of the tumor type that has a gene signature score that is below the selected cut-off as biomarker negative.

3. A method of testing a tumor sample removed from a patient diagnosed with a particular tumor type for the presence or absence of a gene signature biomarker of anti-tumor response of the tumor type to a PD-1 antagonist, which comprises:
    (a) measuring the raw RNA level in the tumor sample for each gene in a gene expression platform, wherein the gene expression platform comprises a clinical response gene set of between about 50 and about 60 genes and a normalization gene set of about 10 to about 12 housekeeping genes, and wherein about 90% of the clinical response genes exhibit intratumoral RNA levels that are positively correlated with the anti-tumor response and about 10% of the clinical response genes exhibit intratumoral RNA levels that are negatively correlated with the anti-tumor response;
    (b) normalizing the measured raw RNA level for each clinical response gene in a pre-defined gene signature for the tumor type using the measured RNA levels of the normalization genes, wherein the pre-defined gene signature consists of at least 2 of the clinical response genes; (c) weighting each normalized RNA value using a pre-defined multiplication co-efficient; (d) adding the weighted RNA expression levels to generate a gene signature score; (e) comparing the generated score to a reference score for the gene signature and tumor type; and
    (f) classifying the tumor sample as biomarker positive or biomarker negative;
    wherein if the generated score is equal to or greater than the reference score, then the tumor sample is classified as biomarker positive, and if the generated score is less than the reference score, then the tumor sample is classified as biomarker negative.

4. A system for testing a tumor sample removed from a patient diagnosed with a particular tumor type for the presence or absence of a gene signature biomarker of anti-tumor response of the tumor type to a PD-1 antagonist, which comprises
    (i) a sample analyzer for measuring raw RNA expression levels of each gene in a gene expression platform, wherein the gene expression platform consists of a set of clinical response genes and a set of normalization genes, and
    (ii) a computer program for receiving and analyzing the measured RNA expression levels to
        (a) normalize the measured raw RNA level for each clinical response gene in a pre-defined gene signature for the tumor type using the measured RNA levels of the normalization genes;
        (b) weight each normalized RNA value using a pre-defined multiplication co-efficient;
        (c) add the weighted RNA expression levels to generate a gene signature score;
        (d) compare the generated score to a reference score for the gene signature and tumor type; and
        (e) classify the tumor sample as biomarker positive or biomarker negative, wherein if the generated score is equal to or greater than the reference score, then the tumor sample is classified as biomarker positive, and if the generated score is less than the reference score, then the tumor sample is classified as biomarker negative.

5. The method or system of any of the above embodiments, wherein the gene expression platform comprises at least 40, 45, 50 or 55 of the clinical response genes in Table 1 and one or more additional clinical response genes that are not in Table 1.

6. The method or system of any of the above embodiments, wherein the clinical response gene set comprises any number between 55 and 57 of the clinical response genes in Table 1 and the normalization gene set comprises at least 9 of the normalization genes in Table 1 and at least one housekeeping gene that is not in Table 1.

7. The method or system of any of the above embodiments, wherein the clinical response gene set consists of the 57 clinical response genes in Table 1A and Table 1B.

8. The method or system of any of the above embodiments, wherein the normalization gene set consists of the genes in Table 1C.

9. The method or system of any of the above embodiments, wherein the anti-tumor response value is selected from the group consisting of partial response, complete response, best overall response, duration of progression free survival, duration of disease free survival, objective response rate and median overall survival.

10. The method or system of any of the above embodiments, wherein the anti-tumor response value is a partial response or a complete response as measured by RECIST 1.1 or irRC.

11. The method or system of any of the above embodiments, the anti-tumor response value is obtained after the patient has been treated with a number of doses of the PD-1 antagonist selected from the group consisting of 2, 3, 4, 5, 6, 7, 8, 9, and 10.

12. The method or system of any of the above embodiments, wherein the PD-1 antagonist is nivolumab, pembrolizumab, a pembrolizumab biosimilar or a pembrolizumab variant.

13. The method or system of any of the above embodiments, wherein the anti-tumor response value is obtained following administration of at least four 200 mg doses of pembrolizumab every Q3W.

14. The method or system of any of the above embodiments, wherein the gene signature of interest or pre-defined gene signature is selected from the gene signatures listed in Table 2.

15. The method or system of any of the above embodiments, wherein the tumor type is bladder cancer, breast cancer, clear cell kidney cancer, head/neck squamous cell carcinoma, lung squamous cell carcinoma, malignant melanoma, non-small-cell lung cancer (NSCLC), ovarian cancer, pancreatic cancer, prostate cancer, renal cell cancer, small-cell lung cancer (SCLC), liposarcoma, triple negative breast cancer, acute lymphoblastic leukemia (ALL), acute myeloid leukemia (AML), chronic lymphocytic leukemia (CLL), chronic myeloid leukemia (CML), diffuse large B-cell lymphoma (DLBCL), EBV-positive DLBCL, primary mediastinal large B-cell lymphoma, T-cell/histiocyte-rich large B-cell lymphoma, follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin's lymphoma (NHL), Burkitt's lymphoma or small lymphocytic lymphoma (SLL).

16. The method or system of any of the above embodiments, wherein the tumor type is bladder cancer, colorectal cancer, gastric cancer, head and neck cancer, melanoma, non-small cell lung cancer, ovarian cancer, prostate cancer or renal cancer.

17. The method or system of any of the above embodiments, wherein the tumor type is bladder cancer, gastric cancer, head and neck cancer or melanoma.

18. The method or system of any of the above embodiments, wherein the clinical response gene set consists of the 57 clinical response genes in Table 1A and Table 1B, the normalization gene set consists of the genes in Table 1C or Table 1D and the pre-defined multiplication co-efficient for each clinical response gene is (i) the whole number 1 or (ii) the corresponding scoring weight shown in Set 1.1, Set 1.2, Set 2.1, Set 2.2, Set 2.3 and Set 2.4 in Table 3A.

19. A method of testing a tumor sample removed from a patient to generate a signature score for a gene signature that is correlated with an anti-tumor response to a PD-1 antagonist, wherein the method comprises:

(a) measuring the raw RNA level in the tumor sample for each gene in the gene signature, wherein the gene signature is selected from the group consisting of the 14-Gene Up-Down Signature and the 18-Gene Up-Down Signature set forth in Table 3B;

(b) normalizing the measured raw RNA level for each gene in the selected signature using the measured RNA levels of the normalization genes set forth in Table 1C;

(c) multiplying each normalized RNA value by the corresponding scoring weight set forth in Table 3B for the selected signature to generate a weighted RNA expression value; and (d) adding the weighted RNA expression values to generate the gene signature score.

20. The method of embodiment 18 or 19, wherein the PD-1 antagonist is nivolumab, pembrolizumab, a pembrolizumab biosimilar or a pembrolizumab variant.

21. The method of any of embodiments 18 to 20, wherein the anti-tumor response is progression free survival, partial response or complete response.

22. The method of any of embodiments 18 to 21, wherein the tumor sample is from a cancer selected from the group consisting of anal cancer, biliary cancer, bladder cancer, colorectal cancer, esophageal cancer, gastric cancer, head and neck cancer, ovarian cancer and triple negative breast cancer.

23. The method of embodiment 22, wherein the cancer progressed after the patient had been treated with a therapy other than a PD-1 antagonist.

24. The method or system of any of embodiments 1 to 23, wherein the PD-1 antagonist is pembrolizumab.

25 A kit for quantifying expression of genes in a gene signature, wherein the kit comprises a set of oligonucleotide probes capable of hybridizing to a set of target transcripts selected from the group consisting of:

(a) the target transcripts listed in Tables 1A, 1B and 1C
(b) the target transcripts listed in Table 2.1 below

TABLE 2.1

| 18 Gene Up-Down Signature | | |
|---|---|---|
| Gene Symbol | Accession No. | Target Transcript |
| CCL5 | NM_002985.2 | 280-380 |
| CD27 | NM_001242.4 | 330-430 |
| CD274 | NM_014143.3 | 1245-1345 |
| CD276 | NM_001024736.1 | 2120-2220 |
| CD8A | NM_001768.5 | 1320-1420 |
| CMKLR1 | NM_004072.1 | 770-870 |
| CXCL9 | NM_002416.1 | 1975-2075 |
| CXCR6 | NM_006564.1 | 95-195 |
| HLA.DQA1 | NM_002122.3 | 261-361 |
| HLA.DRB1 | NM_002124.1 | 985-1085 |
| HLA.E | NM_005516.4 | 1204-1304 |
| IDO1 | NM_002164.3 | 50-150 |
| LAG3 | NM_002286.5 | 1735-1835 |
| NKG7 | NM_005601.3 | 632-732 |
| PDCD1LG2 | NM_025239.3 | 235-335 |
| PSMB10 | NM_002801.2 | 221-321 |
| STAT1 | NM_007315.2 | 205-305 |
| TIGIT | NM_173799.2 | 1968-2068 |
| Normalization Genes | | |
| Gene Symbol | Accession No. | Target Region |
| ABCF1 | NM_001090.2 | 850-950 |
| C14ORF102 | NM_017970.3 | 3236-3336 |
| G6PD | NM_000402.2 | 1155-1255 |

TABLE 2.1-continued

| | | |
|---|---|---|
| OAZ1 | NM_004152.2 | 313-413 |
| POLR2A | NM_000937.2 | 3775-3875 |
| SDHA | NM_004168.1 | 230-330 |
| STK11IP | NM_052902.2 | 565-665 |
| TBC1D10B | NM_015527.3 | 2915-3015 |
| TBP | NM_001172085.1 | 587-687 |
| UBB | NM_018955.2 | 795-895 |
| ZBTB34 | NM_001099270.1 | 406-506 |

EXAMPLES

Example 1. Isolation of Total RNA from FFPE Tissue and Subsequent Gene Expression Analysis Using the NanoString nCounter™ System This example describes the methods used to analyze gene expression in the FFPE tumor samples discussed in the Examples below. Total RNA was isolated from slides of FFPE tissue for analysis on the NanoString nCounter™ gene expression platform (NanoString Technologies, Seattle, Wash.). Prior to RNA extraction, the entire tissue section was macrodissected/scraped from the slide and transferred to a 1.5 mL labeled Eppendorf tube containing 200 μL of 100% ethanol. A fresh scalpel was used for each sample to avoid the possibility of cross-contamination. Samples were then deparaffinized and digested with Protease using the recommended protocol in the Ambion® RecoverAll™ Total Nucleic Acid Isolation Kit for FFPE tissue (Cat no. AM1975). Total RNA extraction was performed using the above mentioned Ambion RecoverAll™ kit (Cat no. AM1975) and by following the manufacturer's recommended instructions. The total RNA was stored at −80° C. until gene expression profiling was performed using the NanoString nCounter™ system.

Example 2. Construction of a Preferred Gene Expression Platform of the Invention The inventors herein selected the 57 clinical response genes for the gene expression platform shown in Table 1 based on an accumulation of evidence that this set of genes is capable of predicting clinical outcome of different tumor types to treatment with pembrolizumab.

The genes were identified from a discovery set of 680 genes (657 candidate clinical response genes and 23 housekeeping genes). The candidate clinical response genes were derived from the following sources: 1) genes from an immune signature with co-expression to PD-L1 derived from a gene expression database for a large set of human tumors; 2) genes known to be involved in T cell biology, immune regulation, cellular markers of tumor-infiltrating lymphocytes (TILs) and tumor-associated macrophages (TAMs); and 3) signatures from syngeneic tumor mouse models with response to treatment with a mouse anti-mouse PD-1 mAb. A codeset of probes for assaying gene expression of this 680 discovery gene set in tumor samples was obtained from Nanostring.

Analysis of pre-treatment gene expression levels of the 680 discovery set in tumor samples of a melanoma cohort resulted in the generation of three gene signatures, termed the "PD-L1", "IFNg", and "Expanded Immune" signatures, which showed a statistically significant association with an anti-tumor response to pembrolizumab. Confirmatory hypothesis testing in a second melanoma cohort demonstrated that each of these three signatures showed statistically significant associations with anti-tumor response treatment with pembrolizumab.

Further analysis of the 680-gene discovery gene set indicated that genes involved in antigen presentation and T-cell receptor (TCR) signaling seemed to be some of the most predictive features in melanoma samples, achieving low false discovery rates (FDR) for some of the clinical endpoints. These findings were used to define additional signatures to be added to the previous three signatures for further testing in an independent set of head & neck (H&N) pre-treatment tumor samples from a patient cohort participating in a clinical trial of pembrolizumab.

Prior to testing the H&N tumor samples, the previously defined gene signatures ("PD-L1", "IFNg", and "Expanded" immune) were refined, by removing some individual genes that were not found to be contributing to the ability predict an anti-tumor response of melanoma patients. After this refinement, these three signatures consisted of the genes shown in the corresponding columns of Table 2 above. The primary objective for the H&N study was to further test for associations between anti-tumor response and the refined gene signatures. Hypothesis testing in an independent set of H&N tumors confirmed that all of these signatures were predictors of anti-tumor responses to pembrolizumab, as shown in Table 4 below.

TABLE 4

Hypothesis testing results for 4 of the gene signatures listed in Table 2 in head & neck cancer

| | Nominal One-sided P-value[a] | | |
|---|---|---|---|
| Signature | Tumor 1D Shrinkage<br>N = 43 | BOR<br>N = 39 | PFS<br>N = 40 |
| TCR Signaling | 0.154 | 0.065 | 0.003 |
| PD-L1 | 0.047 | 0.025 | 0.002 |
| IFNg | 0.004 | 0.009 | <0.001 |
| Expanded Immune | 0.016 | 0.032 | <0.001 |

[a]From one-sided test on Kendall's tau for tumor shrinkage or from logistic regression for best overall response or a Cox regression for PFS.

Analysis of the individual member genes of these four pre-specified gene signatures as well as in the set of 657 candidate clinical response genes in the 680 gene discovery set showed some very low estimated false discovery rates for a number of genes in head and neck cancer. The inventors herein thus set out to capture additional highly associated genes, by using pre-treatment gene expression data for other tumor types and anti-tumor response data following pembrolizumab treatment.

Initially, the inventors identified a set of 51 genes for a prototype clinical response gene set using pre-treatment gene expression and post-treatment response data from only melanoma and head and neck cohorts. These 51 genes were obtained in the following manner. Genes were selected by taking the union of all genes that showed a positive association with clinical outcome that either:

1. Achieved an estimated FDR≤25% across the discovery gene set for H&N for all three of the following clinical outcome measures: maximum % tumor shrinkage, best overall response (BOR), and PFS; or
2. Achieved an estimated FDR≤33% across the discovery gene set for Melanoma for all three of the following clinical outcome measures: BOR, PFS, and OS; or
3. Were included in the PD-L1, IFNg, Expanded Immune, or TCR Signaling signatures as shown in Table 2.

This preliminary set of 51 genes was then tested as a pre-specified clinical response gene set in bladder and gastric cancer cohorts, and was found to be markedly different than the remainder of the genes in the discovery gene set in terms of the statistical significance of the associations.

Having confirmed that a highly predictive gene set of clinical response genes had been identified, a meta-analysis exercise was undertaken to refine this set using pre-treatment gene expression and clinical response data from three tumor types treated with pembrolizumab: gastric, bladder, and head and neck. Focusing on PFS as the measure of anti-tumor response, using the head and neck, bladder, and gastric cohorts, a meta-analysis of the entire 680-gene discovery platform was conducted that pooled the data from these cohorts together to understand the most associated genes. The final gene set of clinical response genes was obtained by 1) first removing 10 genes that were part of the preliminary 51-gene list that did not show up among the top 100 most associated features, by p-value ranking, from the meta-analysis and were also not the gene B2M or a member gene of any of the signatures in Table 2 (signatures that had been identified by the time of testing in the gastric cohort) and 2) adding in 16 new predictive genes identified by the multivariate analysis across all three indications.

Thus, a final set of 57 genes was identified, to which 11 house-keeping genes were added to yield the 68-gene expression platform shown in Table 1.

The presence of an anti-correlated gene subset in the clinical response gene set is intended to serve two roles: as potential members of a gene signature and as a control to check that key immune patterns that are associated with anti-tumor response to a PD-1 antagonist are behaving as expected. The utility of this control function was evaluated by conducting an unsupervised clustering analysis of the gene expression patterns for the negatively-correlated gene subset listed in Table 1B and the MIPFS 7-gene signature listed in Table 2 in a Head & Neck cancer cohort. The results are shown in FIG. 1. The potential utility of this platform to derive gene signatures and gene signature biomarkers for other tumor types was investigated by analyzing the covariance patterns for normalized RNA expression levels of all of the Table 1 clinical response genes, or a subset of 37 of those genes, in 69 melanoma tumors against multiple tumors of other cancer types. The number of patient tumor samples and Table 1 clinical response genes analyzed are shown in Table 5 below. The 37 gene subset consisted of: CCL5, CCR5, CD2, CD27, CD274, CD276, CD3E, CD3G, CD4, CTAG1B, CXCL10, CXCL9, EGFR, GRAP2, GZMB, GZMK, HLA-DRA, HLA-E, IDO1, IFNG, IKZF3, IL10R, IL2RB, IL2RG, IRF8, LAG3, LCK, P2RY8, PDCD1LG2, PSMB10, SLC2A1, STAT1, TIGIT, TNFRSF14, TNFSF13B, TSLP and ZAP70. RNA expression levels were normalized by the mean of the 11 normalization genes in Table 1.

TABLE 5

Assessment of Covariance of RNA Expression Levels for Clinical Response Genes in Melanoma versus Other Tumor Types

| Other Tumor Type | Number of Tumor Samples | Number of Clinical Response Genes |
| --- | --- | --- |
| Head & Neck Cancer | 43 | 57 |
| Bladder Cancer | 29 | 57 |
| Gastric Cancer | 33 | 57 |
| Non-Small Cell Lung Cancer | 58 | 37 |
| Colorectal Cancer | 55 | 37 |
| Renal Cancer | 66 | 37 |
| Prostate Cancer | 28 | 57 |
| Ovarian Cancer | 48 | 37 |
| Triple Negative Breast Cancer | 108 | 57 |

As demonstrated in FIGS. 2A to 2I, the covariance patterns were largely preserved for the Table 1 clinical response genes that were examined.

Example 3. Model-Based Derivation of Gene Signature Scores Using the Gene Expression Platform of Table 1

Figure 3:
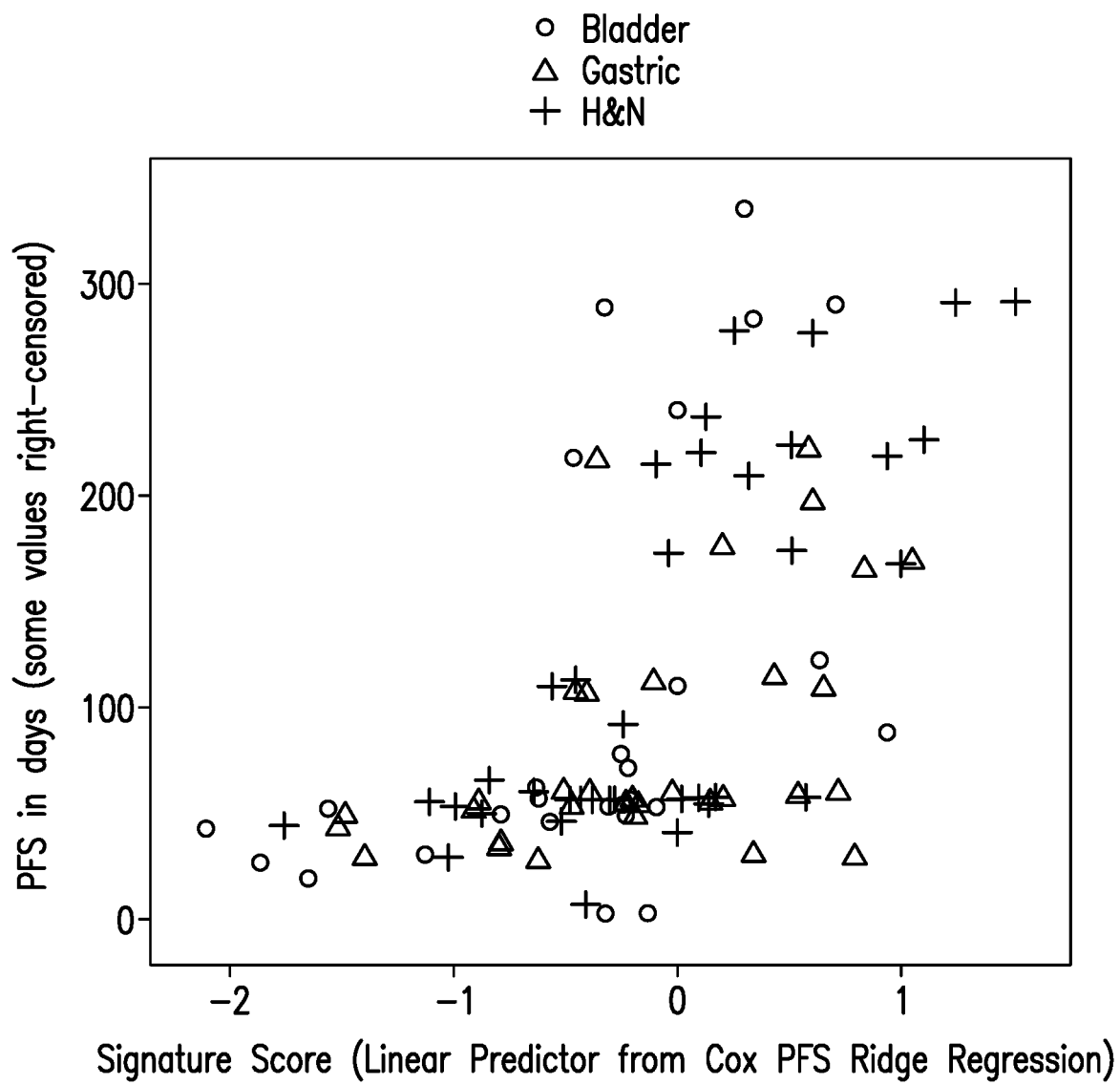
FIG. 3 shows model-derived gene signature scores determined for a gene signature of the 57 clinical response genes in Table 1 plotted against progression free survival time in a Meta-analysis of pre-treatment tumor samples and clinical response data in three different cancer cohorts treated with pembrolizumab.

A Cox PFS elastic net meta-analysis was conducted on post-treatment PFS times and normalized pre-treatment intra-tumoral RNA expression levels of the 57 clinical response gene set in Table 1 for 40 head and neck cancer patients, 29 bladder cancer patients, and 33 gastric cancer patients. The L1 penalty was set at 0.001 to include all 57 clinical response genes in the model (effectively a ridge regression) and cross-validation was used to select the value of the L2 penalty. The model included coefficients for each of the 57 genes in addition to terms capturing indication specific differences in the PFS distribution and indication specific effects of patient performance status. Prior to fitting this regression, house-keeping normalized gene expression levels were centered by their mean and scaled by their standard deviation (within each cancer indication). The final signature score, plotted on the X-axis of FIG. 3, is the "linear predictor" of the hazard function from the cross-validated fit: effectively a linear combination of the house-keeping normalized genes (centered and scaled), where the weighting is specified by the estimated model coefficients for the 57 genes (and the indication specific model terms, which are necessary for plotting different indications in the same graph). FIG. 3 shows the model-derived gene signature scores for the patients used in the meta-analysis plotted against their PFS times.

Figure 4:
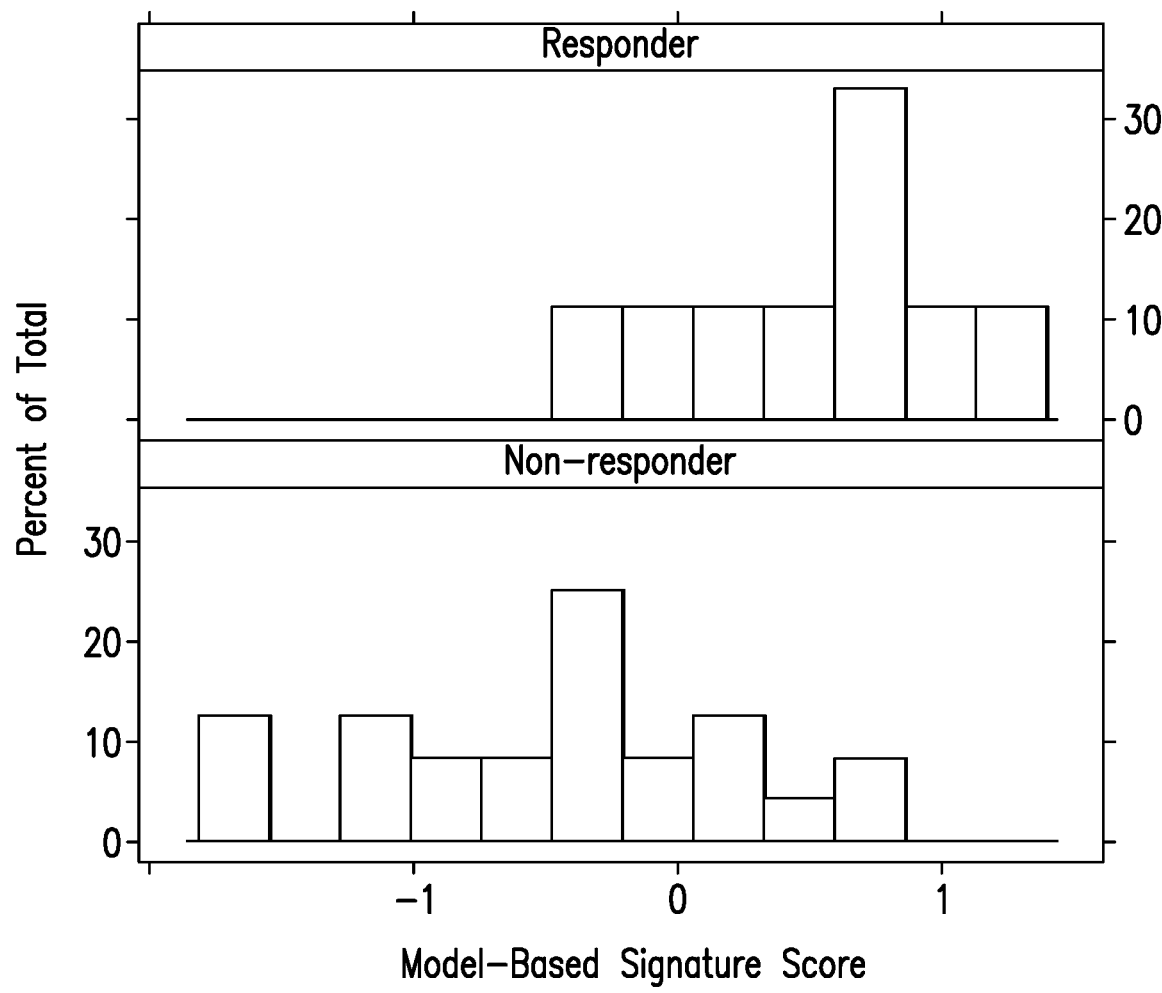
FIG. 4 shows a histogram of the percent of responder and non-responder patients in a gastric cancer cohort treated with pembrolizumab plotted against model-derived gene signature scores determined for pre-treatment tumor samples for the 57 clinical response genes listed in Table 1.

The gene signature scores derived above for the gastric cohort were also compared by responder status in the cohort, and the results are shown in FIG. 4.

Figure 5:
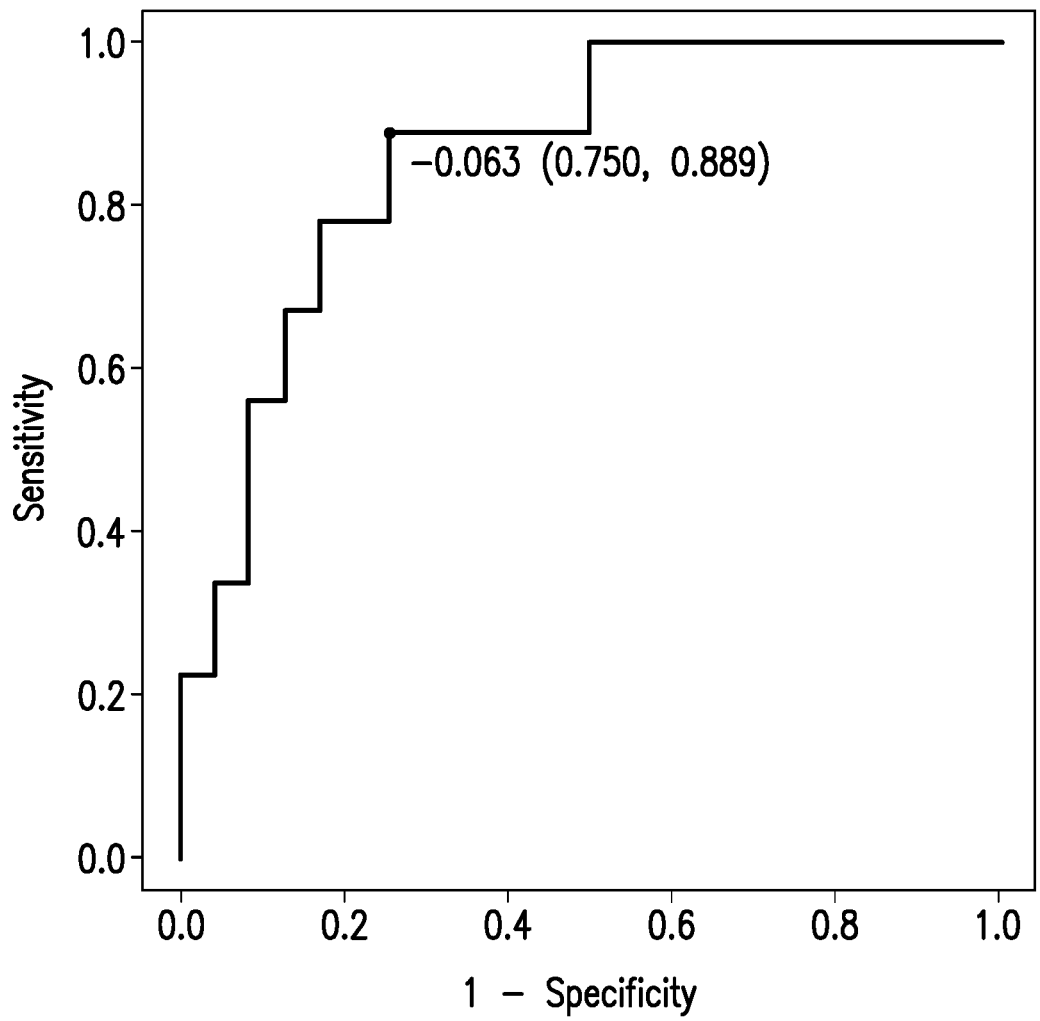
FIG. 5 shows an ROC curve of the model-based gene signature scores shown in FIG. 4.

FIG. 5 shows the ROC curve for potential cut-offs for this model-based gene signature in this gastric cancer cohort. The area under the ROC curve is 0.86 and the statistics associated with the Youden Index (labeled on the curve) based cut-off are: PPV of 57%, NPV of 95%, and prevalence above cut-off of 42%.

The linear combination of the 57 genes specified by the model fit could then be used within each indication to select an appropriate cut-off by estimating a clinical utility profile using one of the anti-tumor response measures or via receiver operating characteristic (ROC) curves as discussed below in Example 4.

Once estimated using such a model-based approach, the weights for each gene in a gene signature may be used as part of a system to calculate gene signature scores for future patients without re-fitting the model, i.e. the weights are considered fixed.

Figure 6:
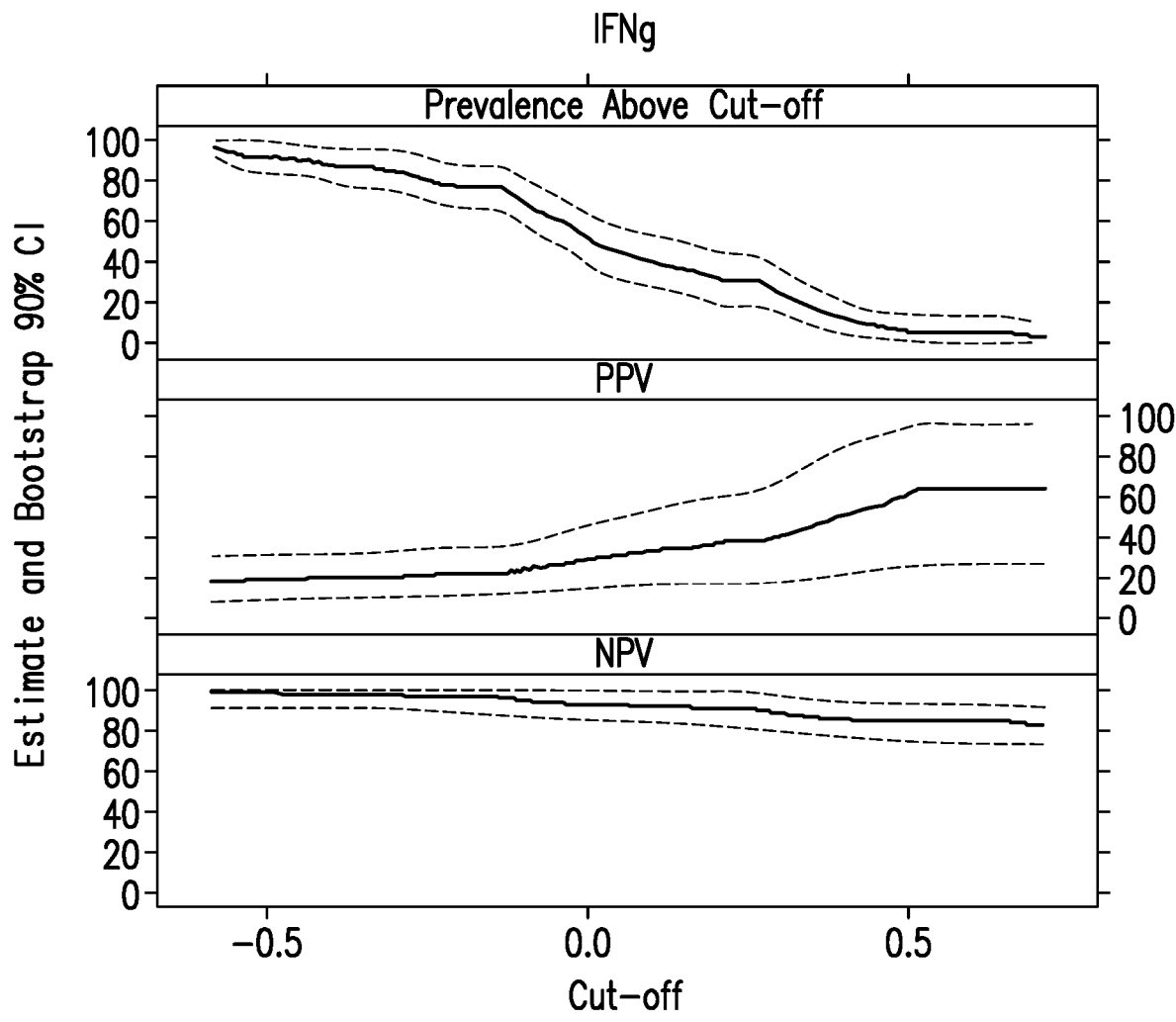
FIG. 6 illustrates the potential utility of an IFNg gene signature represented in Table 1 for predicting BOR to pembrolizumab of patients in a head & neck cohort, showing the effect of increasing cut-off scores on prevalence of patients in the cohort having gene signature scores above the cut-off (top panel), positive predictive value (PPV, middle panel) and negative predictive value (NPV, lower panel).

Example 4. Derivation of a Cut-Off on Gene Signature Scores Derived from the Gene Expression Platform of the Invention FIG. 6 shows the estimated clinical diagnostic utility profile of gene signature scores for the IFNg signature in head & neck cancer using best overall response (BOR) as the anti-tumor response value as a potential cut-off is set to larger and larger values. The empirical distribution of the IFNg signature scores in combination with a logistic regression model describing the probability of response given signature score was used to calculate the profile for PPV (the response rate in the patients with signature scores≥the cut-off), NPV (the non-response rate in the patients with signature scores<cut-off), and prevalence of patients signature scores≥the cut-off. This profile can be used to understand the implications of selecting a given cut-off. So, for example, the clinical utility profile of the IFNg gene signature score suggests that a cut-off of ~0.3 would achieve ~90% NPV, ~40% PPV, and result in a biomarker high subgroup prevalence of ~25% of H/N patients. Alternatively, a cut-off of ~0.10 would achieve ~92% NPV, ~33% PPV, and a biomarker high subgroup prevalence of ~40%. ROC curve analysis may be combined with this assessment of clinical utility to help select a cut-off and understand sensitivity and specificity for selecting responders and excluding non-responders for treatment with a PD-1 antagonist.

This example demonstrates how a gene signature, such as the IFNg gene signature listed in Table 2, can be utilized to create scores and set cut-offs that distinguish whether or not a cancer patient is more likely to benefit from treatment with a PD-1 antagonist. A model-based gene signature score as described in Example 3 could also be the input to such a utility analysis.

Example 5. Derivation of Exemplary Scoring Methods for the Gene Expression Platform of Table 1

This example describes the derivation and utility of the two sets of signature scoring weights listed in Table 3. Each scoring weight set had overlapping cancer histologies included in its respective meta-analyses. For both sets, the input to the scoring method was the set of normalized RNA expression levels of the 57 individual clinical response genes in Table 1. The measured (e.g., raw) RNA expression values were normalized by performing a log(10) transformation of the measured raw RNA levels for each clinical response gene in the signature and for each normalization gene in Table 1C, calculating an arithmetic mean of the log 10 transformed RNA levels of the normalization genes, and subtracting the calculated mean from the log 10 transformed RNA levels for each clinical response gene, and these normalized values (without any further standardization within indication) were the input to the elastic net fitting. Additionally in all cases below, the elastic net model used included terms for the histology, baseline performance status, and the interaction between histology and baseline performance status (and the penalization applied under elastic net was also applied to these terms during model estimation).

The first set of scoring methods was derived using patients with head and neck (H&N) cancer, gastric cancer, and bladder cancer from MK-3475-012/KEYNOTE-012 (hereinafter KEYNOTE-012). This study is a phase 1b multi-cohort study which is investigating the safety, tolerability and anti-tumor activity of pembrolizumab (MK-3475) in patients with advanced triple negative breast cancer (TNBC) (Cohort A), H&N cancer (Cohorts B and B2), advanced urothelial cancer (Cohort C), or advanced gastric cancer (Cohort D). All of the patients used to derive this first set of scoring algorithms were treated with 10 mg/kg pembrolizumab, administered IV once every 2 weeks.

The second set of scoring methods was derived using patients with H&N cancer, gastric cancer, bladder, and triple negative breast cancer from KEYNOTE-012 and patients with anal cancer, biliary cancer, colorectal cancer, esophageal cancer, and ovarian cancer from MK-3475-028/KEYNOTE-028 (hereinafter KEYNOTE-028). KEYNOTE-028 is a phase 1b study designed to assess the efficacy and safety of pembrolizumab administered to participants with incurable advanced PD-L1-positive solid tumors. Patients in KEYNOTE-028 are treated with treated with 10 mg/kg pembrolizumab, administered IV once every 2 weeks.

Description of Scoring Set 1:

Set 1.1.

A linear combination derived under an elastic net fit that used a fixed low level of the L1 penalty in a Cox meta-analysis of progression free survival (PFS) with cross-validation to determine the L2 penalty. The regression coefficients from the final Cox PFS model fit at the selected values of the L1 and L2 penalties are multiplied to their respective genes and then the resulting weighted values are summed to create the signature score. These values of the regression coefficients, i.e. the weights, are listed under Set 1.1 in Table 3A.

Set 1.2.

A linear combination derived under an elastic net fit that used a fixed low level of the L1 penalty in a logistic regression meta-analysis of best overall response (BOR) with cross-validation to determine the L2 penalty. The regression coefficients from the final logistic model fit at the selected values of the L1 and L2 penalties are multiplied to the normalized RNA expression levels for their respective genes and then the resulting weighted values are summed to create the signature score. These values of the regression coefficients, i.e. the weights, are listed under Set 1.2 in Table 3A.

The regression coefficients in Set 1.1 and 1.2 were identified using three cancer cohorts from KEYNOTE-012 (H&N, gastric, and bladder). To test the hypothesis that these scoring weight sets could generate signature scores that are predictive of anti-tumor response to pembrolizumab, these scoring weight sets were applied to calculate signature scores from normalized RNA values, for the 57 gene signature, which had been determined for tumor samples removed from KEYNOTE-028 patients prior to pembrolizumab treatment. As shown in Table 6, the signature scores obtained using either scoring weight Set 1.1 or 1.2 were predictive in an independent set of patients from KEYNOTE-028 that had a variety of cancers. These results indicate that signature scores calculated using the scoring weights in Set 1.1 or Set 1.2 will have utility for deriving gene signature biomarkers for other cancer types.

TABLE 6

Statistical Significance of 57-gene signature scores in KEYNOTE-028 patients.

| | Nominal One-sided P-value[a] | | |
|---|---|---|---|
| Scoring Weight Set | BOR N = 92 | PFS N = 125 | OS N = 125 |
| Set 1.1 in Table 3A | 0.016 | 0.034 | 0.007 |
| Set 1.2 in Table 3A | 0.019 | 0.057 | 0.001 |
| Simple Averages (up minus down arms)[b] | 0.025 | 0.012 | 0.002 |

[a]From logistic regression for BOR and Cox regression for PFS and OS.
[b]The simple arithmetic average of the normalized expression values of the genes designated as being positively associated with clinical benefit minus the arithmetic average of those designated as being negatively associated with clinical benefit.

Scoring Set 1 was derived prior to the availability of clinical response data from KEYNOTE-028. To explore potential improvements to these weighting sets, additional scoring sets were identified and analyzed using all of the cancer types and clinical response data from KEYNOTE-012 and KEYNOTE-028. The clinical response data set from KEYNOTE-012 used in this analysis included data obtained after the patients had received more pembrolizumab doses than the clinical response data set used to derive Scoring Set 1. The scoring sets derived using this analysis are described below.

Description of Scoring Set 2:

Set 2.1.

A linear combination derived under an elastic net fit that used a fixed low level of the L1 penalty in a Cox progression free survival (PFS) meta-analysis and using cross-validation to determine the L2 penalty. The regression coefficients from the final Cox PFS model fit at the selected values of the L1 and L2 penalties are multiplied to the normalized RNA expression levels for their respective genes and then the resulting weighted values are summed to create the signature score. These values of the regression coefficients, i.e. the weights, are listed under Set 2.1 in Table 3A.

Set 2.2.

A linear combination derived under an elastic net fit that used a fixed low level of the L1 penalty in a logistic regression meta-analysis of best overall response and using cross-validation to determine the L2 penalty. The regression coefficients from the final logistic model fit at the selected values of the L1 and L2 penalties are multiplied to the normalized RNA expression levels for their respective genes and then the resulting weighted values are summed to create the signature score. These values of the regression coefficients, i.e. the weights, are listed under Set 2.2 in Table 3A.

Using a low level of the L1 penalty to derive scoring Sets 1.1, 1.2, 2.1 and 2.2 was intended to allow the expression levels for all of the 57 clinical response genes to be part of the signature score under the premise that most of the genes are expected to be associated with an anti-tumor response of multiple cancer types to treatment with pembrolizumab. An alternative strategy for identifying a robust "cross-histology" predictor of response is to further reduce the set of clinical response genes from Table 1 that are used in creating a signature score. This approach was applied to combined clinical response data for patients with multiple cancer types from KEYNOTE-012 and KEYNOTE-028 to search for specific subsets of the Table 1 clinical response genes, and signature scores therefor, that would show robustly predictive value across all of the studied cancer types. The approach is illustrated by the derivation of scoring weight sets 2.3 and 2.4 as described below.

Set 2.3.

A linear combination derived under an elastic net fit that used cross-validation to determine both the L1 and L2 penalties in a Cox progression free survival (PFS) meta-analysis. The regression coefficients from the final Cox PFS model fit at the selected values of the L1 and L2 penalties are multiplied to the normalized RNA expression levels for their respective genes and then the resulting weighted values are summed to create the signature score. These values of the regression coefficients, i.e. the weights, are listed under Set 2.3 in Table 3A and in the $2^{nd}$ column of Table 3B.

Set 2.4.

A linear combination derived under an elastic net fit that used cross-validation to determine both the L1 and L2 penalties in a logistic regression meta-analysis. The regression coefficients from the final logistic model fit at the selected values of the L1 and L2 penalties are multiplied to the normalized RNA expression levels for their respective genes and then the resulting weighted values are summed to create the signature score. These values of the regression coefficients, i.e. the weights, are listed under Set 2.4 in Table 3A and in the $3^{rd}$ column of Table 3B.

As is evident from inspection of the gene signatures in Table 3B, predominantly the same genes are retained by the PFS and BOR regressions that produced the weights of Set 2.3 and 2.4, respectively, showing that predominantly the same genes are selected using either clinical endpoint. The zero weights on the other clinical response genes should not be interpreted to mean that expression levels of these genes are not individually strongly associated with clinical outcome, only that they do not seem to add additional value beyond those with non-zero coefficients with regard to improving prediction in the penalized PFS regression meta-analysis setting when all the genes are competing simultaneously to demonstrate predictive value.

Example 6. Clinical Utility of Signature Scores Calculated Using Scoring Weight Sets To illustrate the clinical utility of signature scores generated using weighting coefficients, FIGS. 7 and 8 display estimates of the expected PPV and NPV profiles (averaging across indications) as a function of putative cut-offs on signature scores calculated using the Set 1.1 weights. These expected profiles were calculated using a hierarchical Bayesian meta-analysis of the combined KEYNOTE-028 and KEYNOTE-012 data, with the solid curve showing an estimate of the expected value of PPV (as captured by the posterior median) and the dotted lines above and below the curve indicating the upper and lower bounds of the 90% credible interval on the expected value.

Figure 7:
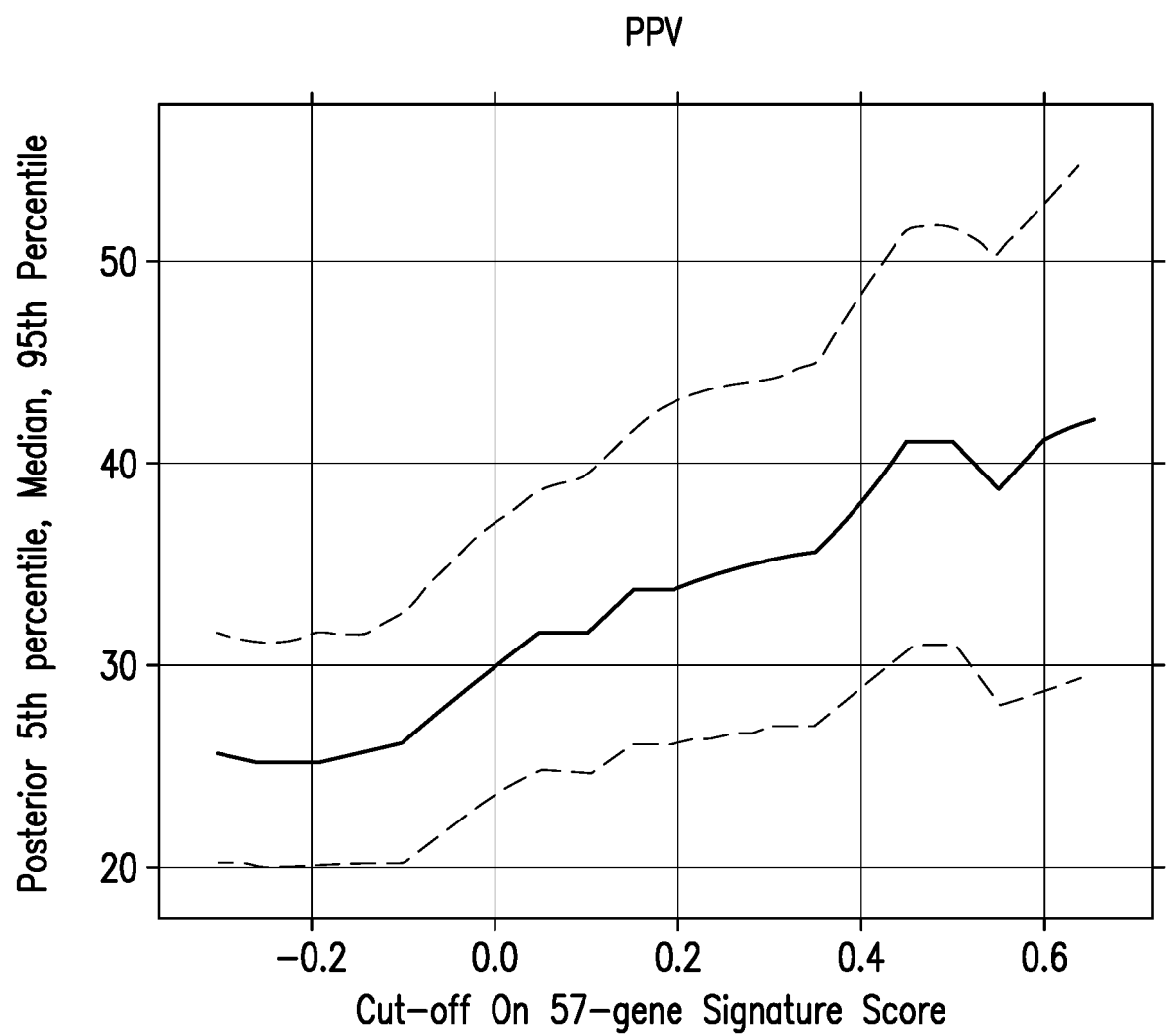
FIG. 7 shows the expected BOR PPV profile of signature scores for the 57-gene signature of Table 1, which scores were calculated using the weights of Set 1.1 under a hierarchical Bayesian meta-analysis of KEYNOTE-012 and KEYNOTE-028.
Figure 8:
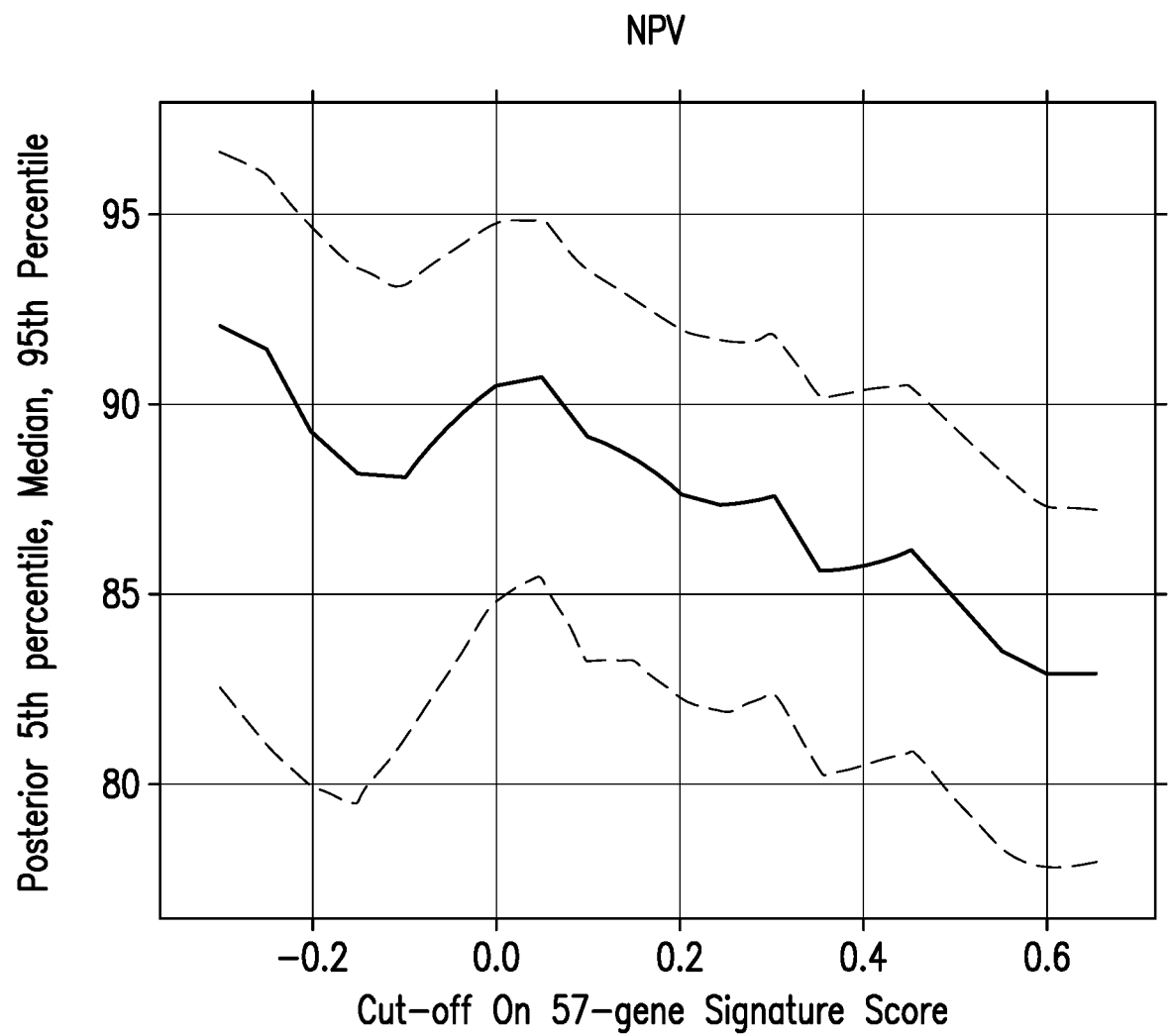
FIG. 8 shows the expected BOR NPV profile of signature scores for the 57-gene signature of Table 1, which scores were calculated using the weights of Set 1.1 under a hierarchical Bayesian meta-analysis of KEYNOTE-012 and KEYNOTE-028.

The PPV and NPV profiles in FIGS. 6 and 7 illustrate how the expected relationship between potential cut-off values of the signature score calculated using the Set 1.1 weights and clinical utility measures, such as PPV and NPV, implied by such cut-offs might be used to support selecting a minimum signature score as a cut-off for designating patients as biomarker positive. Such a cut-off could be applied in a pre-specified way to cancer indications for which no or little data has been gathered that relates gene expression levels to clinical response to therapy with a PD-1 antagonist. For example, the meta-analysis estimate of these expected clinical utility profiles suggests two general possibilities for a single cut-off score that is useful for multiple cancer types:

A "low" cut-off that favors NPV with an expected PPV near 30% while maintaining expected NPV near 90%.

A "high" cut-off that favors PPV with an expected PPV near 40% while maintaining expected NPV near 85%.

Each of the weighting sets listed in Table 3 could be used to conduct similar analysis of the clinical utility profile for one or more cancer types using the signature scores determined thereby.

Figure 9A:
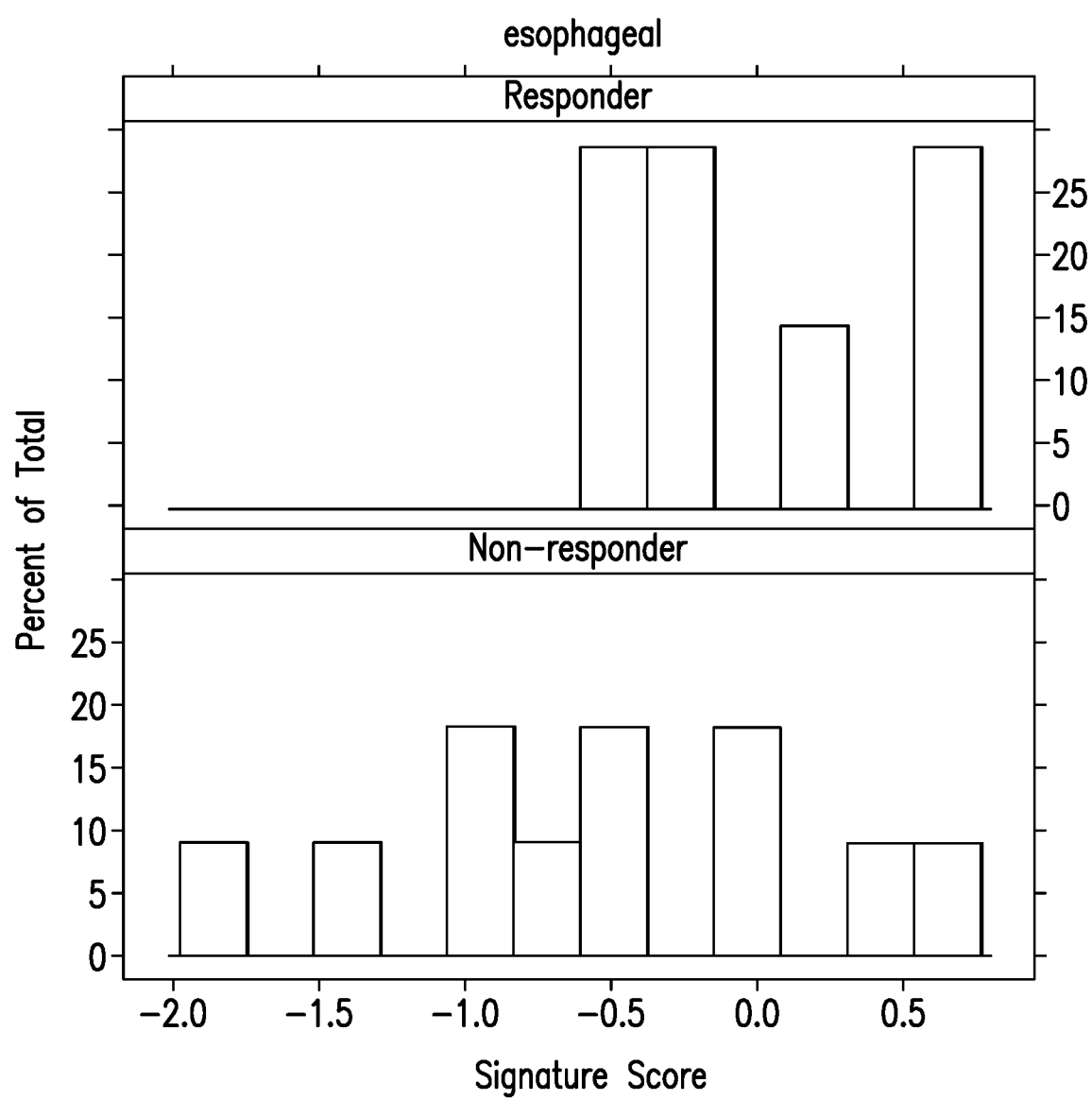
FIGS. 9A and 9B are histograms showing the distribution of pre-treatment signature scores for a 57 gene signature amongst esophageal cancer patients who responded (Responder) or did not respond (Non-responder) to pembrolizumab treatment, in which the signature scores were calculated using the exemplary scoring weight Set 1.1 (FIG. 9A) or Set 2.4 (FIG. 9B).
Figure 9B:
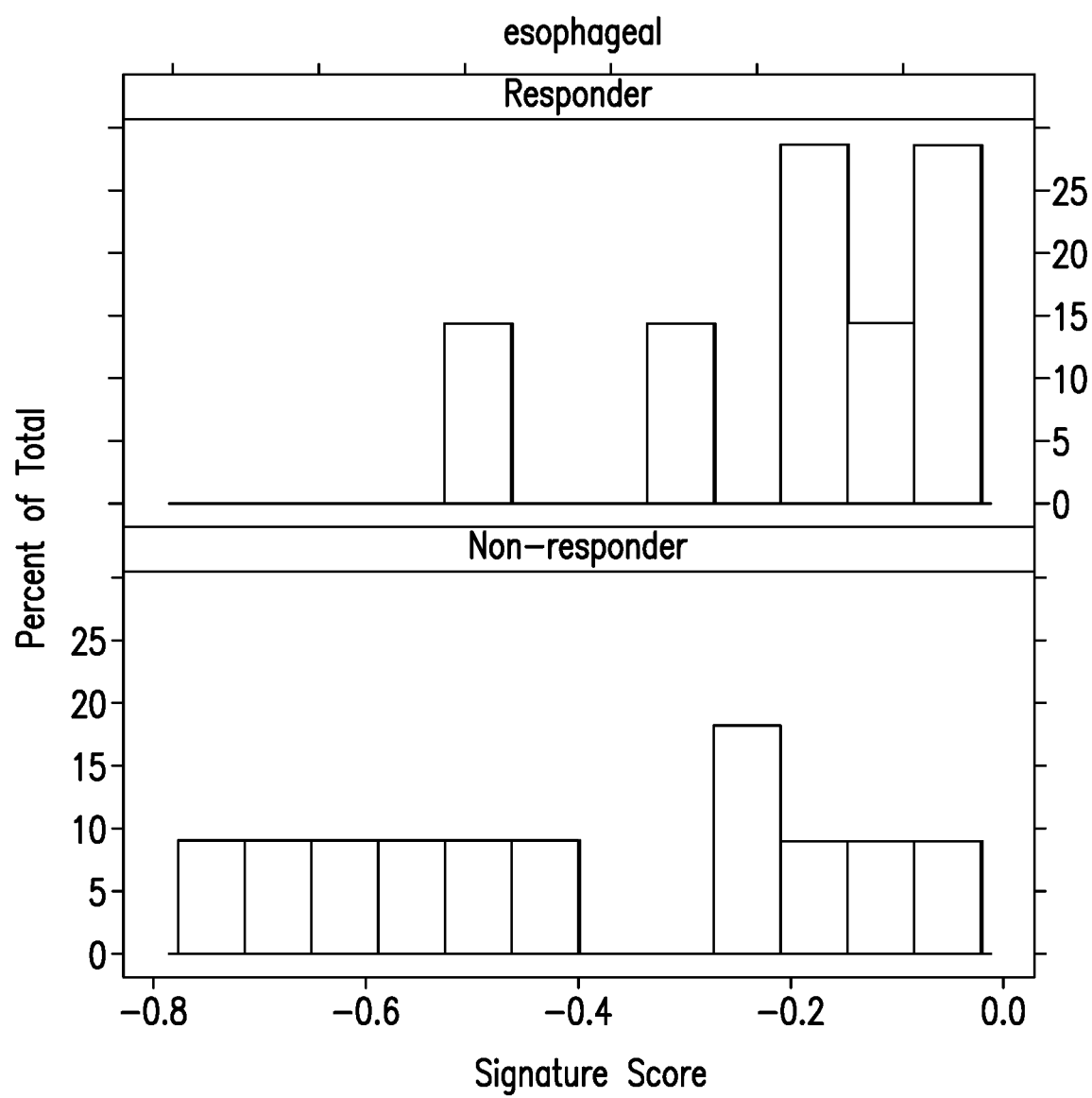
Figure 10A:
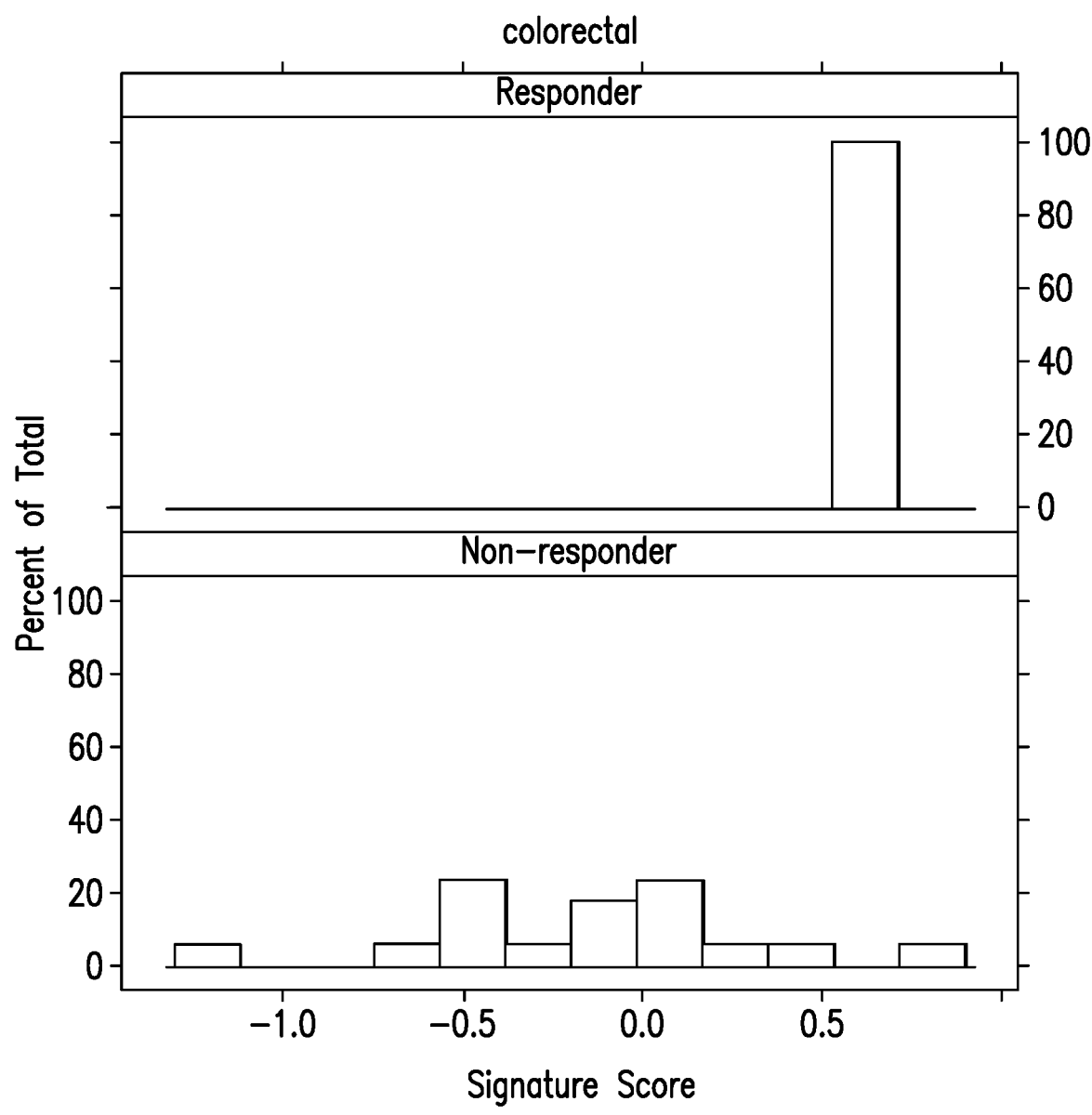
FIGS. 10A and 10B are histograms showing the distribution of pre-treatment signature scores for a 57 gene signature amongst colorectal cancer patients who responded (Responder) or did not respond (Non-responder) to pembrolizumab treatment, in which the signature scores were calculated using the exemplary scoring weight Set 1.1 (FIG. 10A) or Set 2.4 (FIG. 10B).
Figure 10B:
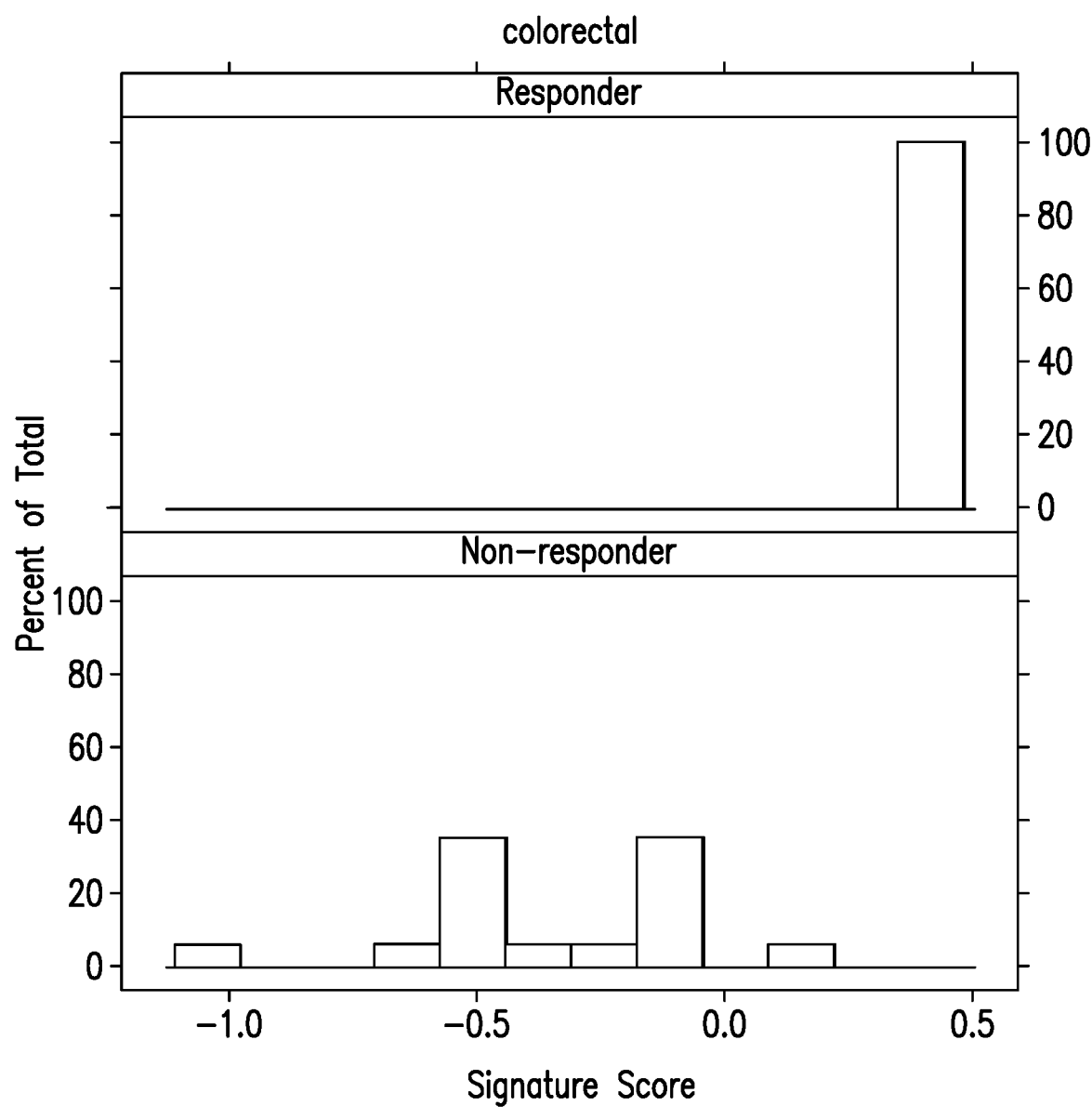
Figure 11A:
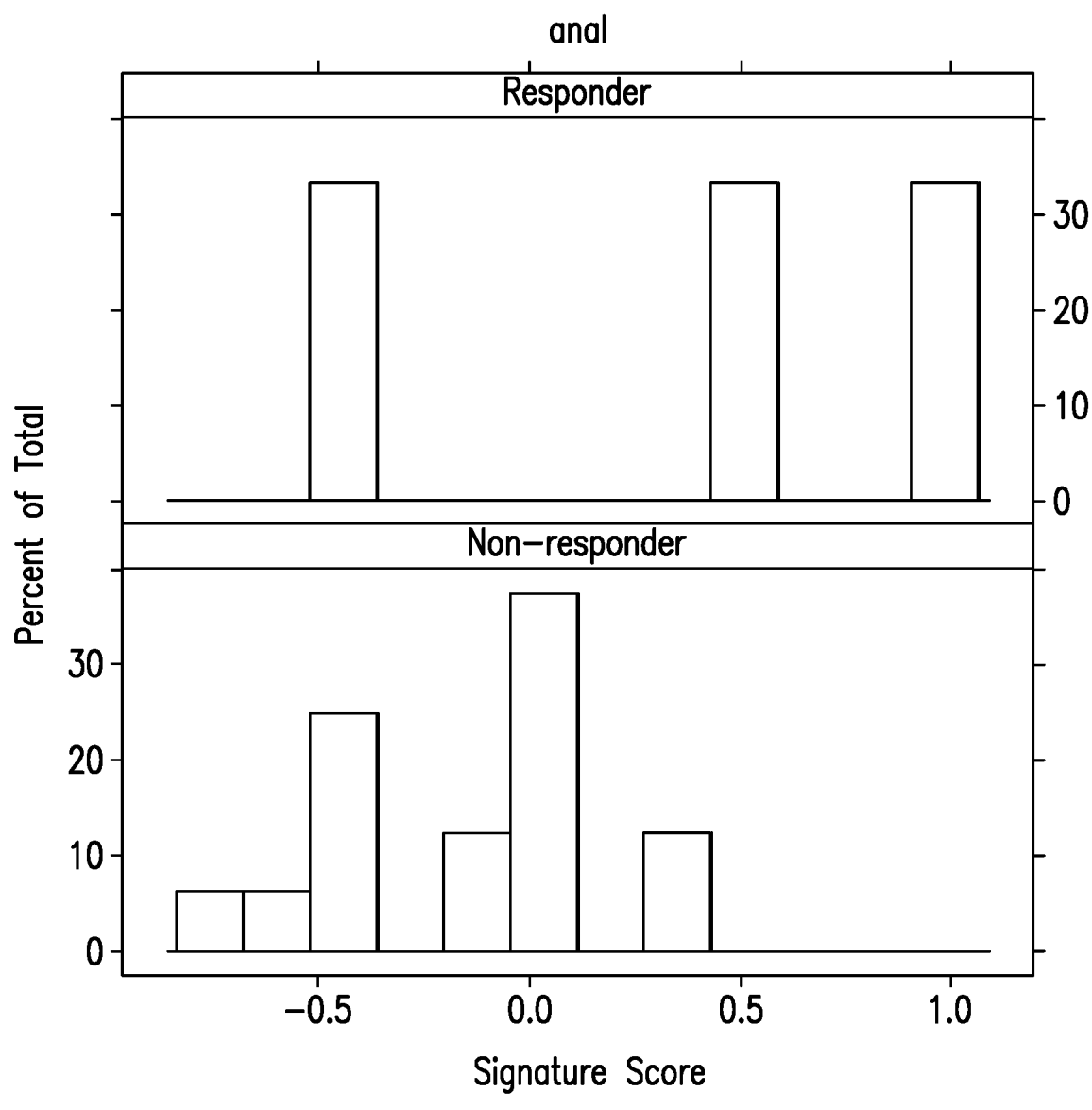
FIGS. 11A and 11B are histograms showing the distribution of pre-treatment signature scores for a 57 gene signature amongst anal cancer patients who responded (Responder) or did not respond (Non-responder) to pembrolizumab treatment, in which the signature scores were calculated using the scoring weight set identified in Set 1.1 (FIG. 11A) or Set 2.4 (FIG. 11B).
Figure 11B:
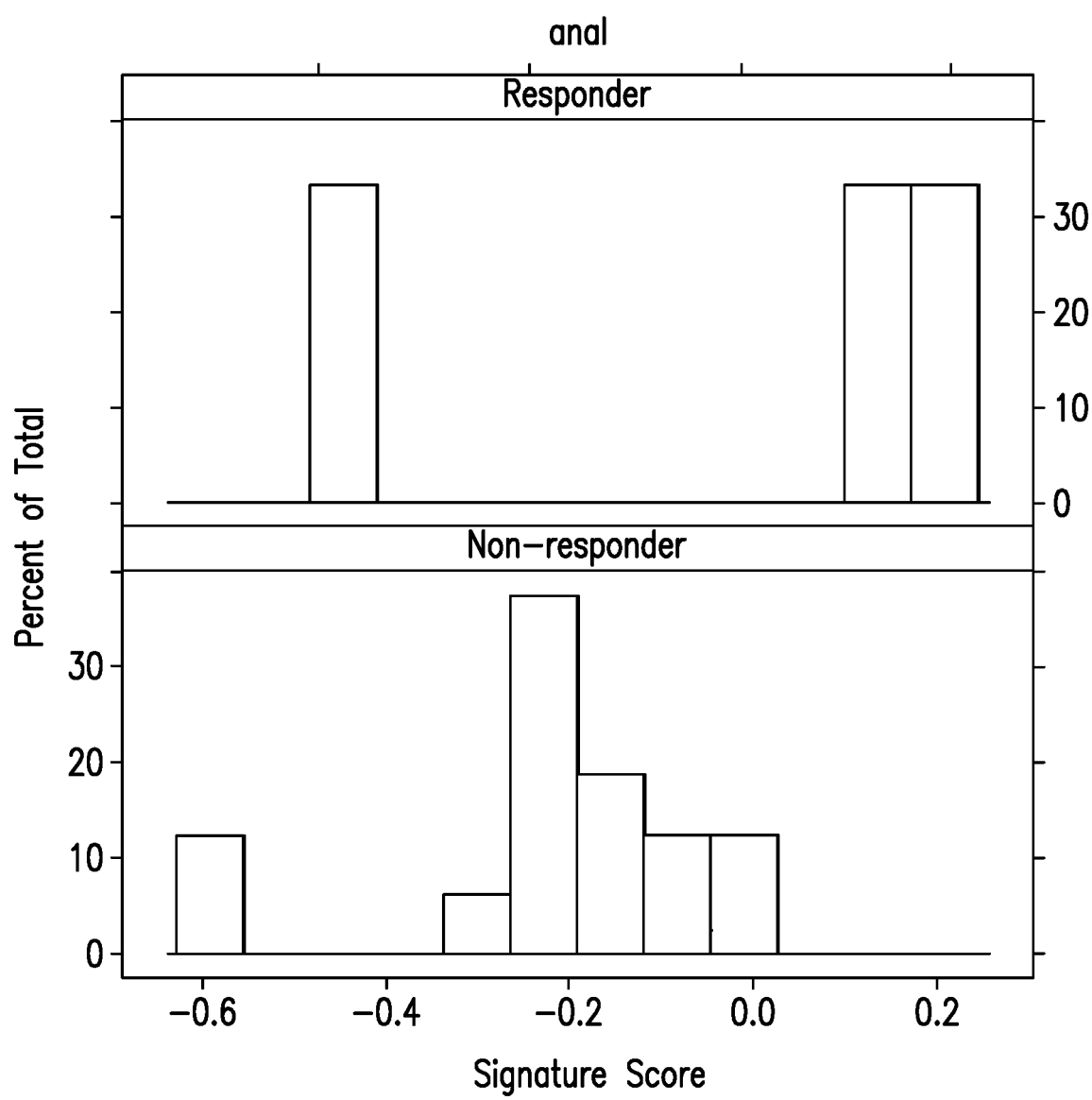

FIGS. 9 through 11 display the distribution of signature scores by pembrolizumab response status for three different cancers (esophageal, colorectal and anal), in which the signature scores were calculated using the scoring weights in Set 1.1 or Set 2.4. These data illustrate how signature scores have different distributions between responders and non-responders to pembrolizumab treatment. A predictive cut-off signature score could be selected for any or all of these cancer types by examining the PPV and NPV profiles and the implied prevalence of patients that would be selected using each candidate cut-off score.

REFERENCES

1. Sharpe, A. H, Wherry, E. J., Ahmed R., and Freeman G. J. The function of programmed cell death 1 and its ligands in regulating autoimmunity and infection. *Nature Immunology* (2007); 8:239-245.
2. Dong H et al. Tumor-associated B7-H1 promotes T-cell apoptosis: a potential mechanism of immune evasion. Nat Med. 2002 August; 8(8):793-800.
3. Yang et al. PD-1 interaction contributes to the functional suppression of T-cell responses to human uveal melanoma cells in vitro. *Invest Ophthalmol Vis Sci.* 2008 June; 49(6 (2008): 49: 2518-2525.
4. Ghebeh et al. The B7-H1 (PD-L1) T lymphocyte-inhibitory molecule is expressed in breast cancer patients with infiltrating ductal carcinoma: correlation with important high-risk prognostic factors. *Neoplasia* (2006) 8: 190-198.
5. Hamanishi J et al. Programmed cell death 1 ligand 1 and tumor-infiltrating CD8+T lymphocytes are prognostic factors of human ovarian cancer. *Proceeding of the National Academy of Sciences* (2007): 104: 3360-3365.
6. Thompson R H et al. Significance of B7-H1 overexpression in kidney cancer. Clinical genitourin *Cancer* (2006): 5: 206-211.
7. Nomi, T. Sho, M., Akahori, T., et al. Clinical significance and therapeutic potential of the programmed death-1 ligand/programmed death-1 pathway in human pancreatic cancer. *Clinical Cancer Research* (2007); 13:2151-2157.
8. Ohigashi Y et al. Clinical significance of programmed death-1 ligand-1 and programmed death-1 ligand 2 expression in human esophageal cancer. *Clin. Cancer Research* (2005): 11: 2947-2953.
9. Inman et al. PD-L1 (B7-H1) expression by urothelial carcinoma of the bladder and BCG-induced granulomata: associations with localized stage progression. *Cancer* (2007): 109: 1499-1505.
10. Shimauchi T et al. Augmented expression of programmed death-1 in both neoplasmatic and nonneoplastic CD4+ T-cells in adult T-cell Leukemia/Lymphoma. *Int. J. Cancer* (2007): 121:2585-2590.
11. Gao et al. Overexpression of PD-L1 significantly associates with tumor aggressiveness and postoperative recurrence in human hepatocellular carcinoma. *Clinical Cancer Research* (2009) 15: 971-979.
12. Nakanishi J. Overexpression of B7-H1 (PD-L1) significantly associates with tumor grade and postoperative prognosis in human urothelial cancers. *Cancer Immunol Immunother.* (2007) 56: 1173-1182.
13. Hino et al. Tumor cell expression of programmed cell death-1 is a prognostic factor for malignant melanoma. *Cancer* (2010): 00: 1-9.
14. Ghebeh H. Foxp3+ tregs and B7-H1+/PD-1+T lymphocytes co-infiltrate the tumor tissues of high-risk breast cancer patients: implication for immunotherapy. *BMC Cancer.* 2008 Feb. 23; 8:57.
15. Ahmadzadeh M et al. Tumor antigen-specific CD8 T cells infiltrating the tumor express high levels of PD-1 and are functionally impaired. *Blood* (2009) 114: 1537-1544.
16. Thompson R H et al. PD-1 is expressed by tumor infiltrating cells and is associated with poor outcome for patients with renal carcinoma. *Clinical Cancer Research* (2007) 15: 1757-1761.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The invention claimed is:

1. A method for treating a patient having a tumor which comprises determining if a sample of the tumor is positive or negative for a gene signature biomarker based on a gene signature score, wherein the gene signature score is calculated based on a combination of gene expression values for all of the genes in the gene signature biomarker, and administering to the patient a PD-1 antagonist if the tumor is positive for the biomarker or administering to the subject a cancer treatment that does not include a PD-1 antagonist if the tumor is negative for the biomarker, wherein the gene signature biomarker is for a gene signature that comprises the 18-Gene Up-Down Signature in Table 2 below:

TABLE 2

|   | 18 Gene Up-Down Signature |
|---|---|
| 1 | CCL5 |
| 2 | CD27 |
| 3 | CD274 |
| 4 | CD276 |
| 5 | CD8A |
| 6 | CMKLR1 |
| 7 | CXCL9 |
| 8 | CXCR6 |
| 9 | HLA.DQA1 |
| 10 | HLA.DRB1 |
| 11 | HLA.E |
| 12 | IDO1 |
| 13 | LAG3 |
| 14 | NKG7 |
| 15 | PDCD1LG2 |
| 16 | PSMB10 |
| 17 | STAT1 |
| 18 | TIGIT |

2. The method of claim 1, wherein the PD-1 antagonist administered to the patient if the tumor is positive is an antibody that blocks binding of both human PD-L1 and PD-L2 to human PD-1.

3. The method of claim 2, wherein the tumor is bladder cancer, colorectal cancer, gastric cancer, head and neck cancer, melanoma, non-small cell lung cancer, ovarian cancer, prostate cancer, anal cancer, biliary cancer, triple negative breast cancer, esophageal, or renal cancer.

4. The method of claim 3, wherein the tumor is colorectal cancer.

5. The method of claim 4, wherein the PD-1 antagonist administered to the patient if the tumor is positive is pembrolizumab.

6. The method of claim 3, wherein the PD-1 antagonist administered to the patient if the tumor is positive is pembrolizumab.

7. The method of claim 2, wherein the PD-1 antagonist administered to the patient if the tumor is positive is pembrolizumab.

* * * * *